(12) United States Patent
Yang et al.

(10) Patent No.: US 12,415,853 B2
(45) Date of Patent: Sep. 16, 2025

(54) ANTIBODY AGAINST CLAUDIN 18A2 AND USE THEREOF

(71) Applicant: QILU PHARMACEUTICAL CO., LTD., Shandong (CN)

(72) Inventors: Yingying Yang, Jinan (CN); Gao Li, Shandong (CN); Yaning Wang, Shandong (CN); Zhenming An, Shandong (CN); Shuyong Zhao, Shandong (CN); Yuxue Liu, Shandong (CN); Shicong Liu, Shandong (CN); Meijuan Zhang, Shandong (CN); Jinjin Jiang, Shandong (CN)

(73) Assignee: QILU PHARMACEUTICAL CO., LTD., Shandong (CN)

(*) Notice: Subject to any disclaimer, the term of this patent is extended or adjusted under 35 U.S.C. 154(b) by 910 days.

(21) Appl. No.: 17/611,551

(22) PCT Filed: May 15, 2020

(86) PCT No.: PCT/CN2020/090427
§ 371 (c)(1),
(2) Date: Nov. 15, 2021

(87) PCT Pub. No.: WO2020/228806
PCT Pub. Date: Nov. 19, 2020

(65) Prior Publication Data
US 2022/0411492 A1    Dec. 29, 2022

(30) Foreign Application Priority Data

May 16, 2019    (CN) .......................... 201910406762.4

(51) Int. Cl.
| | |
|---|---|
| C07K 16/28 | (2006.01) |
| A61K 31/136 | (2006.01) |
| A61K 31/282 | (2006.01) |
| A61K 31/513 | (2006.01) |
| A61K 31/69 | (2006.01) |
| A61K 38/20 | (2006.01) |
| A61K 39/00 | (2006.01) |
| A61K 39/395 | (2006.01) |
| A61K 45/06 | (2006.01) |
| A61K 47/68 | (2017.01) |
| A61P 35/00 | (2006.01) |
| C07K 14/725 | (2006.01) |
| G01N 33/574 | (2006.01) |

(52) U.S. Cl.
CPC ............ *C07K 16/28* (2013.01); *A61K 31/136* (2013.01); *A61K 31/282* (2013.01); *A61K 31/513* (2013.01); *A61K 31/69* (2013.01); *A61K 38/2026* (2013.01); *A61K 38/2066* (2013.01); *A61K 38/2086* (2013.01); *A61K 39/0011* (2013.01); *A61K 39/3955* (2013.01); *A61K 45/06* (2013.01); *A61K 47/6849* (2017.08); *A61K 47/6889* (2017.08); *A61P 35/00* (2018.01); *C07K 14/7051* (2013.01); *G01N 33/57492* (2013.01); *A61K 2039/572* (2013.01); *A61K 2039/80* (2018.08); *C07K 2317/24* (2013.01); *C07K 2317/31* (2013.01); *C07K 2317/52* (2013.01); *C07K 2317/54* (2013.01); *C07K 2317/55* (2013.01); *C07K 2317/569* (2013.01); *C07K 2317/732* (2013.01); *C07K 2317/734* (2013.01)

(58) Field of Classification Search
CPC ................ C07K 16/28; C07K 14/7051; C07K 2317/24; C07K 2317/31; C07K 2317/52; C07K 2317/54; C07K 2317/55; C07K 2317/569; C07K 2317/732; C07K 2317/734; C07K 2317/33; C07K 2317/92; A61K 31/136; A61K 31/282; A61K 31/513; A61K 31/69; A61K 38/2026; A61K 38/2066; A61K 38/2086; A61K 39/0011; A61K 39/3955; A61K 45/06; A61K 47/6849; A61K 47/6889; A61K 2039/572; A61K 2039/80; A61K 2039/505; A61P 35/00; G01N 33/57492
See application file for complete search history.

(56) References Cited

U.S. PATENT DOCUMENTS

| | | | |
|---|---|---|---|
| 10,053,512 B2 | 8/2018 | Sahin et al. | |
| 11,111,295 B2 | 9/2021 | Wang et al. | |
| 2017/0355756 A1* | 12/2017 | Julien ................. | C07K 16/18 |
| 2022/0073643 A1* | 3/2022 | Yin ..................... | C07K 16/28 |
| 2022/0185881 A1* | 6/2022 | Yang ................... | C07K 16/28 |

FOREIGN PATENT DOCUMENTS

| | | |
|---|---|---|
| CN | 104 427 999 | 3/2015 |
| CN | 105 073 777 | 11/2015 |

(Continued)

OTHER PUBLICATIONS

Trarbach, T., et al. "Efficacy and safety of multiple doses of IMAB362 in patients with advanced gastro-esophageal cancer: results of a phase II study." Annals of Oncology 25 (2014): iv218. (Year: 2014).*

(Continued)

*Primary Examiner* — Julie Wu
*Assistant Examiner* — Bryan William Heck
(74) *Attorney, Agent, or Firm* — Bayramoglu Law Offices LLC

(57) ABSTRACT

Provided are an anti-CLDN18.2 antibody or an antigen-binding fragment thereof, a derivative comprising said antibody or antigen-binding fragment thereof, a pharmaceutical composition, and related use of said antibody or antigen-binding fragment thereof for treating, diagnosing and detecting cancers.

18 Claims, 19 Drawing Sheets
Specification includes a Sequence Listing.

(56) References Cited

FOREIGN PATENT DOCUMENTS

| | | | |
|---|---|---|---|
| CN | 105 189 554 | 12/2015 | |
| CN | 107 667 118 | 2/2018 | |
| CN | 108 047 331 | 5/2018 | |
| EP | 3099706 B1 | 12/2016 | |
| KR | 1020180082325 A | 7/2018 | |
| KR | 1020190038564 A | 4/2019 | |
| RU | 2661772 C2 | 6/2016 | |
| WO | WO-2008068048 A2 * | 6/2008 | ............. A61P 31/10 |
| WO | WO 2013/174509 | 11/2013 | |
| WO | WO 2014/075788 | 5/2014 | |
| WO | WO 2015/113576 | 8/2015 | |
| WO | WO 2016/073649 | 5/2016 | |
| WO | WO 2016/165762 | 10/2016 | |
| WO | WO 2016/165765 | 10/2016 | |
| WO | WO 2016/166122 | 10/2016 | |
| WO | WO 2018/006882 | 1/2018 | |

OTHER PUBLICATIONS

Kiyoshi, Masato, et al. "Affinity improvement of a therapeutic antibody by structure-based computational design: generation of electrostatic interactions in the transition state stabilizes the antibody-antigen complex." PloS one 9.1 (2014): e87099. (Year: 2014).*

Rudikoff, Stuart, et al. "Single amino acid substitution altering antigen-binding specificity." Proceedings of the National Academy of Sciences 79.6 (1982): 1979-1983. (Year: 1983).*

Sela-Culang, Inbal, Vered Kunik, and Yanay Ofran. "The structural basis of antibody-antigen recognition." Frontiers in immunology 4 (2013): 302. (Year: 2013).*

Jarasch et al., "Developability Assessment During the Selection of Novel Therapeutic Antibodies." Journal of Pharmaceutical Sciences (2015) 104(6): 1885-1898.

Dirk, "Brain Tumor Stem Cells: Bringing Order to the Chaos of Brain Cancer," J Clin Oncol (2008) 26(17): 2916-2924.

Domingues et al., "Melanoma treatment in review/Immuno Targets and therapy," Immuno Targets and Therapy (2018) 7:35-49.

European Search Report for EP 20805122.7, dated Oct. 31, 2022, 8 pages.

Lopez-Lazaro, "The migration ability of stem cells can explain the existence of cancer of unknown primary site. Rethinking metastasis," Oncosscience (2015) 2:467.

Lu et al., "Acquired antagonistic activity of a bispecific diabody directed against two different epitopes on vascular endothelial growth factor receptor 2," J Immunol Methods (1999) 230:159-171.

Micke et al., "Aberrantly activated claudin 6 and 18.2 as potential therapy targets in non-small-cell lung cancer," Int J Cancer (2014) 135(9):2206-2214.

Notice of Reasons for Refusal for JP 2021-568260, dated Dec. 5, 2022, 8 pages (Including English translation).

Office Action for CA 3,138,414, dated Dec. 15, 2022, 7 pages (Including English translation).

Office Action for KR 10-2021-7040715, dated Jun. 19, 2024, 31 pages (Including English translation).

Office Action for RU 2021-137161/10, dated Jul. 12, 2023, 28 pages (Including English translation).

Solopova et al., "Bispecific Antibodies in Clinical Practice and Clinical Trials," (Literature Review) Clinical Oncohematology (2019) 12(2):125-144 (Including English abstract).

Tran et al., "Survival comparison between glioblastoma multiforme and other incurable cancers," J Clinical Neuroscience (2010) 17(4):417-421.

Wang et al., "Silence of MCL-1 upstream signaling by shRNA abrogates multiple myeloma growth," Experimental Hematology & Oncology (2014) 3:27.

International Search Report and Written Opinion for PCT/CN2020/090427, dated Aug. 18, 2020, 20 pages (Including English translation).

Moore, "Amino acid analysis: Aqueous Dimethyl Sulfoxide as solvent for the ninhydrin reaction," J Biol Chem (1968) 243(23):6281-6283.

Morin et al., "Claudin Proteins in Human Cancer: Promising New Targets for Diagnosis and Therapy," Cancer Res (2005) 65(21):9603-9606.

NCBI accession No. NM_001002026.3, *Homo sapiens* claudin 18 (CLDN18), transcript variant 2, mRNA. Retrieved on Oct. 21, 2021. Retrieved from https://www.ncbi.nlm.nih.gov/nuccore/NM_001002026.

NCBI accession No. NM_016369.4, *Homo sapiens* claudin 18 (CNDN18), transcript variant 1, mRNA. Retrieved on Dec. 21, 2021. Retrieved from https://www.ncbi.nlm.nih.gov/nuccore/NM_016369.4/.

NCBI accession No. NP_001002026.1, Claudin-18 isoform 2 [*Homo sapiens*]. Retrieved on Oct. 21, 2021. Retrieved from https://www.ncbi.nlm.nih.gov/protein/NP001002026.

NCBI accession No. NP_057453.1, Claudin-18 isoform 1 precursor [*Homo sapiens*]. Retrieved on Oct. 21, 2021. Retrieved from https://www.ncbi.nlm.nih.gov/protein/NP_057453.1/.

* cited by examiner

ANTIBODY AGAINST CLAUDIN 18A2 AND USE THEREOF

CROSS REFERENCE TO RELATED APPLICATIONS

This application is a national stage application under 35 U.S.C. § 371 of International Application No. PCT/CN2020/090427, filed internationally on May 15, 2020, which claims priority to Chinese patent application No. 201910406762.4 filed May 16, 2019. The contents of the above patent applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 166102000400SeqList.txt, date recorded: Nov. 15, 2021, size: 70,757 bytes).

TECHNICAL FIELD

The present disclosure pertains to the field of immunology, and more particularly to antibodies against Claudin 18.2 (CLDN18A2, CLDN18.2) or antigen-binding fragments thereof, derivatives comprising the antibodies or antigen-binding fragments thereof, pharmaceutical compositions, and related uses thereof in the treatment of cancer.

BACKGROUND

Claudins are integral membrane proteins comprising a major structural proteins of tight junctions, such as the apical cell-cell adhesive junctions in polarized cell types seen in epithelial or endothelial cell layers. The tight junctions are composed of multi-strands reticular proteins that form a continuous seal around the cell, providing a physical barrier to solute and water transport in the paracellular space, but which is adjustable. The family of claudins contains at least 23 members in humans, ranging from 22 to 34 kDa in size. Although claudins are important for the function and stability of normal tissues, tumor cells often exhibit aberrant tight junction function. This may be associated with dysregulated expression and/or location of claudins due to dedifferentiation of tumor cells or the requirement for effective absorption of nutrients in tumor masses with abnormal angiogenesis by fast-growing cancer tissues (Morin, 2005, PMID: 16266975). Individual claudin family members may be up-regulated in certain cancer types, but down-regulated in other cancer types. Claudin 18 (CLDN18) is an integral membrane protein located in the tight junctions of epithelium and endothelium, with a molecular weight of about 27.9 KD. CLDN18 forms intercellular tight junctions with other tight junction proteins, regulating the permeability of tissue molecules and ions in the intercellular space, and maintaining the stability of the tissue environment. It is known that there are 2 subtypes of claudin 18, splice variant 1 (CLDN18A1, CLDN18.1): GenBank Accession Nos. NP_057453 and NM016369, and splice variant 2 (CLDN18A2, CLDN18.2): GenBank Accession Nos. NM_001002026 and NP_001002026. In normal cells, CLDN18A1 is selectively expressed in the epithelial cell of the lung, while CLDN18A2 is specifically expressed in normal gastric epithelial differentiated cells and not expressed in gastric epithelial stem cells with cell division activity. However, CLDN18A2 is overexpressed in tumor cells in many cancer types, such as high expression of CLDN18A2 found in 75% of gastric cancer patients, 50% of pancreatic cancer patients, and 30% of esophageal cancer patients, also in lung cancer and other cancer types. Therefore, finding antibodies that specifically bind to CLDN18A2 but not CLDN18A1 is of great significance for the treatment and detection of cancer. The existing CLDN18A2 antibody IMAB362 has entered the clinical research stage, clinical results showed that in gastric cancer patients with high expression of CLDN18.2 (≥70% of tumor cells with CLDN18.2 expression ≥2+), compared with chemotherapy alone, the progression-free survival of chemotherapy+IMAB362 was extended from 6.1 months to 9.1 months, HR=0.46; the total survival time was extended from 9.3 months to 16.6 months, HR=0.44. In addition to antibody IMAB362, CAR-T prepared against CLDN18.2 targets has also entered clinical studies. However, these antibodies (or antigen-binding fragments in CAR-T) that have entered the clinical stage have less affinity to claudin 18.2. Therefore, there remains a need to continue to screen and prepare CLDN18.2 antibodies with higher affinity to produce greater potency at the same dosage.

SUMMARY OF THE INVENTION

The present disclosure provides an anti-CLDN18.2 antibody or antigen-binding fragment thereof that specifically binds to CLDN18.2 and does not significantly bind to CLDN18.1.

In some embodiments, the CLDN18.2 is a peptide having GenBank Accession No. NP_001002026 (mRNA: NM_001002026). The CLDN18.1 is a peptide having GenBank Accession No. NP_057453 (mRNA:NM_016369).

In some embodiments, there is no significant binding between an antibody or antigen-binding fragment thereof of the present disclosure and CLDN18.1. In some examples, the antibody or antigen-binding fragment thereof binds to CLDN18.1 at a level of no more than 20% of that of binding to CLDN18.2. For example, the level of binding may be 20%, 19%, 18%, 17%, 16%, 15%, 14%, 13%, 12%, 11%, 10%, 9%, 8%, 7%, 6%, 5%, 4%, 3%, 2%, 1% or less than 1% of that of binding of the antibody or antigen-binding fragment thereof to CLDN18.2. In some embodiments, the antibody or antigen-binding fragment thereof of the present disclosure binds to CLDN18.2 at a level 1-fold, 2-fold, 3-fold, 4-fold, 5-fold, 6-fold, 7-fold, 8-fold, 9-fold, 10-fold, or more than 10-fold greater than that of binding to CLDN18.1.

The present disclosure provides an anti-CLDN18.2 antibody or antigen-binding fragment thereof, the antibody or antigen-binding fragment thereof is capable of specifically binding to CLDN18.2, comprising: a heavy chain variable region, the heavy chain variable region comprises three HCDRs selected from the group consisting of SEQ ID NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85; and/or, a light chain variable region, the light chain variable region comprises three LCDRs selected from the group consisting of SEQ ID NOs: 86, 87, 88, 89, 90, 91, 92, 93, 94, 95, 96, 97, 98, 99, 100, 101, 102, 103, 104, 105, 106, 107, 108, 109, 110, 111, 112, 113.

In some embodiments, the present disclosure provides an anti-CLDN18.2 antibody or antigen-binding fragment thereof comprising a heavy chain variable region and/or a light chain variable region, the heavy chain variable region comprises HCDR1 selected from the group consisting of SEQ ID NOs: 37, 40, 43, 45, 49, 53, 56, 59, 62, 65, 68, 71, 74, 77, 80, 83; and HCDR2 selected from the group consisting of SEQ ID NOs: 38, 41, 46, 48, 50, 52, 54, 57, 60, 63, 66, 69, 72, 75, 78, 81, 84; and HCDR3 selected from the group consisting of SEQ ID NOs: 39, 42, 44, 47, 51, 55, 58, 61, 64, 67, 70, 73, 76, 79, 82, 85; and/or, the light chain variable region comprising LCDR1 selected from the group consisting of SEQ ID NOs: 86, 87, 88, 89, 90, 91, 92, 111, 112, 113; and LCDR2 selected from the group consisting of SEQ ID NOs: 93, 94, 95, 96; and LCDR3 selected from the group consisting of SEQ ID NOs: 97, 98, 99, 100, 101, 102, 103, 104, 105, 106, 107, 108, 109, 110.

In a preferred embodiment, the present disclosure provides an anti-CLDN18.2 antibody or antigen-binding fragment thereof comprising a heavy chain variable region and/or a light chain variable region, the heavy chain variable region comprises HCDR1, HCDR2, and HCDR3 selected from the group consisting of:
  SEQ ID NO: 37, SEQ ID NO: 38 and SEQ ID NO: 39 or
  SEQ ID NO: 40, SEQ ID NO: 41 and SEQ ID NO: 42 of
  SEQ ID NO: 43, SEQ ID NO: 41 and SEQ ID NO: 44 or
  SEQ ID NO: 45, SEQ ID NO: 46 and SEQ ID NO: 47 or
  SEQ ID NO: 37, SEQ ID NO: 48 and SEQ ID NO: 39 or
  SEQ ID NO: 49, SEQ ID NO: 50 and SEQ ID NO: 51 or
  SEQ ID NO: 49, SEQ ID NO: 52 and SEQ ID NO: 51 or
  SEQ ID NO: 53, SEQ ID NO: 54 and SEQ ID NO: 55 or
  SEQ ID NO: 56, SEQ ID NO: 57 and SEQ ID NO: 58 or
  SEQ ID NO: 59, SEQ ID NO: 60 and SEQ ID NO: 61 or
  SEQ ID NO: 62, SEQ ID NO: 63 and SEQ ID NO: 64 of
  SEQ ID NO: 65, SEQ ID NO: 66 and SEQ ID NO: 67 or
  SEQ ID NO: 68, SEQ ID NO: 69 and SEQ ID NO: 70 or
  SEQ ID NO: 71, SEQ ID NO: 72 and SEQ ID NO: 73 or
  SEQ ID NO: 74, SEQ ID NO: 75 and SEQ ID NO: 76 or
  SEQ ID NO: 77, SEQ ID NO: 78 and SEQ ID NO: 79 or
  SEQ ID NO: 80, SEQ ID NO: 81 and SEQ ID NO: 82 of
  SEQ ID NO: 83, SEQ ID NO: 84 and SEQ ID NO: 85;
  and/or the light chain variable region comprises LCDR1, LCDR2, and LCDR3 selected from the group consisting of:
  SEQ ID NO: 86, SEQ ID NO: 93 and SEQ ID NO: 97, or
  SEQ ID NO: 87, SEQ ID NO: 94 and SEQ ID NO: 98; or
  SEQ ID NO: 88, SEQ ID NO: 93 and SEQ ID NO: 99; or
  SEQ ID NO: 87, SEQ ID NO: 95 and SEQ ID NO: 100; or
  SEQ ID NO: 88, SEQ ID NO: 93 and SEQ ID NO: 97; or
  SEQ ID NO: 88, SEQ ID NO: 93 and SEQ ID NO: 101; or
  SEQ ID NO: 89, SEQ ID NO: 93 and SEQ ID NO: 102; or
  SEQ ID NO: 88, SEQ ID NO: 93 and SEQ ID NO: 100; or
  SEQ ID NO: 90, SEQ ID NO: 93 and SEQ ID NO: 103; or
  SEQ ID NO: 91, SEQ ID NO: 96 and SEQ ID NO: 104; or
  SEQ ID NO: 88, SEQ ID NO: 93 and SEQ ID NO: 98; or
  SEQ ID NO: 92, SEQ ID NO: 93 and SEQ ID NO: 105; or
  SEQ ID NO: 88, SEQ ID NO: 93 and SEQ ID NO: 106; or
  SEQ ID NO: 88, SEQ ID NO: 93 and SEQ ID NO: 107; or
  SEQ ID NO: 87, SEQ ID NO: 93 and SEQ ID NO: 108; or
  SEQ ID NO: 88, SEQ ID NO: 93 and SEQ ID NO: 109; or
  SEQ ID NO: 88, SEQ ID NO: 93 and SEQ ID NO: 110; or
  SEQ ID NO: 111, SEQ ID NO: 93 and SEQ ID NO: 107; or
  SEQ ID NO: 112, SEQ ID NO: 93 and SEQ ID NO: 107; or
  SEQ ID NO: 113, SEQ ID NO: 93 and SEQ ID NO: 107; or
  SEQ ID NO: 111, SEQ ID NO: 93 and SEQ ID NO: 110; or
  SEQ ID NO: 112, SEQ ID NO: 93 and SEQ ID NO: 110; or
  SEQ ID NO: 113, SEQ ID NO: 93 and SEQ ID NO: 110.

According to one aspect of the present disclosure, the anti-CLDN18.2 antibody or antigen-binding fragment thereof comprises a heavy chain variable region and a light chain variable region, the variable region comprising 6 CDRs from any one of the following groups, the 6 CDRs of each group being arranged in order of HCDR1, HCDR2, HCDR3, LCDR1, LCDR2, LCDR3:
  (1) SEQ ID NOs: 37, 38, 39, 86, 93, 97;
  (2) SEQ ID NOs: 40, 41, 42, 87, 94, 98;
  (3) SEQ ID NOs: 43, 41, 44, 88, 93, 99;
  (4) SEQ ID NOs: 45, 46, 47, 87, 95, 100;
  (5) SEQ ID NOs: 37, 48, 39, 88, 93, 97;
  (6) SEQ ID NOs: 49, 50, 51, 88, 93, 101;
  (7) SEQ ID NOs: 49, 52, 51, 89, 93, 102;
  (8) SEQ ID NOs: 53, 54, 55, 88, 93, 100;
  (9) SEQ ID NOs: 56, 57, 58, 90, 93, 103;
  (10) SEQ ID NOs: 59, 60, 61, 91, 96, 104;
  (11) SEQ ID NOs: 62, 63, 64, 88, 93, 98;
  (12) SEQ ID NOs: 65, 66, 67, 92, 93, 105;
  (13) SEQ ID NOs: 68, 69, 70, 88, 93, 106;
  (14) SEQ ID NOs: 71, 72, 73, 88, 93, 107;
  (15) SEQ ID NOs: 74, 75, 76, 88, 93, 106;
  (16) SEQ ID NOs: 77, 78, 79, 87, 93, 108;
  (17) SEQ ID NOs: 80, 81, 82, 88, 93, 109;
  (18) SEQ ID NOs: 83, 84, 85, 88, 93, 110;
  (19) SEQ ID NOs: 71, 72, 73, 111, 93, 107;
  (20) SEQ ID NOs: 71, 72, 73, 112, 93, 107;
  (21) SEQ ID NOs: 71, 72, 73, 113, 93, 107;
  (22) SEQ ID NOs: 83, 84, 85, 111, 93, 110;
  (23) SEQ ID NOs: 83, 84, 85, 112, 93, 110;
  (24) SEQ ID NOs: 83, 84, 85, 113, 93, 110.

In some embodiments, the present disclosure provides an anti-CLDN18.2 antibody or antigen-binding fragment thereof comprising a heavy chain variable region and/or a light chain variable region, the heavy chain variable region has at least 80%, 85%, 90%, 95%, or 100% sequence identity to: SEQ ID NOs: 1, 3, 5, 7, 9, 11, 13, 15, 17, 19, 21, 23, 25, 27, 29, 31, 33, 35; and/or, the light chain variable region has at least 80%, 85%, 90%, 95%, or 100% sequence identity to: SEQ ID NOs: 2, 4, 6, 8, 10, 12, 14, 16, 18, 20, 22, 24, 26, 28, 30, 32, 34, 36, 114, 115, 116, 117, 118, 119.

According to one aspect of the present disclosure, the anti-CLDN18.2 antibody or antigen-binding fragment thereof comprises at least 80% to 100% sequence identity to a heavy chain variable region and a light chain variable region of any one of the groups consisting of:
  (1) SEQ ID NOs: 1 and 2;
  (2) SEQ ID NOs: 3 and 4;
  (3) SEQ ID NOs: 5 and 6;
  (4) SEQ ID NOs: 7 and 8;
  (5) SEQ ID NOs: 9 and 10;
  (6) SEQ ID NOs: 11 and 12;

(7) SEQ ID NOs: 13 and 14;
(8) SEQ ID NOs: 15 and 16;
(9) SEQ ID NOs: 17 and 18;
(10) SEQ ID NOs: 19 and 20;
(11) SEQ ID NOs: 21 and 22;
(12) SEQ ID NOs: 23 and 24;
(13) SEQ ID NOs: 25 and 26;
(14) SEQ ID NOs: 27 and 28;
(15) SEQ ID NOs: 29 and 30;
(16) SEQ ID NOs: 31 and 32;
(17) SEQ ID NOs: 33 and 34;
(18) SEQ ID NOs: 35 and 36;
(19) SEQ ID NOs: 27 and 114;
(20) SEQ ID NOs: 27 and 115;
(21) SEQ ID NOs: 27 and 116;
(22) SEQ ID NOs: 35 and 117;
(23) SEQ ID NOs: 35 and 118;
(24) SEQ ID NOs: 35 and 119.

In some preferred embodiments, the anti-CLDN18.2 antibody or antigen-binding fragment thereof described herein is a murine antibody, a chimeric antibody, or a humanized antibody.

In some embodiments, the present disclosure provides an anti-CLDN18.2 antibody or antigen-binding fragment thereof comprising a heavy chain variable region and the light chain variable region, the heavy chain variable region has at least 80%, 85%, 90%, 95%, or 100% sequence identity to: SEQ ID NOs: 120, 122, 125, 128; and/or, the light chain variable region has at least 80%, 85%, 90%, 95%, or 100% sequence identity to: SEQ ID NOS: 121, 123, 124, 126, 127.

According to one aspect of the present disclosure, the anti-CLDN18.2 antibody or antigen-binding fragment thereof comprises at least 80%, 85%, 90%, 95%, or 100% sequence identity to a heavy chain variable region and a light chain variable region of any one of the groups consisting of:

(1) SEQ ID NOs: 120 and 121;
(2) SEQ ID NOs: 120 and 123;
(3) SEQ ID NOs: 120 and 124;
(4) SEQ ID NOs: 122 and 121;
(5) SEQ ID NOs: 125 and 126;
(6) SEQ ID NOs: 125 and 127;
(7) SEQ ID NOs: 128 and 126.

In some preferred embodiments, the anti-CLDN18.2 antibody is a monoclonal antibody.

In some preferred embodiments, the anti-CLDN18.2 antibody or antigen-binding fragment thereof further comprises a heavy chain constant region and/or a light chain constant region, preferably the heavy chain constant region comprises an Fc or a variant Fc, and the Fc is derived from a mouse or a human.

In some preferred embodiments, the anti-CLDN18.2 antibody is a full-length antibody.

In some preferred embodiments, an anti-CLDN18.2 antibody or antigen-binding fragment thereof of the present disclosure is in the form of IgG1, IgG2, IgG3, or IgG4.

In some preferred embodiments, the antigen-binding fragments of the present disclosure include Pab, Fv, scFv, F(ab')$_2$, linear antibodies, and single-domain antibodies.

In some embodiments, the present disclosure provides a conjugate formed by coupling the afore-mentioned antibody or antigen-binding fragment thereof to a capture label or a detection label. Such detection labels include but are not limited to, radionuclides, luminescent substances (e.g., fluorescein), colored substances, or enzymes.

In some embodiments, the present disclosure provides a bispecific or multispecific antibody, one antigen-binding domain of the bispecific or multispecific antibody comprises an anti-CLDN18.2 antibody or antigen-binding fragment thereof of the present disclosure.

In some embodiments, the present disclosure provides an antibody-drug conjugate comprising an antibody or antigen-binding fragment thereof as previously described. The structure of such antibody-drug conjugates is well known in the art and is formed by the interconnection of antibody-linker-drug (toxin).

In some embodiments, the present disclosure provides a chimeric antigen receptor in which an extracellular recognition unit comprises an antibody or antigen-binding fragment thereof as previously described.

In some embodiments, the present disclosure provides a nucleic acid encoding any of the afore-mentioned antibodies or antigen-binding fragments thereof. According to another aspect of the present disclosure, there is provided a recombinant vector comprising the nucleic acid.

In some embodiments, the present disclosure provides a host cell comprising the expression vector of the present disclosure or genome of which is integrated with the nucleic acid encoding the antibody or antigen-binding fragment thereof. In some preferred embodiments, the host cell may be a prokaryotic cell, such as *E. coli*; may also be eukaryotic cells such as yeast or mammalian cells such as CHO cells or HEK293 cells.

In some embodiments, the present disclosure provides a method of preparing the antibody or antigen-binding fragment thereof, comprising: culturing the host cells of the present disclosure under suitable conditions and purifying the expression products from the cells.

In some embodiments, the present disclosure provides the use of the antibody or antigen-binding fragment thereof for the preparation of a drug specifically targets CLDN18.2-expressing tumor cells, such as a monoclonal antibody drug, an antibody-drug conjugate, a bispecific antibody, or a multispecific antibody; or for the preparation of an immune cell modified by a chimeric antigen receptor; or for the preparation of a reagent for the diagnosis of a CLDN18.2-expressing tumor; in some embodiments, the CLDN18.2-expressing tumor comprises: gastric cancer, pancreatic cancer, esophageal cancer, lung cancer, ovarian cancer, colon cancer, liver cancer, head and neck cancer, and gallbladder cancer and metastases thereof, the gastric cancer metastasis such as Kuckenberg tumor.

In some embodiments, the present disclosure provides a method of detecting CLDN18.2 expression in a sample, comprising: contacting the sample with the afore-mentioned anti-CLDN18.2 antibody or antigen-binding fragment thereof; detecting the formation of a complex of an anti-CLDN18.2 antibody or antigen-binding fragment thereof and CLDN18.2; optionally, the anti-CLDN18.2 antibody or antigen-binding fragment thereof is detectably labeled.

In some embodiments, the present disclosure provides a pharmaceutical composition comprising an effective amount of an antibody or antigen-binding fragment thereof of the present disclosure, or comprising an effective amount of a nucleic acid encoding the antibody or antigen-binding fragment thereof, or comprising an effective amount of a recombinant vector comprising a coding nucleic acid, or comprising an effective amount of a host cell comprising a coding nucleic acid, or comprising an effective amount of an antibody-drug conjugate of the present disclosure, or comprising an effective amount of a chimeric antigen receptor of the present disclosure, or comprising an effective amount of a bispecific or multispecific antibody of the present disclosure. In some embodiments, the pharmaceutical composition further comprises a pharmaceutically acceptable carrier.

In some preferred embodiments, the pharmaceutical composition further comprises one or more additional therapeutic agents. Such additional therapeutic agents include cytotoxic agents, cytostatic agents, anti-angiogenic agents, anti-neoplastic agents, chemotherapeutic agents, radiotherapeutic agents, targeted anti-cancer agents, biological response modifiers, cancer vaccines, cytokines, hormones, anti-metastatic agents, and immunotherapeutic agents.

In some embodiments, the present disclosure provides a drug box or a kit comprising a container and a pharmaceutical composition of the present disclosure in the container.

In some embodiments, the present disclosure provides a method of inducing death in CLDN18.2-expressing cells, comprising contacting the cells with the pharmaceutical composition of the present disclosure. In some embodiments, the cells are contacted with the pharmaceutical composition in vitro. In some embodiments, the cells are contacted with the pharmaceutical composition in vivo. In some embodiments, the cell is a tumor cell.

In some embodiments, the cell is a solid tumor cell. In some embodiments, the cell is selected from the group consisting of gastric cancer cells, esophageal cancer cells, intestinal cancer cells, pancreatic cancer cells, nephroblastoma cells, lung cancer cells, ovarian cancer cells, colon cancer cells, rectal cancer cells, liver cancer cells, head and neck cancer cells, chronic myelogenous leukemia cells, and gallbladder cancer cells.

In some embodiments, the present disclosure provides a method of treating a disease associated with expression of CLDN18.2 in a subject, comprising administering to a subject in need thereof a pharmaceutical composition of the present disclosure. In some embodiments, the disease is a tumor. In some embodiments, the tumor is preferably gastric cancer, esophageal cancer, intestinal cancer, pancreatic cancer, nephroblastoma, lung cancer, ovarian cancer, colon cancer, rectal cancer, liver cancer, head and neck cancer, chronic myelogenous leukemia, or gallbladder cancer. In some embodiments, the method further comprises administering to the subject an additional therapeutic agent.

The antibodies of the present disclosure may be administered in combination with another additional therapeutic agent, including, but not limited to, chemotherapeutic agents, cytotoxic agents, radiotherapeutic agents, cancer vaccines, anti-neoplastic agents, targeted anti-cancer agents, anti-angiogenic agents, biological response modifiers, cytokines, hormones, anti-metastatic agents, and immunotherapeutic agents.

In some preferred embodiments, the chemotherapeutic agents that can be used in combination with an antibody or antigen-binding fragment thereof of the present disclosure include but are not limited to, mitotic inhibitors, including vincristine, vinblastine, vindesine, and navelbine; topoisomerase I inhibitors, such as camptothecin compounds, including irinotecan, topotecan and other compounds derived from camptothecin and analogs thereof; podophyllotoxin derivatives such as etoposide, teniposide, and midoxizoz; alkylating agents such as cisplatin, carboplatin, cyclophosphamide, nitrogen mustard, trimethylenethiophosphoramide, carmustine, busulfan, chlorambucil, briquinolizine, uracil mustard, cloprofen, and dacarbazine; antimetabolites, including cytarabine, 5-fluorouracil, methotrexate, mercaptopurine, azathioprine, and procarbazine; antibiotics including, but not limited to, doxorubicin, bleomycin, dactinomycin, daunorubicin, mitomycin, sarcomycin C, actinomycin D, roxithromycin, adriamycin, rapamycin and derivatives thereof, and daunomycin; and other chemotherapeutic agents including, but not limited to, paclitaxel, docetaxel, dacarbazine, azacytidine, amsacon melphalan, ifosfamide, and mitoxantrone. In some preferred embodiments, the additional therapeutic agent is selected from one or more of epirubicin, oxaliplatin, and 5-fluorouracil.

In some embodiments, the targeted anticancer agents include but are not limited to, large molecule-targeted drugs, small molecule-targeted drugs, etc.

In some preferred embodiments, the macromolecular targeting agents include but are not limited to, epidermal growth factor-targeted agents, including cetuximab, panitumumab, and nimotuzumab, etc.; HER-2 or HER-3 signaling pathway inhibitors, including trastuzumab, pertuzumab, T-DM1, etc.; anti-vascular endothelial growth factor drugs, including VEGF-TRAP, bevacizumab, ramucirumab, etc.; also, agents targeting other targets include but are not limited to, targets such as PI3K, PARP, PI3Kα, PKB/AKT, and STAT3.

In some embodiments, small molecule-targeted agents include but are not limited to, epidermal growth factor targeting agents, including erlotinib or gefitinib, etc.; HER-2 or HER-3 signaling pathway inhibitors, including lapatinib or afatinib, etc.; tyrosine kinase inhibitors including imatinib or sunitinib, etc.; anti-vascular endothelial growth factor drugs including sorafenib, regorafenib, pazopanib, recombinant human endostatin, apatinib, etc.; targeting c-Met/ROS1 drugs, including crizotinib, etc.; and, other targeting agents, including but not limited to vorinostat and marimastat, etc.; targeting mTOR drugs, including everolimus, etc.; and agents targeting other targets including but not limited to PI3Kα, PKB/AKT, and STAT3.

In some embodiments, the immunotherapeutic agents include but are not limited to, immunosuppressive agents and agonists, wherein the targets include PD-1/PD-L1, PD-L2, CTLA-4, LAG-3, IDO, TIM3, TIGIT, CD47, SIRPα, 4-1BB, CSF-1/CSF1R, GITR, OX40, CD40, CD27, CD28, B7H4, B7H3, TGFβ, BTLA, VISTA, ICOS, CD39, CD73, A2AR, KIR, and NKG2A, etc.; and cell therapy associated with immunotherapy.

In some embodiments, immune checkpoint inhibitors that target PD-1/PD-L1 include but are not limited to, macromolecular drugs such as, Pembrolizumab, Nivolumab, Atezolizumab, Avelumab, Sintilimab, Cemiplimab, and Durvalumab, etc.; and small molecule drugs.

In some embodiments, immune checkpoint inhibitors that target CTLA-4 include but are not limited to, Ipilimumab, etc.; cytokines include but are not limited to, IL-10, IL-15, IL4, and IL13, etc.; inhibitors that target BRAF include but are not limited to, Binimetinib, etc.

In some embodiments, the other therapeutic agent is selected from oncolytic viruses, such as parvovirus, adenovirus, herpes virus, poxvirus, poliovirus, reovirus, alphavirus, maraba virus, retrovirus, and coxsackie virus, etc.; alternatively, the other therapeutic agent is selected from cancer vaccines or protease inhibitors, such as bortezomib, etc.

BRIEF DESCRIPTION OF DRAWINGS

The drawings further illustrate the novel features disclosed in this specification. The features and advantages disclosed in this specification will be better understood with reference to the drawings, but it is to be understood that these drawings are merely illustrative of specific embodi

DETAILED DESCRIPTION OF THE INVENTION

Terms

Figure 1:
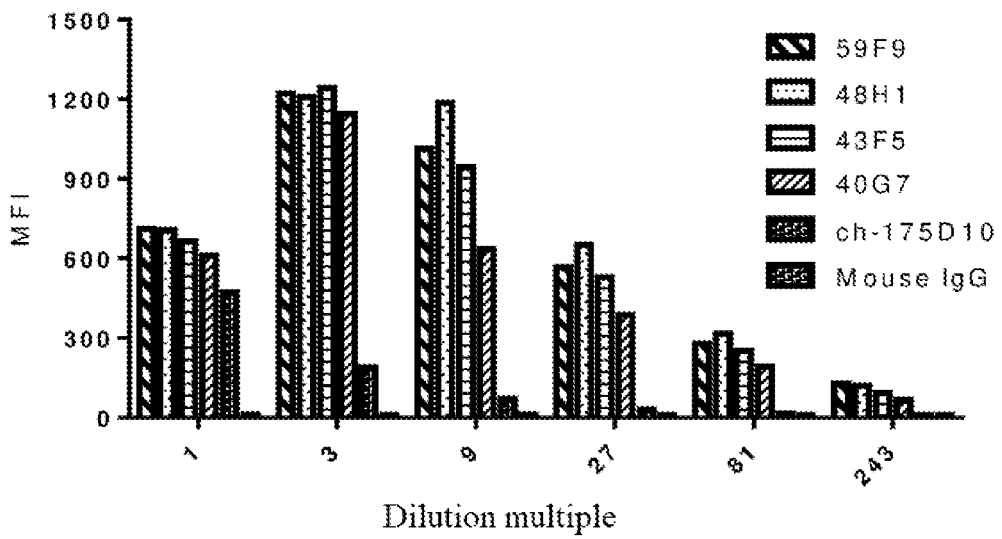
- FIGS. 1-5 show the binding of supernatants from 18 hybridoma cell lines of the present disclosure to HEK293 cells stably transformed with hCLDN18.2 as measured by flow cytometry.
Figure 2:
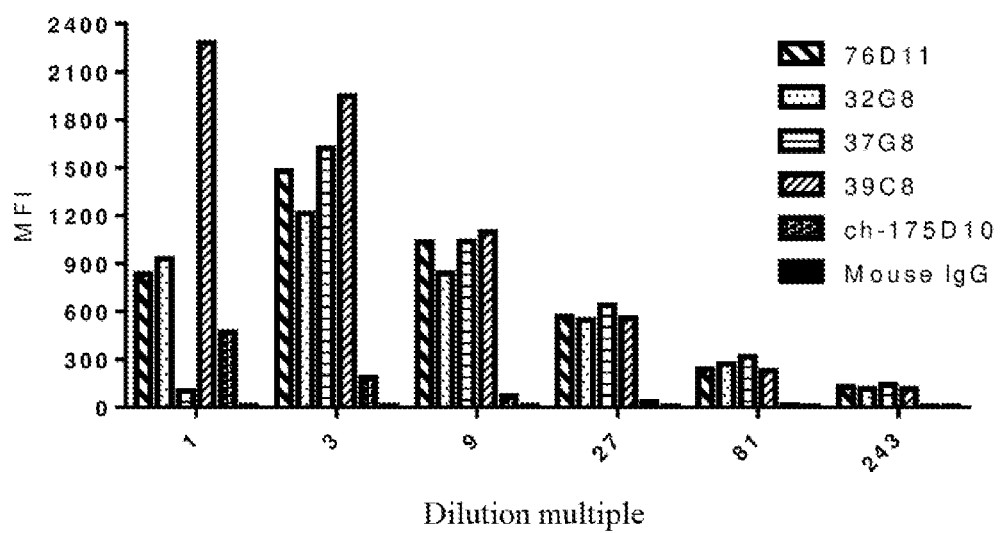
Figure 3:
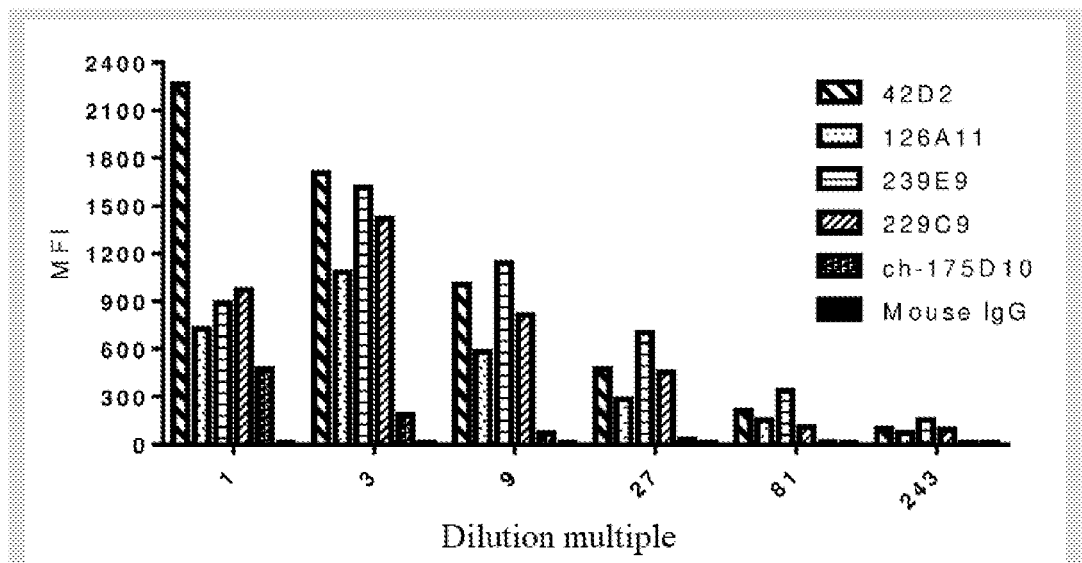
Figure 4:
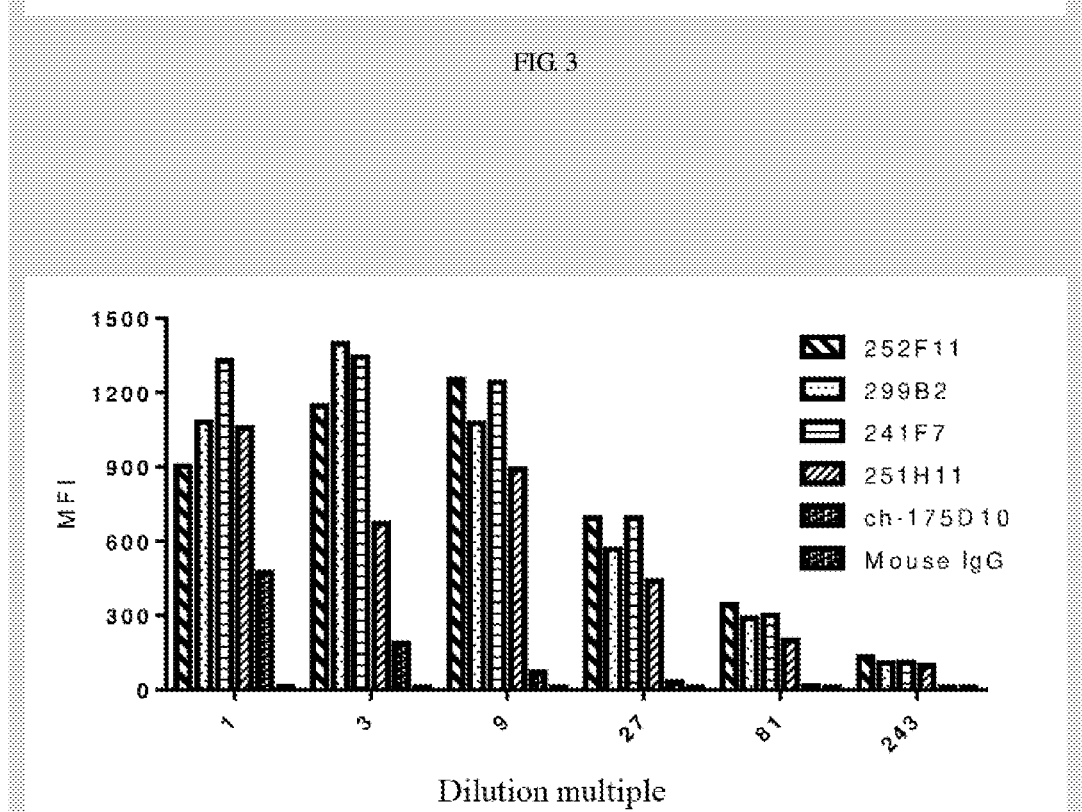
Figure 5:
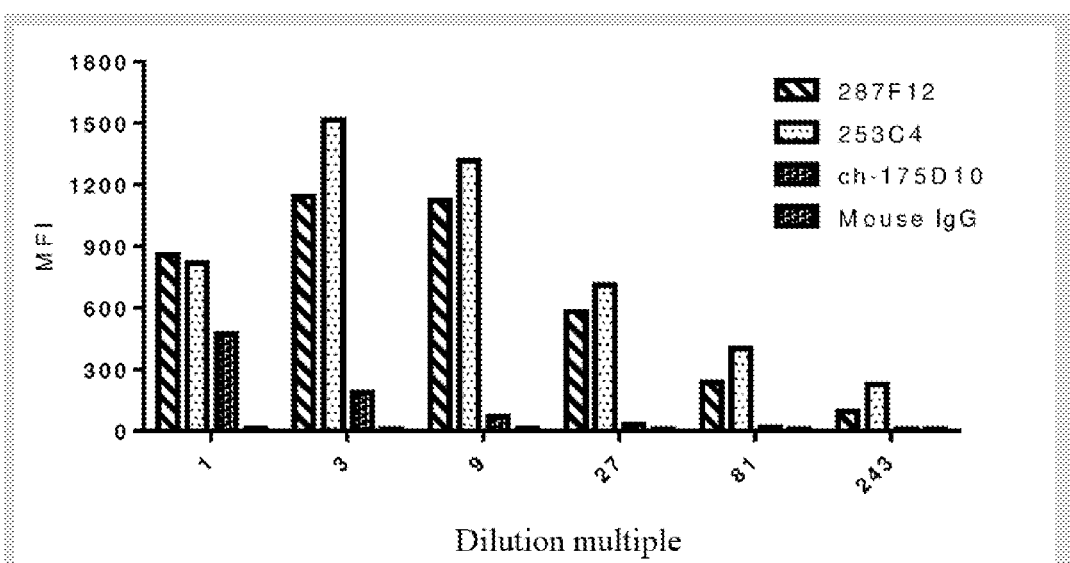
Figure 6:
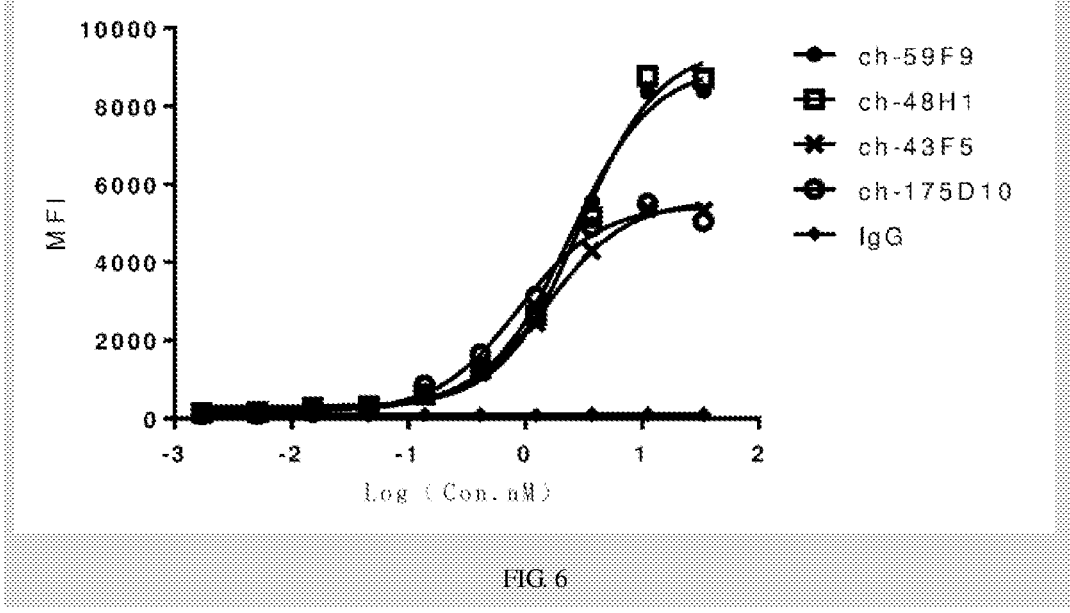
FIGS. 6-11 show the binding of 18 chimeric antibodies of the present disclosure to HEK293 cells stably transfected expressing hCLDN18.2.
Figure 7:
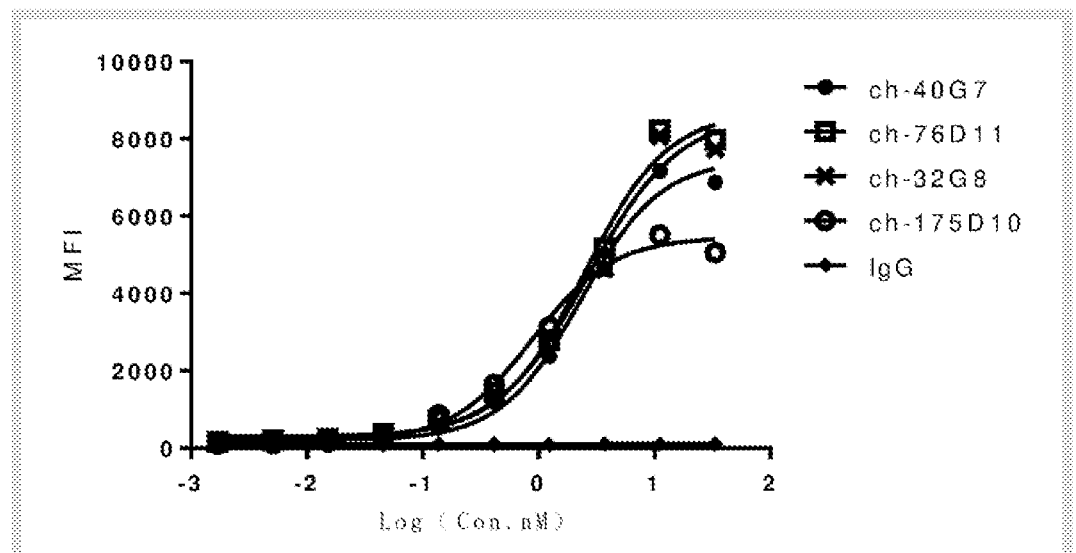
Figure 8:
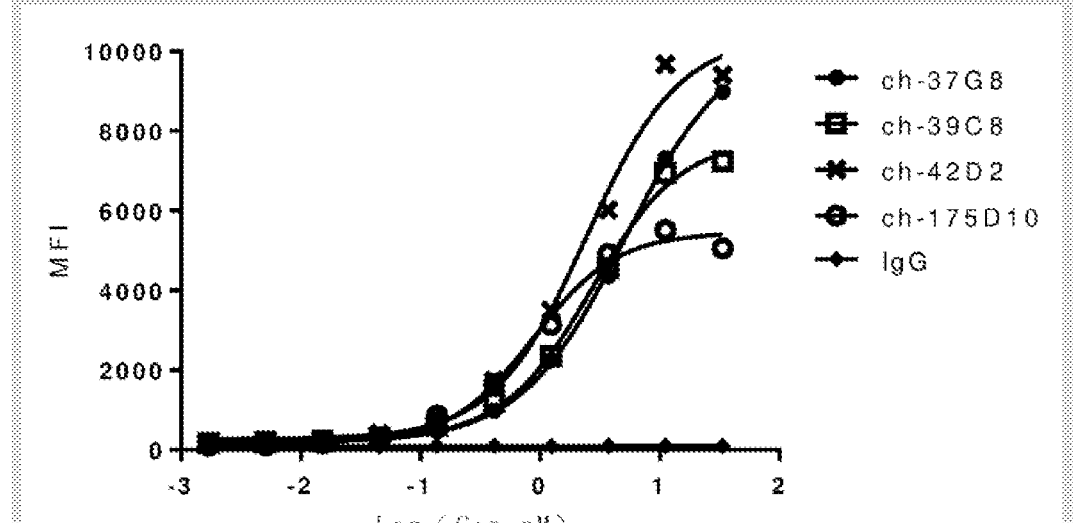
Figure 9:
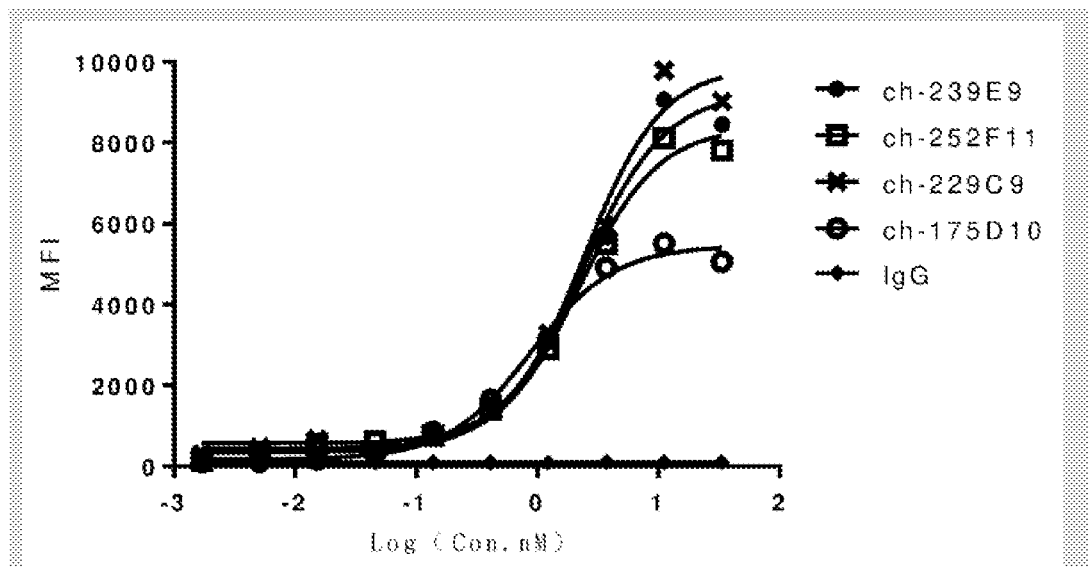
Figure 10:
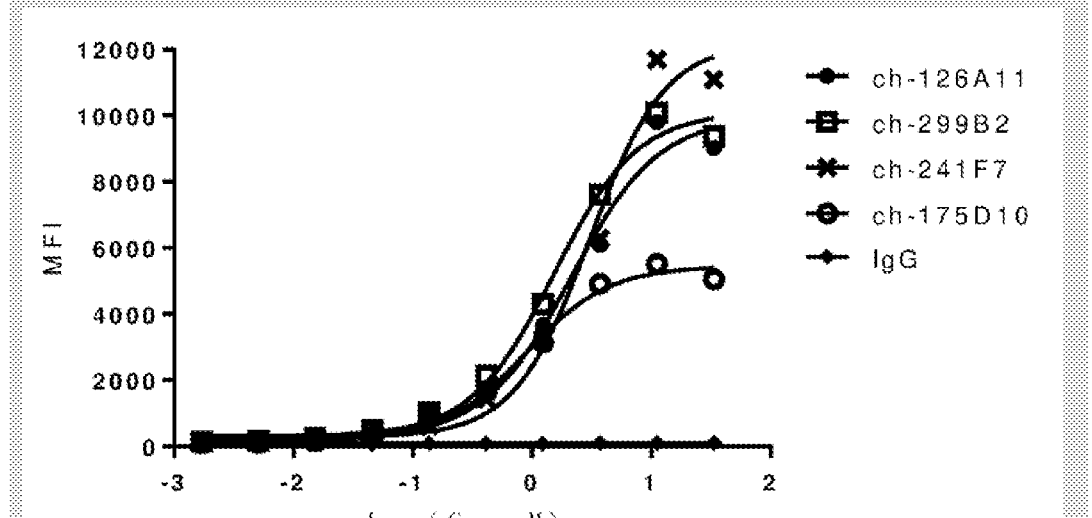
Figure 11:
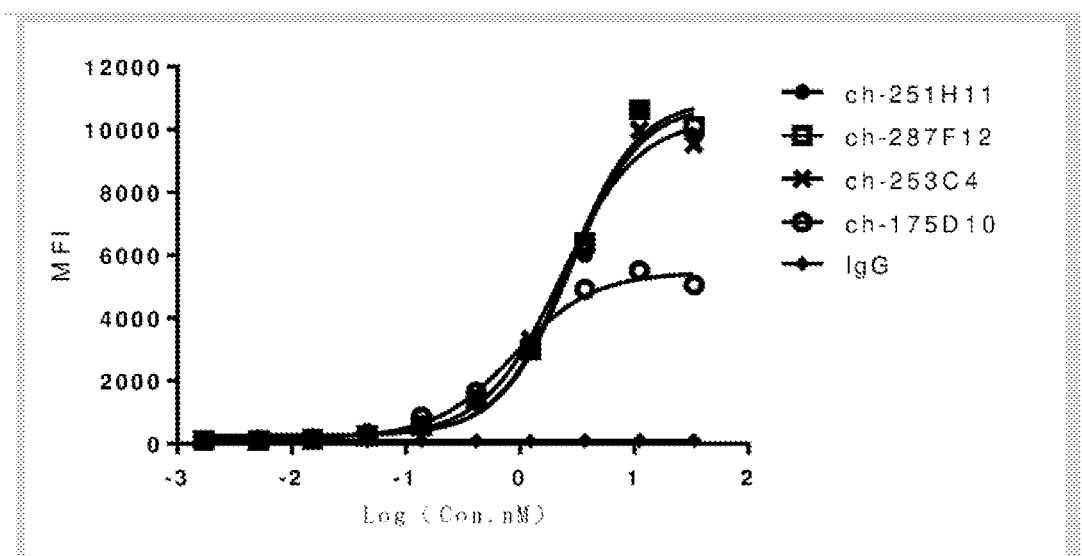
Figure 12:
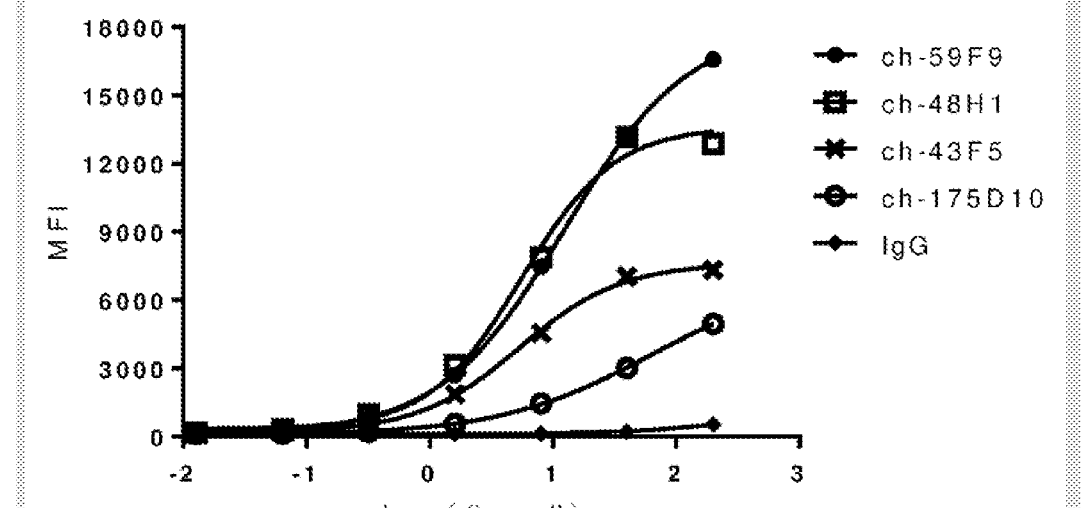
FIGS. 12-17 show the binding of 18 chimeric antibodies of the present disclosure to gastric cancer tumor tissue-derived cells that naturally express hCLDN18.2.
Figure 13:
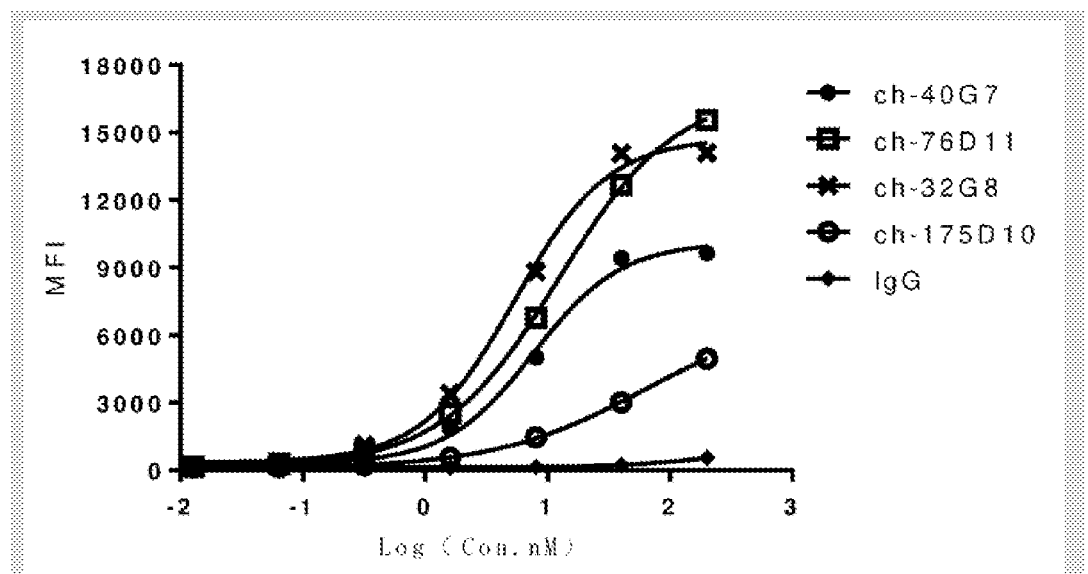
Figure 14:
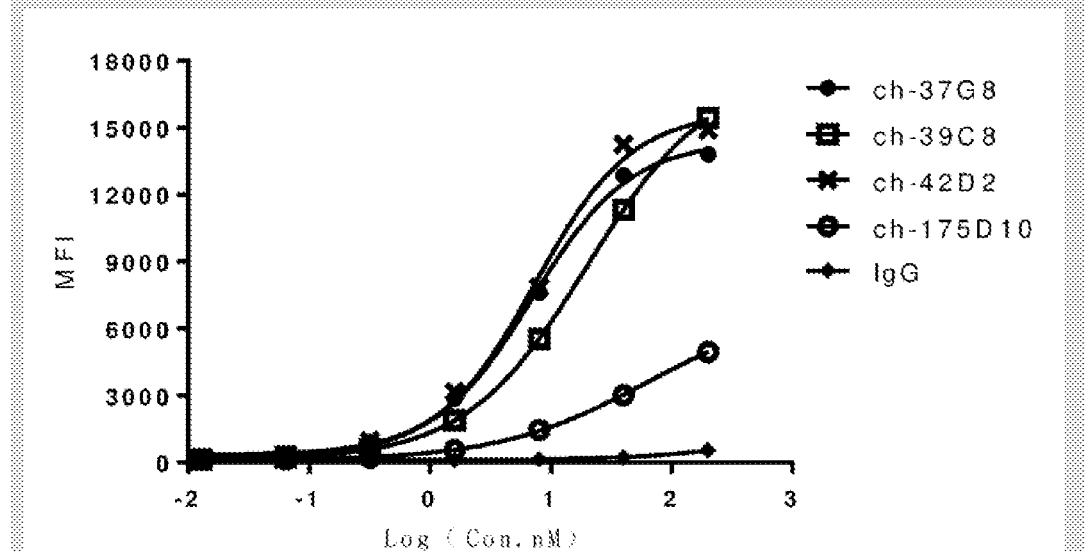
Figure 15:
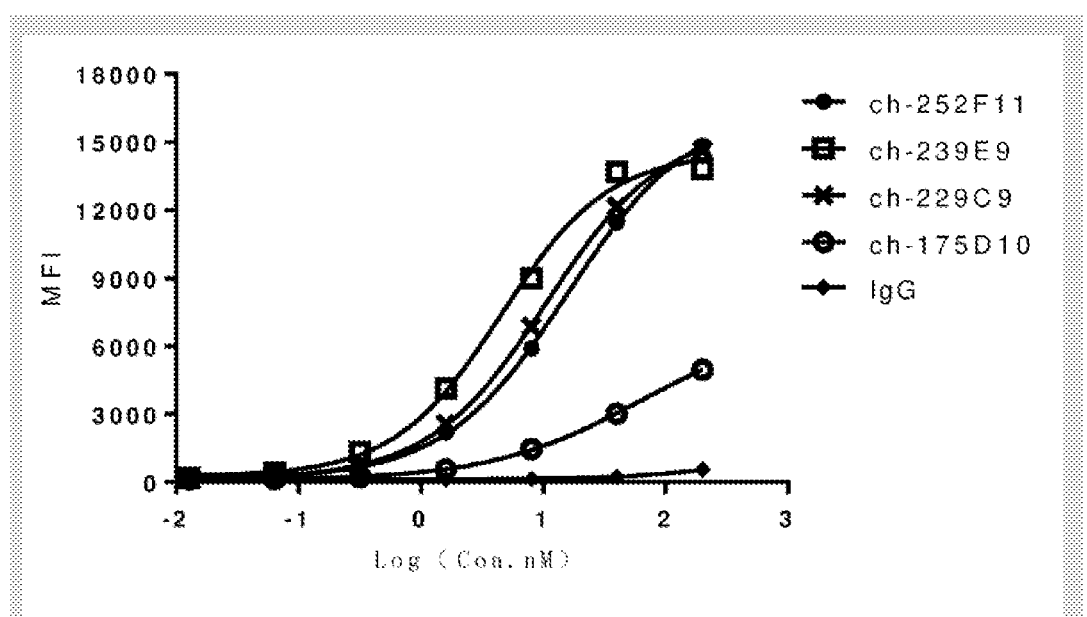
Figure 16:
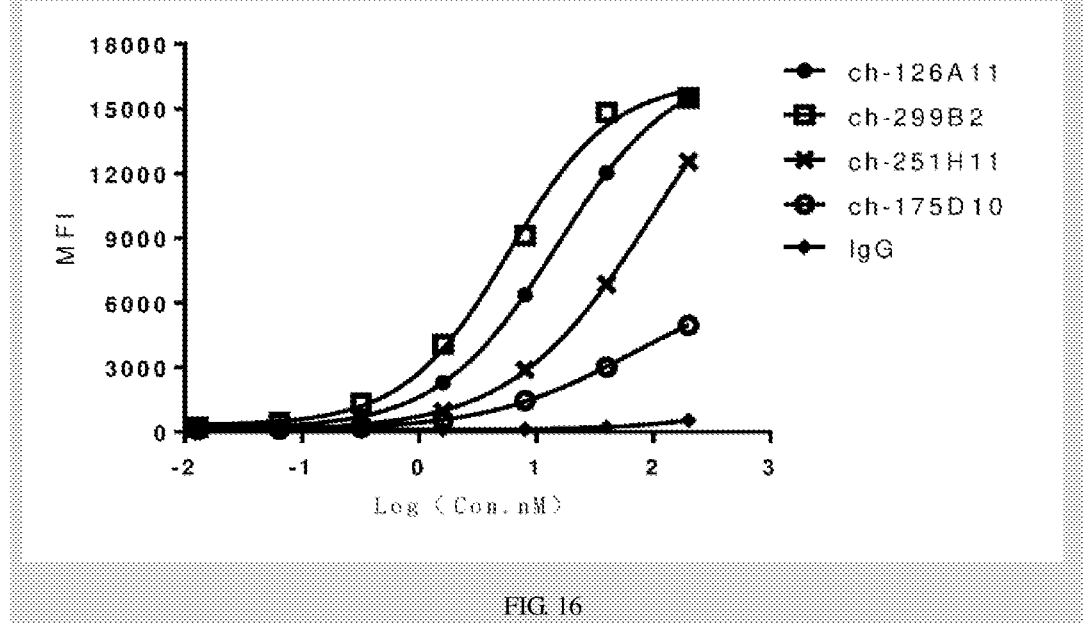
Figure 17:
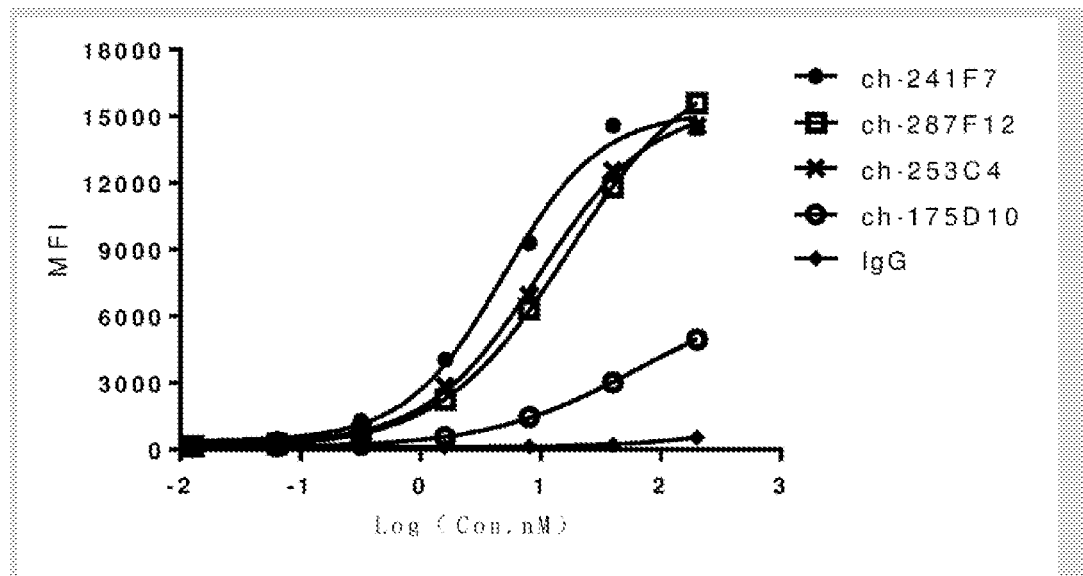
Figure 18:
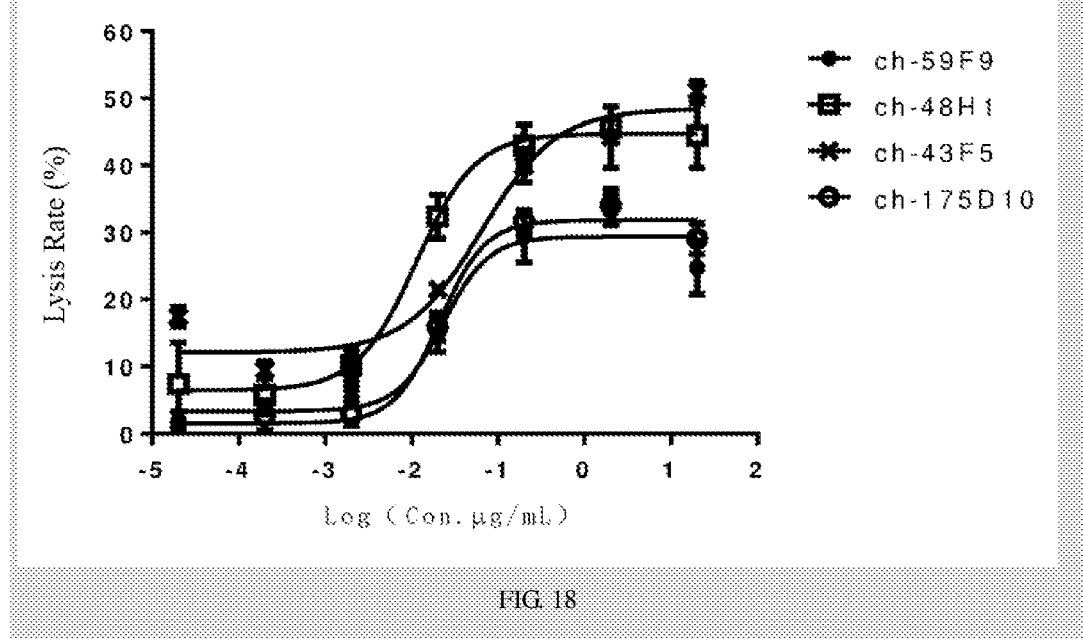
FIGS. 18-23 show ADCC results of 18 chimeric antibodies of the present disclosure against CHO-K1 cells stably transfected expressing hCLDN18.2.
Figure 19:
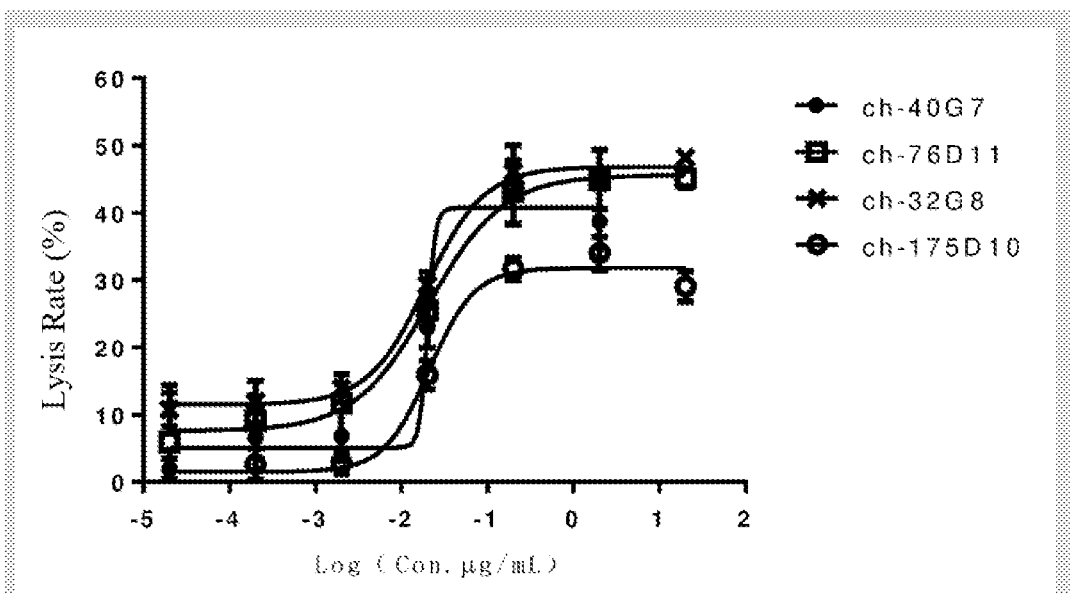
Figure 20:
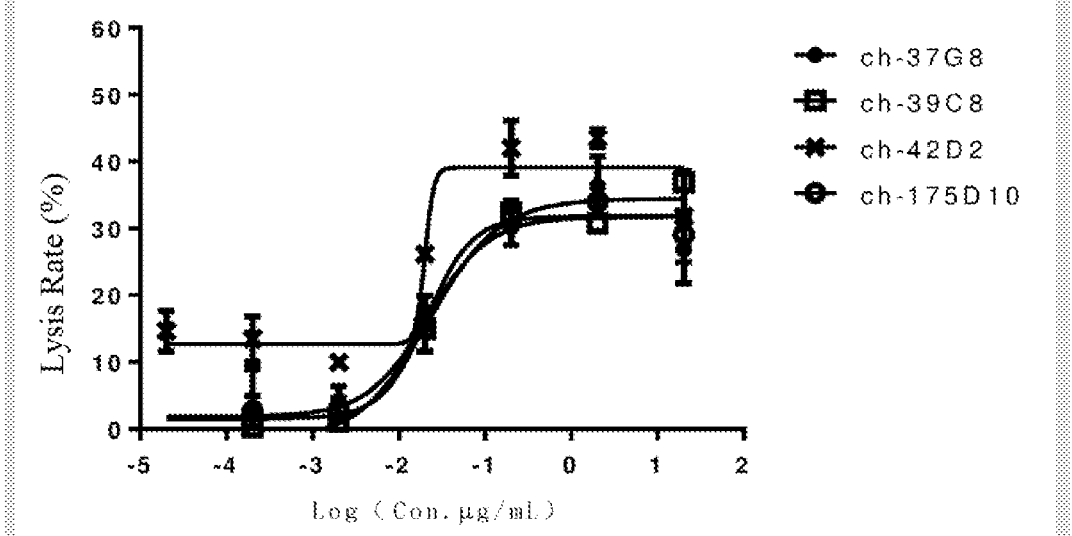
Figure 21:
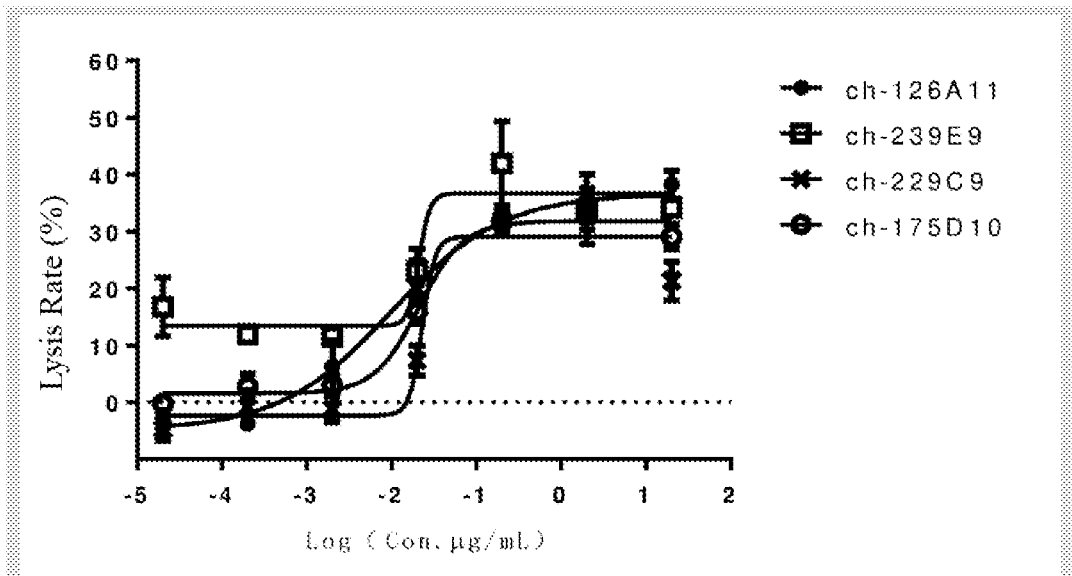
Figure 22:
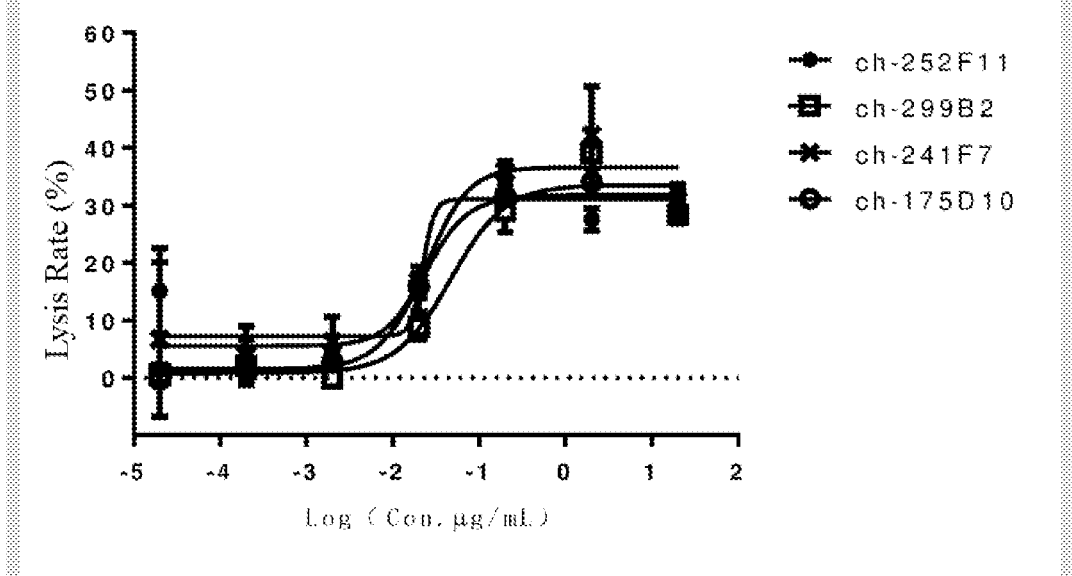
Figure 23:
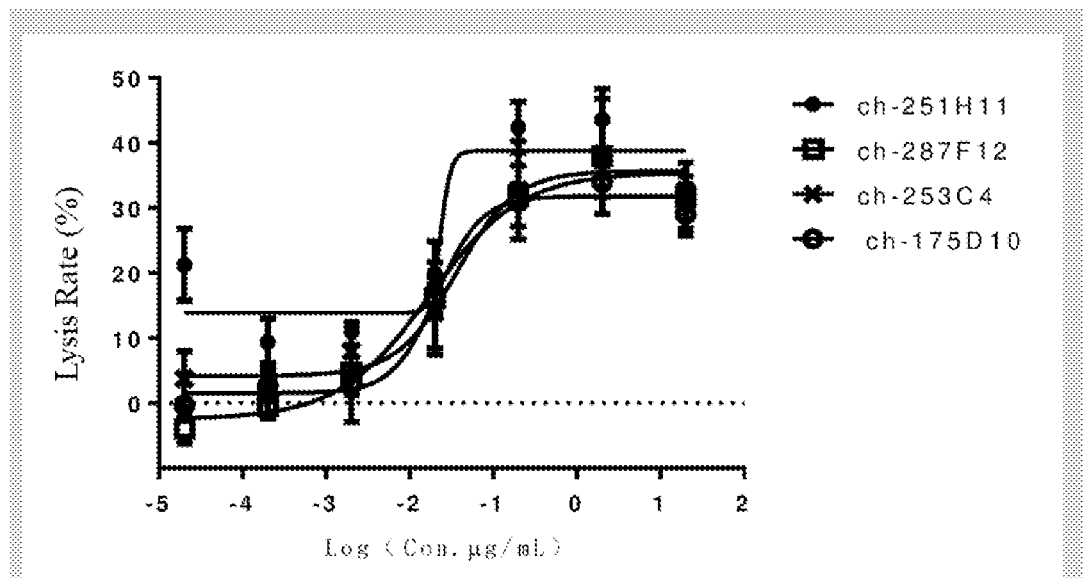
Figure 24:
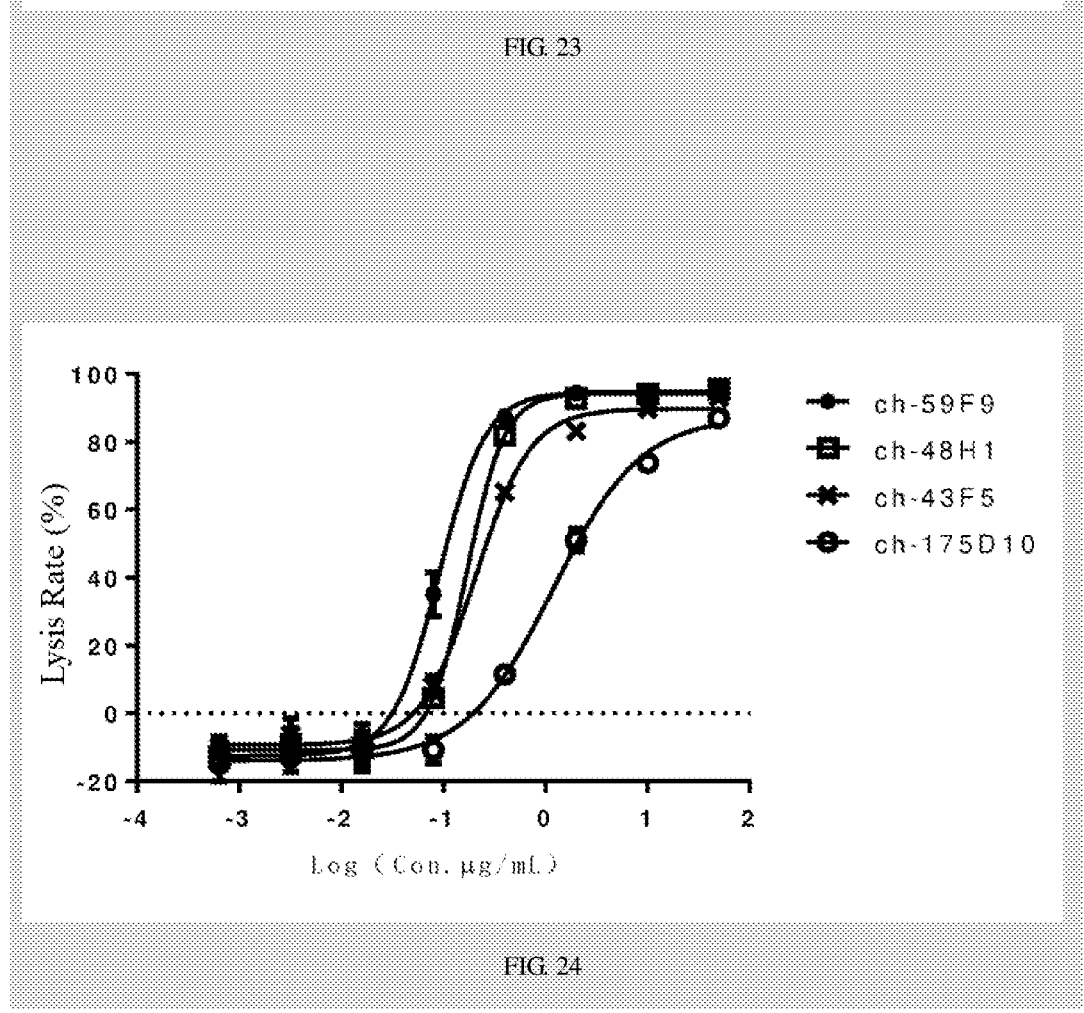
FIGS. 24-29 show CDC results of 18 chimeric antibodies of the present disclosure against CHO-K1 cells stably transfected expressing hCLDN18.2.
Figure 25:
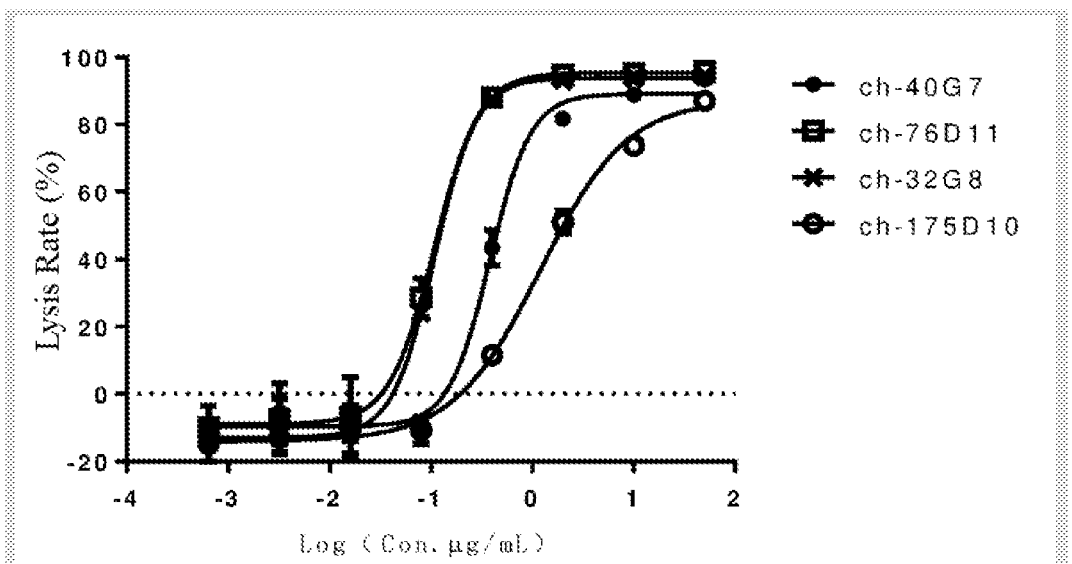
Figure 26:
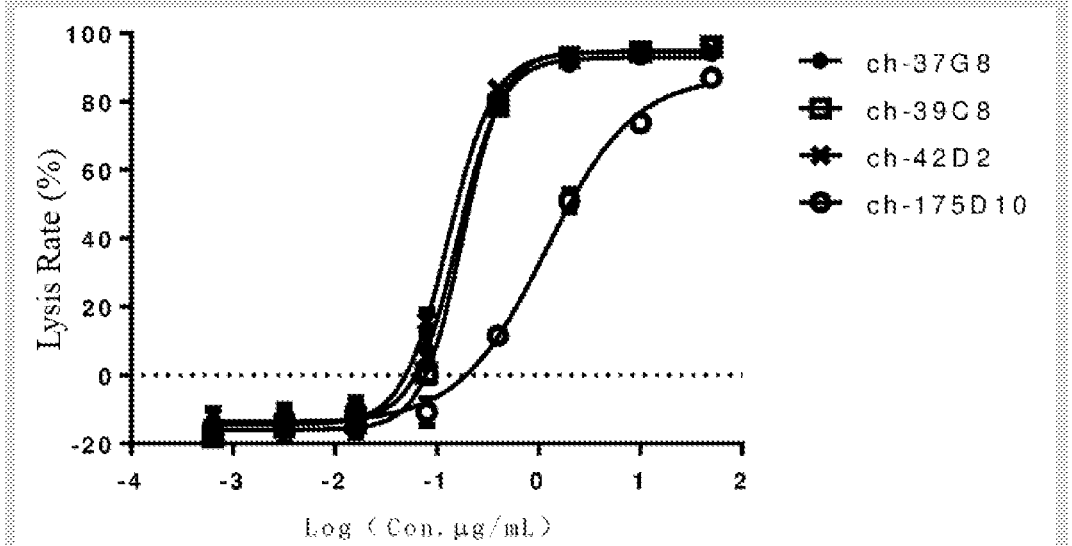
Figure 27:
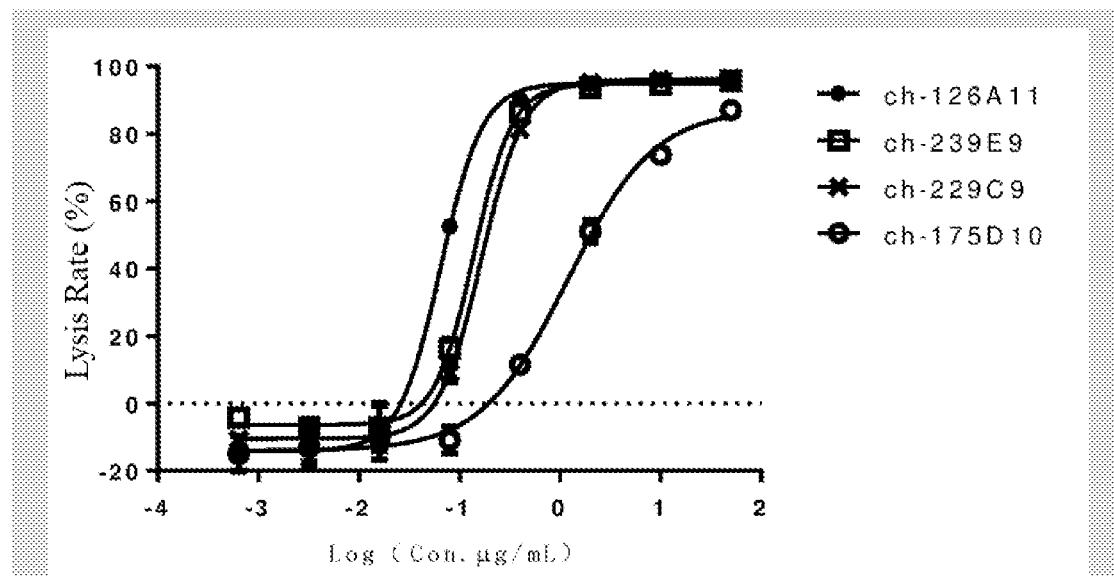
Figure 28:
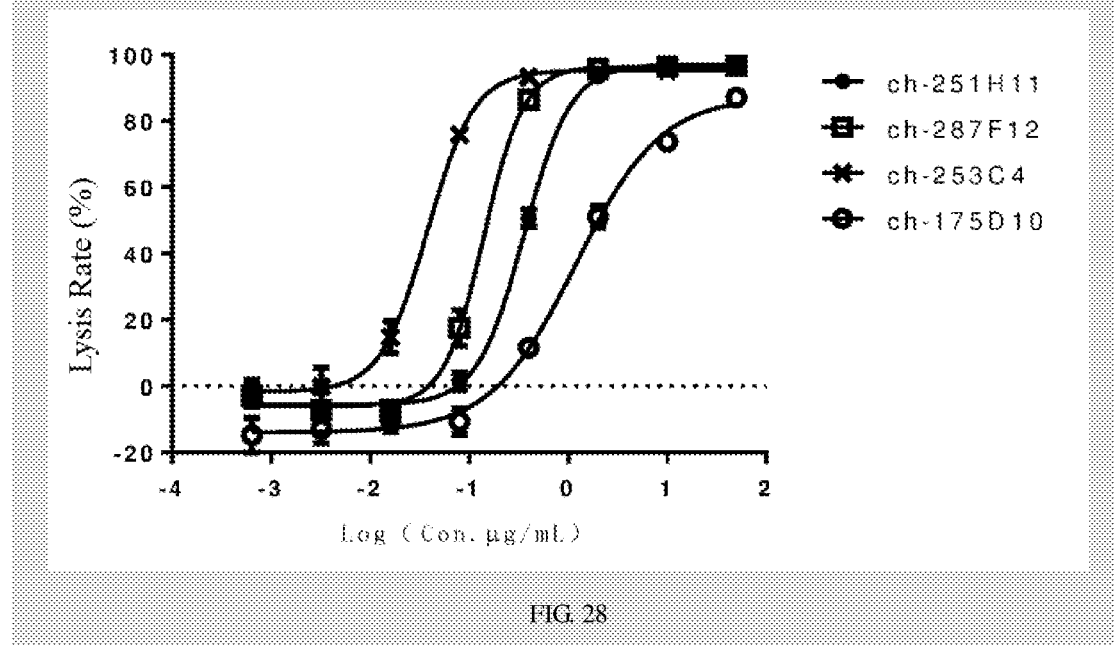
Figure 29:
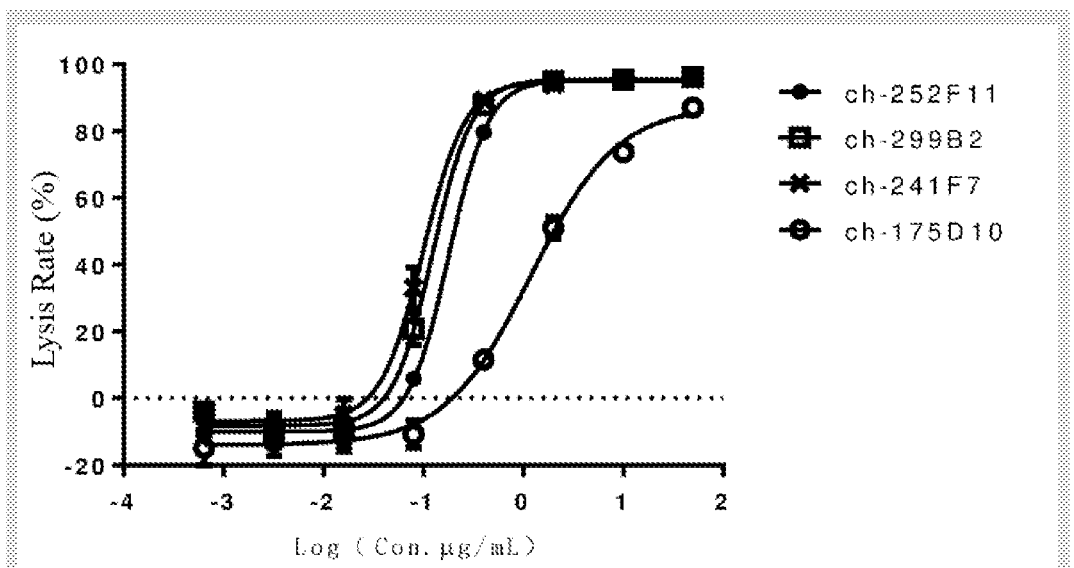
Figure 30:
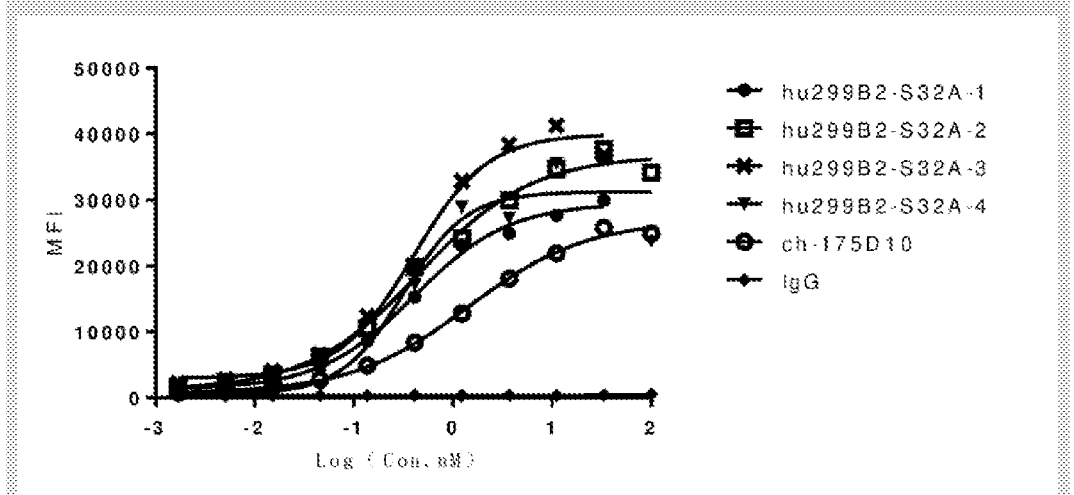
FIG. 30 shows the binding of the humanized antibody hu299B2-S32A of the present disclosure to HEK293 cells stably transfected expressing hCLDN18.2.
Figure 31:
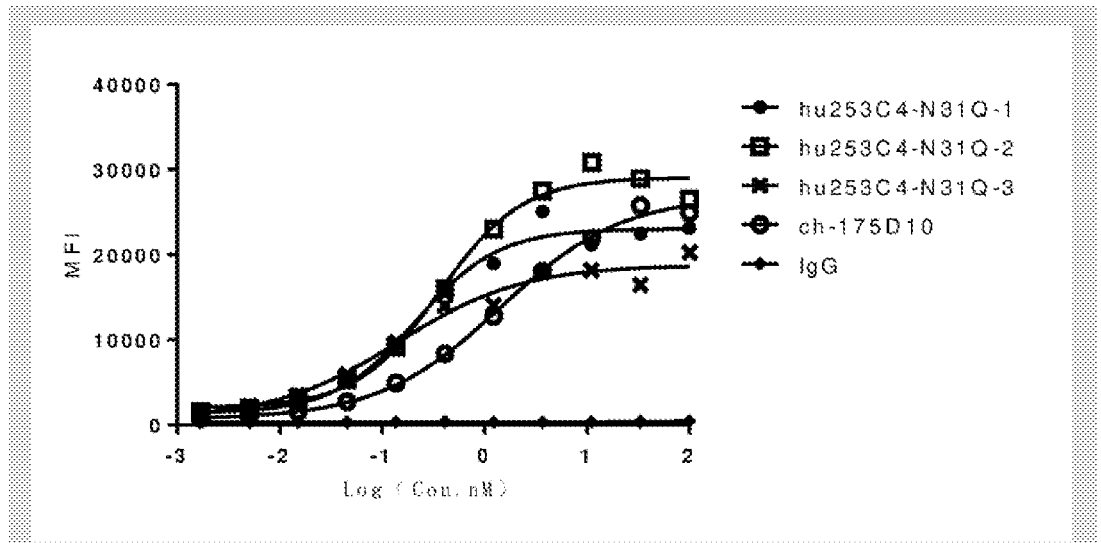
FIG. 31 shows the binding of the humanized antibody hu253C4-N31Q of the present disclosure to HEK293 cells stably transfected expressing hCLDN18.2.
Figure 32:
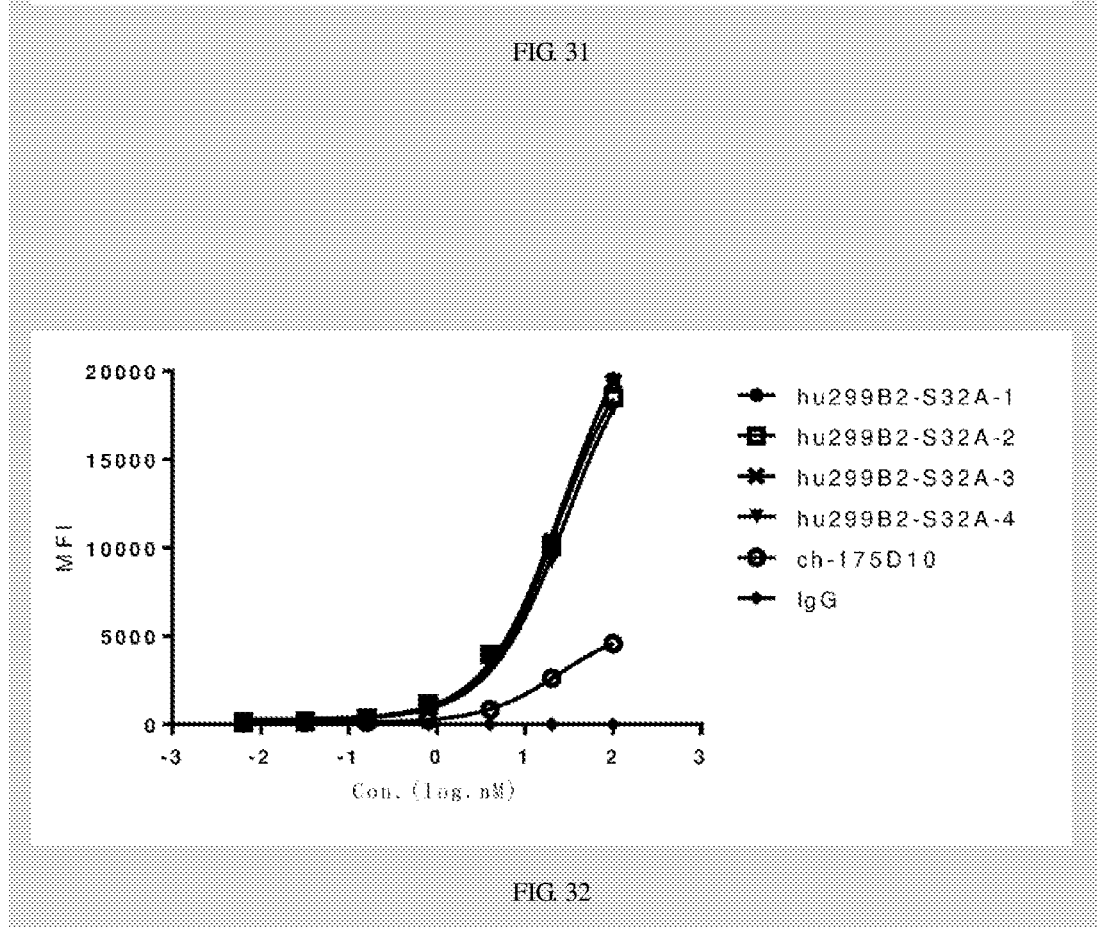
FIG. 32 shows the binding of the humanized antibody hu299B2-S32A of the present disclosure to gastric cancer tumor tissue-derived cells naturally expressing hCLDN18.2.
Figure 33:
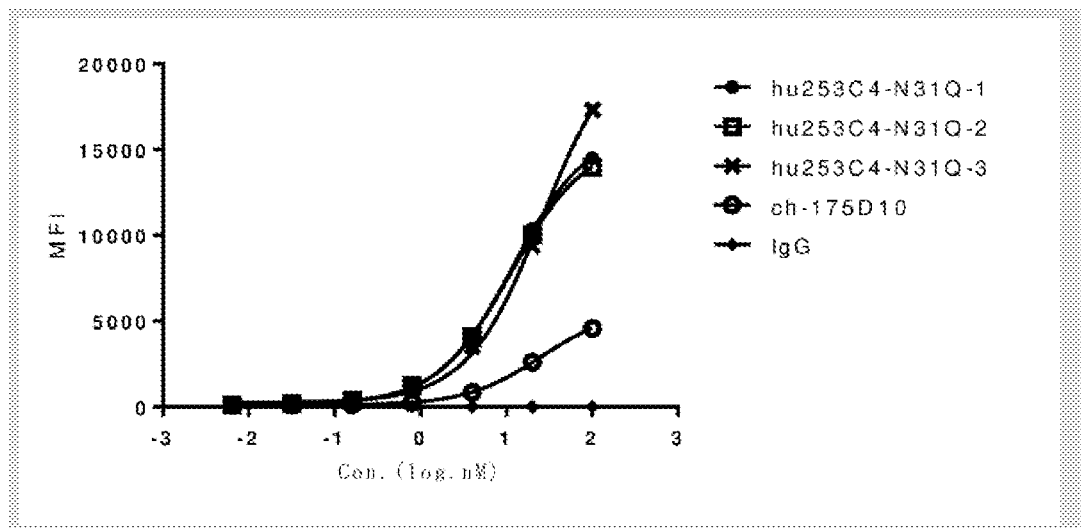
FIG. 33 shows the binding of the humanized antibody hu253C4-N31Q of the present disclosure to gastric cancer tumor tissue-derived cells naturally expressing hCLDN18.2.

All publications, patents, and patent applications mentioned in this specification are herein incorporated by reference to the same extent as if each publication, patent, or patent application was specifically and individually indicated to be incorporated by reference.

Before the present disclosure is described in detail below, it is to be understood that the present disclosure is not limited to the particular methodology, protocols, and reagents described herein, as these may vary. It is also to be understood that the terms used herein are to describe particular embodiments only, and are not intended to limit the scope of the present disclosure. Unless otherwise specified, all technical and scientific terms used herein have the same meanings as those generally understood by a person skilled in the art to which the present disclosure belongs.

Certain embodiments disclosed herein encompass numerical ranges, and certain aspects of the present disclosure may be described in terms of ranges. Unless otherwise indicated, it is to be understood that numerical ranges or descriptions of ranges are merely for brevity and convenience and should not be construed as strictly limiting the scope of the present disclosure. Accordingly, the description in a range format should be taken to specifically disclose all possible subranges and all possible specific numerical points within that range, as such subranges and numerical points are expressly written herein. For example, a description of a range from 1 to 6 should be considered to specifically disclose subranges from 1 to 3, 1 to 4, 1 to 5, 2 to 4, 2 to 6, 3 to 6, etc., as well as specific numerical points within these ranges, e.g., 1, 2, 3, 4, 5, 6. The above principles are equally applicable regardless of the width of the numerical values. Where a range description is employed, the range includes the endpoints of the range.

The term "about" when referring to a measurable value such as an amount and temporal duration, refers to a change that includes ±20%, or in some cases ±10%, or in some cases ±5%, or in some cases ±1%, or in some cases ±0.1% of the specified value.

Amino acid three-letter codes and one-letter codes as used herein are as described in J. Biol. Chem, 243, p3558(1968).

As used herein, the terms "antibody of anti-Claudin18.2", "anti-CLDN18.2 antibody", or "antibody against CLDN18.2" refers to such an antibody that is capable of binding to the CLDN18.2 protein or fragment thereof with sufficient affinity such that the antibody can be used as a diagnostic and/or therapeutic agent that targets CLDN18.2. The human-derived CLDN18.2 protein is designated hCLDN18.2, thus, "antibody of anti-human Claudin18.2", "anti-human Claudin18.2 antibody", "antibody of anti-hCLDN18.2", "anti-hCLDN18.2 antibody", "antibody against hCLDN18.2" in particular to refers to such an antibody that is capable of binding to the human CLDN18.2 protein or fragment thereof with sufficient affinity such that the antibody can be used as a diagnostic and/or therapeutic agent that targets human CLDN18.2.

The term "antibody", as used herein, typically refers to a Y-type tetrameric protein comprising two heavy (H) polypeptide chains and two light (L) polypeptide chains held together by covalent disulfide bonds and non-covalent interactions. Native IgG antibodies have this structure. Each light chain consists of one variable domain (VL) and one constant domain (CL). Each heavy chain comprises one variable domain (VH) and a constant region.

As known in the art, the heavy chain constant domains may be classified into α, δ, ε, γ and μ which define isotypes of an antibody as IgA, IgD, IgE, IgG, and IgM, respectively; and IgG and IgA may be further classified into different subclasses, wherein IgG may be subdivided into for example IgG1, IgG2, IgG3, and IgG4, and IgA may be subdivided into IgA1 and IgA2. The light chains of antibodies from any vertebrate species can be assigned to one of two distinct types, called κ and λ, based on the amino acid sequences of their constant domain. In IgG, IgA, and IgD, the constant region comprises three domains called CH1, CH2, CH3 (IgM and IgE have the fourth domain called CH4). In IgG, IgA, and IgD, the CH1 and CH2 domains are separated by a flexible hinge region, which is a proline-rich and cysteine-rich segment of variable length. Each type of antibody further comprises interchain and intrachain disulfide bonds formed by paired cysteine residues.

The term "variable region" or "variable domain" shows a significant change in amino acid composition from one antibody to another and is primarily responsible for antigen recognition and binding. The variable region of each light/heavy chain pair forms an antibody binding site such that the intact IgG antibody has two binding sites (i.e., it is bivalent).

Variable region of heavy chain (VH) and variable region of light chain (VL) each comprise three regions of extreme variability, which are termed hypervariable regions (HVR), or more generally, complementarity-determining regions (CDRs), VH and VL each have four framework regions (FRs), which are represented by FR1, FR2, FR3, and FR4, respectively, Thus, CDR and FR sequences typically occur in the following sequences of variable region of heavy chain (VH) (or variable region of light chain (VL)): FR1-HCDR1 (LCDR1)-FR2-HCDR2(LCDR2)-FR3-HCDR3(LCDR3)-FR4.

The term "Fc" is used herein to define the C-terminal region of an immunoglobulin heavy chain comprising at least a portion of a constant region. This term includes native sequence Fc regions and variant Fc regions. Unless otherwise indicated, the numbering of amino acid residues in the Fc region or constant region is according to the EU numbering system, which is also referred to as the EU index, as described in Kabat et al., Sequences of Proteins of Immunological Interest, 5th Ed. Public Health Service, National Institutes of Health, Bethesda, MD, 1991.

As used herein, the types of "antibodies" in a broad sense may include, for example, polyclonal antibodies, monoclonal antibodies, chimeric antibodies, humanized and primatized antibodies, CDR-grafted antibodies, human antibodies (including recombinantly produced human antibodies), recombinantly produced antibodies, intracellular antibodies, multispecific antibodies, bispecific antibodies, monovalent antibodies, multivalent antibodies, anti-idiotypic antibodies, synthetic antibodies (including muteins and variants thereof), etc.

The terms "full-length antibody" and "intact antibody" are used interchangeably herein to refer to an antibody having a structure substantially similar to that of a native antibody structure or having an Fc region.

The term "monoclonal antibody" (or "mAb") refers to a substantially homogeneous antibody produced by a single cell clone that is directed against only a particular antigenic epitope. Monoclonal antibodies can be prepared using a variety of techniques known in the art, including hybridoma techniques, recombinant techniques, phage display techniques, transgenic animals, synthetic techniques, or combinations thereof.

The term "chimeric antibody" is a construct in which a portion of the heavy and/or light chain is identical or homologous to a corresponding sequence in an antibody from a particular species or belonging to a particular antibody class or subclass, and the remaining portion of the chain(s) is identical or homologous to a corresponding sequence in an antibody from another species or belonging to another antibody class or subclass, and corresponding sequences in fragments of such antibodies. In a narrow sense, a chimeric antibody comprises all or most of selected murine heavy and light chain variable regions operably linked to human light and heavy chain constant regions. The constant region sequences, or variants or derivatives thereof, may be operatively associated with the disclosed heavy and light chain variable regions using standard molecular biology techniques to provide full-length anti-CLDN18.2 antibodies that may be used themselves or may be incorporated into the present disclosure.

The term "humanized antibody" is a hybrid immunoglobulin, immunoglobulin chain or fragment thereof that contains the smallest sequence derived from non-human immunoglobulin. In most cases, the humanized antibody is a human immunoglobulin (recipient antibody) in which residues from CDRs of the recipient are replaced by residues from CDRs of a non-human species (donor antibody) having the desired specificity, affinity, and properties, such as mice, rats, rabbits or primates. In some cases, the framework residues of a human immunoglobulin are replaced with corresponding non-human residues. In some cases, "back mutations" may be introduced into humanized antibodies in which residues in one or more FRs of the variable region of the recipient human antibody are replaced with corresponding residues from a non-human species donor antibody. Such back mutations may help maintain the proper three-dimensional configuration of one or more grafted CDRs, thus improving affinity and antibody stability. Antibodies from a variety of donor species including, but not limited to, mice, rats, rabbits, or non-human primates may be used. In addition, humanized antibodies may contain new residues not found in the recipient antibody or the donor antibody to further improve antibody performance.

It is noted that the divisions of CDR and FR in the variable regions of the monoclonal antibodies of the present disclosure are determined according to the Kabat definition. However, other naming and numbering systems, such as Chothia, IMGT, or AHo, are also known to those skilled in the art. Thus, humanized antibodies comprising one or more CDRs derived from any nomenclature system, based on the monoclonal antibody sequences of the present disclosure, are expressly maintained within the scope of the present disclosure.

The term "sequence identity" or "sequence similarity" or "sequence homology" refers to the percentage of amino acid residues in a candidate sequence that is identical to the same amino acid residues in a reference polypeptide sequence after the sequences are aligned (and gaps are introduced when necessary) to achieve the maximum percent sequence identity, and any conservative substitutions are not considered as part of the sequence identity.

Sequence alignments can be performed using various approaches in the art to determine percent amino acid sequence identity, for example, using publicly available computer software such as BLAST, BLAST-2, ALIGN, or MEGALIGN (DNASTAR) software. Those skilled in the art can determine the appropriate parameters for the measurement alignment, including any algorithm required to achieve the maximum alignment over the full length of the sequence being compared.

The term "antibody fragment" encompasses at least a portion of an intact antibody. As used herein, a "fragment" of an antibody molecule includes an "antigen-binding fragment" of an antibody, and the term "antigen-binding fragment" refers to a polypeptide fragment of an immunoglobulin or antibody that specifically binds to or reacts with a selected antigen or antigenic epitope thereof, or a fusion protein product further derived from the fragment, e.g., a single-chain antibody, an extracellular binding region in a chimeric antigen receptor, etc. Exemplary antibody fragments or antigen-binding fragments thereof include but are not limited to light chain variable fragments (VL), heavy chain variable fragments (VH), Fab fragments, F(ab')$_2$ fragments, Fd fragments, Fv fragments, single domain antibodies, linear antibodies, single-chain antibodies (scFv), and bispecific antibodies or multispecific antibodies formed from antibody fragments, etc.

The term "Fab fragment" includes a variable region of each of the heavy and the light chain, and also includes a constant region of the light chain and a first constant region CH1 of the heavy chain, which is a monovalent antibody fragment. The term "F(ab')₂ fragment" encompasses two Fab fragments as well as hinge regions, which is a bivalent antibody fragment.

The term "Fd fragment" generally encompasses a heavy chain variable region and a constant region CH1; the term "Fv fragment" is the smallest antibody fragment having variable regions of heavy chain and light chain, but no constant region, and holding all antigen-binding sites.

The term "scFv" refers to a fusion protein comprising at least one antibody fragment including the variable region of the light chain and at least one antibody fragment including the variable region of the heavy chain, wherein the variable regions of the light and heavy chain are connected (e.g., via a synthetic linker such as a short flexible polypeptide linker) and capable of being expressed as a single-chain polypeptide, and wherein the scFv retains the specificity of the intact antibody from which it is derived. Unless otherwise specified, an scFv may have the VL and VH variable regions described in any order (e.g., relative to the N-terminus and C-terminus of the polypeptide), and scFv may comprise a VL-linker-VH or may comprise a VH-linker-VL.

The term "multispecific antibody" refers to a novel antibody construct binding to more than two different sites and/or targets, which is formed by functionally linking (e.g., chemical coupling, gene fusion, non-covalent binding, or other methods) the antibody to one or more other binding molecules. The more common multispecific antibody is the "bispecific antibody", which specifically refers to an antibody construct with specificities for two different antigens. Typically, a bispecific or multispecific antibody comprises at least two antigen-binding domains.

The term "antigen" refers to a substance recognized and specifically bound by an antibody or antibody-binding fragment, and broadly, an antigen can include any immunogenic fragment or determinant of a selected target, including a single epitope, a multi-epitope, a single domain, multiple domains, or an entire extracellular domain (ECD) or a protein. Peptides, proteins, glycoproteins, polysaccharides and lipids, portions thereof, and combinations thereof may constitute antigens. Non-limiting exemplary antigens include tumor antigens or pathogen antigens, etc. "Antigen" may also refer to a molecule that triggers an immune response. Any form of antigens or cells or preparations containing the antigens may be used to generate antibodies specific for an antigenic determinant. The antigen can be an isolated full-length protein, a cell surface protein (e.g., immunized with a cell expressing at least a portion of the antigen on its surface), or a soluble protein (e.g., immunized with only the ECD portion of the protein), or a protein construct (e.g., an Fc antigen). The antigen may be produced in genetically modified cells. Any of the foregoing antigens may be used alone or in combination with one or more immunogenicity-enhancing adjuvants known in the art. The DNA encoding the antigen may be genomic or non-genomic (e.g., cDNA) and may encode at least a portion of the ECD sufficient to trigger an immunogenic response. Any vector may be used to transform cells in which the antigen is expressed, including but not limited to adenoviral vectors, lentiviral vectors, plasmids, and non-viral vectors such as cationic lipids.

The term "epitope" refers to a site on an antigen that specifically binds to an immunoglobulin or antibody. Epitopes may be formed from contiguous amino acids or noncontiguous amino acids juxtaposed by the tertiary folding of a protein. Epitopes formed from contiguous amino acids are typically retained upon exposure to denaturing solvents, while epitopes formed by tertiary folding are typically lost upon treatment with denaturing solvents. Epitopes typically comprise at least 3-15 amino acids in a unique spatial conformation. Methods for determining the epitope to which a given antibody binds are well known in the art, including immunoblotting and immunoprecipitation detection assays. Methods for determining the spatial conformation of an epitope include techniques in the art and described herein, such as X-ray crystallography, two-dimensional nuclear magnetic resonance, etc.

The terms "polypeptide", "peptide", and "protein" are used interchangeably herein to refer to polymers of amino acids of any length. The polymer may be linear, cyclic or branched, and may comprise modified amino acids, particularly conservatively modified amino acids, and it may be interrupted by non-amino acids. The term also includes modified amino acid polymers such as amino acid polymers that have been modified by sulfation, glycosylation, lipidation, acetylation, phosphorylation, iodination, methylation, oxidation, proteolytic processing, prenylation, racemization, selenoylation, transfer RNA (tRNA)-mediated amino addition such as arginylation, ubiquitination, or any other operation such as conjugation to a labeling component. As used herein, the term "amino acid" refers to natural and/or non-natural or synthetic amino acids, including glycine and D or L optical isomers, as well as amino acid analogs and peptidomimetics. A polypeptide or amino acid sequence "derived from" a given protein refers to the source of the polypeptide. The term also includes polypeptides expressed from the specified nucleic acid sequences.

The term "amino acid modification" (or "modified amino acid") includes amino acid substitutions, insertions, and/or deletions in a polypeptide sequence. As used herein, "amino acid substitution" or "substitution" refers to the replacement of an amino acid at a particular position in a parent polypeptide sequence with another amino acid. For example, substitution S32A means that serine at position 32 is replaced with alanine.

Sequence identity or homology of a humanized antibody variable region to a human receptor variable region can be determined as discussed herein, and when measured in this way, the two will preferably share at least 60% or 65% sequence identity, more preferably at least 70%, 75%, 80%, 85% or 90% sequence identity, even more preferably at least 93%, 95%, 98% or 99% sequence identity. Preferably, residue positions that are not identical differ by conservative amino acid substitutions. A "conservative substitution" is an amino acid substitution in which one amino acid residue is replaced with another amino acid residue having a side chain (R group) with similar chemical properties (e.g., charge or hydrophobicity). In general, conservative amino acid substitutions do not substantially alter the functional properties of the protein. Families of amino acid residues having similar side chains have been defined in the art. These families include amino acids containing basic side chains (e.g., lysine, arginine, histidine), acidic side chains (e.g., aspartic acid, glutamic acid), uncharged polarside chains (e.g., glycine, asparagine, serine, threonine, tyrosine, cysteine, tryptophan), non-polar side chains (e.g., alanine, valine, leucine, isoleucine, proline, phenylalanine, methionine), B branched side chains (e.g., threonine, valine, isoleucine), and aromatic side chains (e.g., tyrosine, phenylalanine, tryptophan, histidine). Thus, one or more amino acid residues in the CDR regions or the framework regions of the antibodies of the present disclosure may be replaced with amino acid residues of other similar side chains. In the case where two or more amino acid sequences differ from one another by conservative substitutions, the percent sequence identity or degree of similarity may be adjusted upward to correct for the conservative nature of the substitution.

In the production of monoclonal antibodies, various post-translational modifications (PTM) variants, such as glycosylation, oxidation, saccharification, deamidation, isomerization, and end-group cyclization, are easily produced by different physical and chemical factors. These PTMs may cause changes in the physical and chemical properties of the antibody, alter the interaction with the Fc receptor of the antibody, and affect the binding activity with the target antigen; the occurrence of some PTMs may even reduce antibody stability, cause immunogenicity, etc. (JARASCH et al., JOURNAL OF PHARMACEUTICAL SCIENCES, 2015). Negative effects can be eliminated by amino acid modifications, such as conservative substitutions, to the PTM site.

Amino acid substitutions to antibody CDRs to modify PTM also expressly maintained within the scope of the present disclosure.

The term "antibody-dependent cell-mediated cytotoxicity" (ADCC) refers to the binding of an antibody to an epitope of a virus-infected cell or tumor cell, wherein Fc fragment binds to Fc receptors (FcRs) present on killer cells (NK cells, and macrophages, etc.) to mediate the killer cells to directly kill target cells.

The term "complement-dependent cytotoxicity" (CDC) refers to the cytotoxic effect in the presence of complement, i.e. the lysis of target cells by membrane attack complex formed by activation of the classical complement pathway, which is initiated by complex formed by the binding of specific antibodies to corresponding membrane surface antigens.

Antibodies of the present disclosure may also include substitutions or modifications of constant regions (e.g., Fc), including, but not limited to, amino acid residue substitutions, mutations, and/or modifications, which result in compounds having the following preferred characteristics, including, but not limited to: altered pharmacokinetics, increased serum half-life, increased binding affinity, decreased immunogenicity, increased yield, altered Pc ligand binding to Pc receptors (FcRs), increased or decreased ADCC or CDC, altered glycosylation and/or disulfide bonds, and modified binding specificity.

The term "affinity" or "binding affinity" refers to the strength of the sum of all non-covalent interactions between a single binding site of a molecule (e.g., an antibody) and its binding partner (e.g., an antigen). The term "$K_D$" refers to the dissociation constant of a particular antibody-antigen interaction. Binding affinities can be determined using various techniques known in the art, such as surface plasmon resonance, bio-layer interferometry, dual-polarization interferometry, static light scattering, dynamic light scattering, isothermal titration calorimetry, ELISA, analytical ultracentrifugation, and flow cytometry, etc.

The term "competitive binding" or "competitive antibody" generally refers to an antibody that binds to the same epitope as the antibody of the present disclosure, the binding of which results in the binding of the antibody of the present disclosure to the epitope to be inhibited or blocked, and the degree of competitive inhibition can be obtained in a competition assay.

The term "pharmaceutical composition" refers to a formulation that is present in a form that allows the biological activity of the active ingredients contained therein to be effective, and which does not contain additional ingredients having unacceptable toxicity to the subject to which the formulation is administered.

The term "pharmaceutically carrier" or "pharmaceutically acceptable carrier" refers to a diluent, adjuvant (e.g., Freund's adjuvant (complete and incomplete)), excipient, or vehicle with which a therapeutic agent is administered.

The term "effective amount" refers to a dose of a pharmaceutical formulation of an antibody or fragment of the present disclosure that, when administered to a patient in single or multiple doses, produces the desired effect in the treated patient. An effective amount can be readily determined by the attending physician, as one skilled in the art, by considering the following factors: for example, the different of human species; body weight, age, and health; specific diseases involved; the severity of the disease; the response of an individual patient; the specific antibody administered; modes of administration; bioavailability characteristics of the administered formulation; a selected dosing regimen; and the use of any concomitant therapy.

The terms "host cell", "host cell line" and "host cell culture" are used interchangeably and refer to a cell into which an exogenous nucleic acid is introduced, including progeny of such a cell. Host cells include "transformants" and "transformed cells", which include primarily transformed cells and progeny derived therefrom, regardless of the number of passages. The progeny may not be exactly the same as the parent cell in nucleic acid content but may contain mutations. Mutant progeny having the same function or biological activity as screened or selected in the initially transformed cell are included herein.

As used herein, the term "transfection" refers to the introduction of an exogenous nucleic acid into a eukaryotic cell. Transfection can be accomplished by various means known in the art, including calcium phosphate-DNA co-precipitation, DEAE-dextran mediated transfection, polybrene-mediated transfection, electroporation, microinjection, liposome fusion, lipid transfection, protoplast fusion, retroviral infection, and biolistics.

The term "stable transfection" or "ST" refers to the introduction and integration of an exogenous nucleic acid, DNA, or RNA into the genome of a transfected cell. The term "stable transfectant" refers to a cell that stably integrates foreign DNA into genomic DNA.

The terms "nucleic acid molecule encoding", "coding DNA sequence" and "coding DNA" refer to the order of deoxyribonucleotides along a strand of deoxyribonucleic acid. The order of these deoxyribonucleotides determines the order of the amino acids along the polypeptide (protein) chain. Thus, the nucleic acid sequence encodes an amino acid sequence.

Methods for producing and purifying antibodies and antigen-binding fragments are well known in the art and can be found, for example, in chapters 5-8 and 15 in Using Antibodies: A Laboratory Manual, Cold Spring Harbor Laboratory. The antibodies or antigen-binding fragments thereof of the present disclosure are genetically engineered to add one or more human FR regions to CDR regions of non-human origin. Human FR germline sequences can be obtained from the website imgt.cines.fr of ImMunoGeneTics (IMGT), or J. Immunoglobulin, (2001) ISBN: 012441351.

The engineered antibodies or antigen-binding fragments thereof of the present disclosure can be prepared and purified by conventional methods. For example, cDNA sequences encoding heavy and light chains can be cloned and recombined into expression vectors. The recombinant immunoglobulin expression vector can stably transfect CHO cells. As a more recommended prior art, mammalian expression systems may result in glycosylation of antibodies, particularly at the highly conserved N-terminus of the Fc region. Stable clones are obtained by expressing antibodies that specifically bind to human antigens. Positive clones are enlarged cultured in a serum-free medium in a bioreactor to produce antibodies. The antibody-secreting medium may be purified and collected using conventional techniques. The antibody may be concentrated by filtration using conventional methods. Soluble mixtures and polymers may also be removed by conventional methods, such as molecular sieves, ion exchange, etc.

As used herein, the term "individual" or "subject" refers to any animal, such as a mammal or a bagged animal. Individuals of the present disclosure include but are not limited to, humans, non-human primates (e.g., cynomolgus or rhesus monkeys or other types of macaque), mice, pigs, horses, donkeys, cattle, sheep, rats, and any kind of poultry.

The term "antibody-drug conjugate" (ADC) refers to an antibody to which a therapeutically active substance or active drug ingredient (API) has been covalently coupled such that the therapeutically active substance or active drug ingredient (API) can be targeted to the binding target of the antibody to exhibit its pharmacological function.

The therapeutically active substance or active pharmaceutical ingredient may be a cytotoxin capable of killing the ADC-targeted cells, preferably a malignant or cancerous cell. Covalent attachment of the therapeutically active substance, active pharmaceutical ingredient, or cytotoxin can be carried out in a non-site-specific manner using standard chemical linkers that couple the payload to lysine or cysteine residues, or preferably, conjugation is carried out in a site-specific manner that allows full control of the conjugation site and the drug to antibody ratio of produced ADC.

The term "chimeric antigen receptor" (CAR) is an engineered receptor that transplants any specificity onto immune effector cells. Typically, these recipients are used to transplant the specificity of monoclonal antibodies onto T cells; the transfer of their coding sequences is facilitated by retroviral or lentiviral vectors or by transposons. CAR-engineered T cells (also abbreviated as CAR-T cells) are genetically engineered T cells harboring a chimeric receptor, the extracellular recognition unit of which comprises an antibody-derived recognition domain, and the intracellular region of which is derived from a lymphocyte stimulating moiety. The structure of the prototype CAR is modular and designed to accommodate various functional domains, thus enabling the selection of specificity and control of T cell activation. The preferred antibody-derived recognition unit is a single-chain variable fragment (scFv) that combines the specificity and binding residues of the heavy and light chain variable regions of a monoclonal antibody. The most common lymphocyte activation moiety comprises a T-cell costimulatory (e.g., CD28) domain in tandem with a T-cell triggering (e.g., CD3ζ) moiety. By arming effector lymphocytes (e.g., T cells and natural killer cells) with such chimeric receptors, the engineered cell is redirected with a predefined specificity to any desired target antigen, in a non-HLA-restricted manner.

CAR constructs are introduced ex vivo into T cells from peripheral lymphocytes of a given patient using retroviral or lentiviral vectors or transposons. Following infusion of the resulting CAR-engineered T cells back into the patient, they traffic, reach their target site, and upon interaction with their target cells or tissues, they undergo activation and perform their predefined effector function. Therapeutic targets for the CAR approach include cancer and HIV-infected cells, or autoimmune effector cells.

As used herein, the term "tumor" refers to a disease characterized by pathological proliferation of cells or tissues, and subsequent migration or invasion of other tissues or organs. The growth of a tumor is usually uncontrolled and progressive and does not induce or inhibit normal cell proliferation. Tumors can affect various cells, tissues or organs, including, but not limited to, bladder, bone, brain, breast, cartilage, glial cells, esophagus, fallopian tube, gallbladder, heart, intestine, kidney, liver, lung, lymph nodes, nerve tissue, ovary, pancreas, prostate, skeletal muscle, skin, spinal cord, spleen, stomach, testis, thymus, thyroid, trachea, urethra, ureter, urethra, uterus, vaginal organ, or tissue or corresponding cell. Tumors include cancers, such as sarcomas, carcinomas, or plasmacytomas (malignant tumors of plasma cells). The tumor according to the present disclosure may include, but is not limited to, leukemia (e.g. acute leukemia, acute lymphocytic leukemia, acute myeloid leukemia, acute myeloid leukemia, acute promyelocytic leukemia, acute myelo-monocytic leukemia, acute monocytic leukemia, chronic leukemia, chronic myelogenous leukemia, chronic lymphocytic leukemia, polycythemia vera), lymphoma (Hodgkin's disease, non-Hodgkin's disease), primary macroglobulinemia, heavy chain disease, solid tumors such as sarcomas and cancers (e.g. fibrosarcoma, myxosarcoma, liposarcoma, chondrosarcoma, osteosarcoma, chordoma, endothelial sarcoma, lymphangiosarcoma, angiosarcoma, lymphangioendothelioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, sweat adenocarcinoma, sebaceous adenocarcinoma, papillary carcinoma, papillary adenocarcinoma, bronchial carcinoma, myeloid cancer, renal cell carcinoma, liver cancer, nile duct carcinoma, choriocarcinoma, seminoma, embryo cancer, nephroblastoma, cervical cancer, uterine cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuromas, oligodendroglioma, schwannoma, meningioma, melanoma, neuroblastoma, retinoblastoma), esophageal cancer, gallbladder cancer, kidney cancer, multiple myeloma. Preferably, the "tumor" includes, but is not limited to: pancreatic cancer, liver cancer, lung cancer, gastric cancer, esophageal cancer, head and neck squamous cell carcinoma, prostate cancer, colon cancer, breast cancer, lymphoma, gallbladder cancer, renal cancer, leukemia, multiple myeloma, ovarian cancer, cervical cancer, and glioma.

As used herein, the term "disease" or "condition" or "disorder" or the like refers to any alteration or disorder that impairs or interferes with the normal function of a cell, tissue, or organ. For example, the "disease" includes, but is not limited to: tumors, pathogen infections, autoimmune diseases, T-cell dysfunctions, or deficiencies in immune tolerance (e.g., transplant rejection).

As used herein, the term "treatment" refers to clinical intervention in an attempt to alter a disease caused by an individual or treated cells, either prophylactically or clinically pathologically. Therapeutic effects include but are not limited to, prevention of the occurrence or recurrence of a disease, alleviation of symptoms, reduction of any disease's direct or indirect pathological consequences, prevention of metastasis, slowing of the rate of disease progression, amelioration or remission of a condition, remission or amelioration of a prognosis, etc.

The term "drug box" or "kit" includes an effective amount of one or more unit dosage forms of a pharmaceutical composition of the present disclosure. In some embodiments, the drug box may include a sterile container; such containers may be in the form of boxes, ampoules, bottles, vials, tubes, bags, blister packs, or other suitable containers known in the art. Such containers may be made of plastic, glass, laminated paper, metal foil, or other materials suitable for holding medicaments. In addition, the drug box also includes instructions for administering the pharmaceutical composition of the present disclosure to an individual. The instructions generally include methods of using the pharmaceutical compositions of the present disclosure to treat diseases.

EXAMPLE

The present disclosure will be described in detail below in connection with specific examples. It should be understood that these examples are only used to describe the present disclosure and are not intended to limit the scope of the present disclosure. The experimental methods in the following examples which are not specified with specific conditions are generally carried out according to conventional conditions, Molecular Cloning: A Laboratory Manual (Third Edition) by J. Sambrook et al., Science Press, 2002, or according to the conditions recommended by the manufacturer.

Example 1 Animal Immunization

To generate anti-CLDN18.2 antibodies, the assay procedure was performed using standard biological protocols.

A total of 15 mice of different strains were immunized with CHO-K1 cells (CHO-K1/hCLDN18.2) stably transfected expressing hCLDN18.2 and a DNA vector encoding hCLDN18.2 as immunogens.

In the later stage of immunization, blood was collected from the angular vein to obtain plasma samples, and the titer of immune serum was detected by ELISA and FACS to determine the immune response of the animals.

After 4 times of immunization, 6 mice were selected for euthanasia to prepare hybridoma cells.

Example 2 Production of Hybridoma Cell for Anti-CLDN18.2 Monoclonal Antibodies

To generate hybridoma cells for the anti-CLDN18.2 monoclonal antibody, 6 mice were euthanized with carbon dioxide, and feeder cells were separately harvested by syringe, and the feeder cell suspension was plated into a prepared 96-well plate. A certain number of myeloma cells and spleen cells were proportionally mixed for cell fusion. HAT medium (1 mL 100×HT supplement+1 mL aminopterin+10 mL FBS+88 mL DMEM) was added to the fused cells and mixed well to make cell suspension. The cell suspension was then poured into a culture dish and mixed well, and the cell suspension was plated into a 96-well feeder plate using a multichannel pipette. The fused feeder cell plates were placed in an incubator and incubated at a constant temperature of 37° C., 5.5% $CO_2$ for 7-10 days. Anti-CLDN18.2 positive clones were then screened by ELISA and FACS. The screened positive clones were subcloned by limiting dilution assay to obtain stable single hybridoma cells. Subcloned cell supernatants were screened by FACS using HEK293 cells stably transfected expressing hCLDN18.2 (HEK293-hCLDN18.2). As shown in FIGS. 1-5 of the description, 18 hybridoma cell strains to produce antibodies that specifically bind to hCLDN18.2 were finally obtained.

The hybridoma cell strain secreting the monoclonal antibody obtained by the screening was cultured, and the total RNA was extracted from the cell by a conventional biological method. cDNA was synthesized from the total RNA template via reverse transcription, using PrimeScript™ 1st Strand cDNA Synthesis Kit (TAKARA).

The cDNA then served as a template in the amplification using antibody constant region primers. After the PCR products were separated by agarose gel electrophoresis, the DNA fragments were purified and recovered, and the amino acid sequences of the variable regions of 18 monoclonal antibodies of the present disclosure were obtained by sequencing, and the results were shown in table 1:

TABLE 1

Amino acid sequences of the variable regions of 18 monoclonal antibodies

| Clone Number | Variable region of heavy chain (VH) | Variable region of light chain (VL) |
|---|---|---|
| 59F9 | SEQ ID NO: 1 | SEQ ID NO: 2 |
| 45H1 | SEQ ID NO: 3 | SEQ ID NO: 4 |
| 43F5 | SEQ ID NO: 5 | SEQ ID NO: 6 |
| 4007 | SEQ ID NO: 7 | SEQ ID NO: 8 |
| 76D11 | SEQ ID NO: 9 | SEQ ID NO: 10 |
| 32G8 | SEQ ID NO: 11 | SEQ ID NO: 12 |
| 37G8 | SEQ ID NO: 13 | SEQ ID NO: 14 |
| 39C8 | SEQ ID NO: 15 | SEQ ID NO: 16 |
| 4212 | SEQ ID NO: 17 | SEQ ID NO: 18 |
| 126A1B | SEQ ID NO: 19 | SEQ ID NO: 20 |
| 239E9 | SEQ ID NO: 21 | SEQ ID NO: 22 |
| 22909 | SEQ ID NO: 23 | SEQ ID NO: 24 |
| 252F11 | SEQ ID NO: 25 | SEQ ID NO: 26 |
| 299B2 | SEQ ID NO: 27 | SEQ ID NO: 28 |
| 24117 | SEQ ID NO: 29 | SEQ ID NO: 30 |
| 251H1B | SEQ ID NO: 31 | SEQ ID NO: 32 |
| 287F12 | SEQ ID NO: 33 | SEQ ID NO: 34 |
| 25304 | SEQ ID NO: 35 | SEQ ID NO: 36 |

Based on the above amino acid sequences, the CDRs and FRs of the variable regions of the antibodies were divided using Kabat numbering rules, and the composition of the 6 CDR sequences of each antibody was shown in Table 2 below, wherein the numbers in parentheses in Table 2 indicate the sequence numbers, e.g., (37) represents SEQ ID NO: 37.

TABLE 2

CDRs of 18 monoclonal antibodies

| Clone Number | HCDR1 | HCDR2 | HCDR3 | LCDR1 | LCDR2 | LCDR3 |
|---|---|---|---|---|---|---|
| 59F9 | GYWIE (SEQ ID NO: 37) | EILLGSGSIKYNVKFKD (SEQ ID NO: 38) | KGLRGNSFDY (SEQ ID NO: 39) | KSSQSLLNSGNQKSYLT (SEQ ID NO: 86) | WASTRES (SEQ ID NO: 93) | QNDYYYPFT (SEQ ID NO: 97) |

TABLE 2-continued

CDRs of 18 monoclonal antibodies

| Clone Number | HCDR1 | HCDR2 | HCDR3 | LCDR1 | LCDR2 | LCDR3 |
|---|---|---|---|---|---|---|
| 48H1 | NYWTH (SEQ ID NO: 40) | MIHPNSGSSNYNEKFKS (SEQ ID NO: 41) | IHYGNSMDY (SEQ ID NO: 42) | KSSQSLFNSGNQKNYLT (SEQ ID NO: 87) | WASTWES (SEQ ID NO: 94) | QNAYSYPFT (SEQ ID NO: 98) |
| 43F5 | SYWTH (SEQ ID NO: 43) | MIHPNSGSSNYNEKFKS (SEQ ID NO: 41) | IHYGNAMDY (SEQ ID NO: 44) | KSSQSLLNSGNQKNYLT (SEQ ID NO: 88) | WASTRES (SEQ ID NO: 93) | QNDYSFPFT (SEQ ID NO: 99) |
| 40G7 | NYWMH (SEQ ID NO: 45) | MIHPNSYSTNYNEKFRS (SEQ ID NO: 46) | IYYGNAMDY (SEQ ID NO: 47) | KSSQSLFNSGNQKNYLT (SEQ ID NO: 87) | WAFTRES (SEQ ID NO: 95) | QNDYSYPFT (SEQ ID NO: 100) |
| 76D11 | GYWIE (SEQ ID NO: 37) | EILPGSGSIKYNEKFKD (SEQ ID NO: 48) | KGLRGNSFDY (SEQ ID NO: 39) | KSSQSLLNSGNQKNYLT (SEQ ID NO: 88) | WASTRES (SEQ ID NO: 93) | QNDYYYPFT (SEQ ID NO: 97) |
| 32G8 | DYHMN (SEQ ID NO: 49) | VINPYNGGIRYNQKFKG (SEQ ID NO: 50) | IYYGNSFAY (SEQ ID NO: 51) | KSSQSLLNSGNQKNYLT (SEQ ID NO: 88) | WASTRES (SEQ ID NO: 93) | QNNYIYPFT (SEQ ID NO: 101) |
| 37G8 | DYHMN (SEQ ID NO: 49) | LINPYNGGIRFNQKFKG (SEQ ID NO: 52) | IYYGNSFAY (SEQ ID NO: 51) | KSGQSLLNSGNQKNYLT (SEQ ID NO: 89) | WASTRES (SEQ ID NO: 93) | QNDYFYPYT (SEQ ID NO: 102) |
| 39C8 | SYWMI (SEQ ID NO: 53) | QIYPGDGDTNYNGKFKG (SEQ ID NO: 54) | IYYGNAFAY (SEQ ID NO: 55) | KSSQSLLNSGNQKNYLT (SEQ ID NO: 88) | WASTRES (SEQ ID NO: 93) | QNDYSYPFT (SEQ ID NO: 100) |
| 42D2 | DYQMN (SEQ ID NO: 56) | FINPYNGGIRYNQKFKG (SEQ ID NO: 57) | IYFGNSFAN (SEQ ID NO: 58) | KPSQSLLNSGNQKNYLT (SEQ ID NO: 90) | WASTRES (SEQ ID NO: 93) | QNDYIYPYT (SEQ ID NO: 103) |
| 126A11 | TYGVS (SEQ ID NO: 59) | VIWGDGSTNYHSALIS (SEQ ID NO: 60) | PGLRNAMDY (SEQ ID NO: 61) | KSSQSLLNSGNQKNYLA (SEQ ID NO: 91) | GASTRES (SEQ ID NO: 96) | QNDLIYPLT (SEQ ID NO: 104) |
| 239E9 | DYTMH (SEQ ID NO: 62) | FIGVYYGNTNYNQKFKG (SEQ ID NO: 63) | IGRGNAMDY (SEQ ID NO: 64) | KSSQSLLNSGNQKNYLT SEQ ID NO: 88 | WASTRES (SEQ ID NO: 93) | QNAYSYPFT (SEQ ID NO: 98) |
| 229C9 | SGYSWH (SEQ ID NO: 65) | YIHYSGGTNYNPSLKS (SEQ ID NO: 66) | LERGNSFAY (SEQ ID NO: 67) | KSTQSLLNSGNQKNYLT (SEQ ID NO: 92) | WASTRES (SEQ ID NO: 93) | QNDYFYPFT SEQ ID NO: 105 |
| 252F11 | INYVMS (SEQ ID NO: 68) | BIRTGGDYTYYVDTVTG (SEQ ID NO: 69) | VGYGNSLDY (SEQ ID NO: 70) | KSSQSLLNSGNQKNYLT (SEQ ID NO: 88) | WASTRES (SEQ ID NO: 93) | QNNYFYPLT (SEQ ID NO: 106) |
| 299B2 | NYWIH (SEQ ID NO: 71) | RIYPGTGNTYYNEKFTG (SEQ ID NO: 72) | EGYGKGNSMDY (SEQ ID NO: 73) | KSSQSLLNSGNQKNYLT (SEQ ID NO: 88) | WASTRES (SEQ ID NO: 93) | QNAYYYPYT (SEQ ID NO: 107) |
| 241F7 | AYNMN (SEQ ID NO: 74) | NIDPYYGGTNYNQKFKG (SEQ ID NO: 75) | VYYGNSLIY (SEQ ID NO: 76) | KSSQSLLNSGNQKNYLT (SEQ ID NO: 88) | WASTRES (SEQ ID NO: 93) | QNNYFYPLT (SEQ ID NO: 106) |
| 251H11 | TFWIH (SEQ ID NO: 77) | KIYPGTGYTYYNEKFKG (SEQ ID NO: 78) | EGYGKGNAVDF (SEQ ID NO: 79) | KSSQSLFNSGNQKNYLT (SEQ ID NO: 87) | WASTRES (SEQ ID NO: 93) | QNDYTYPST (SEQ ID NO: 108) |
| 287F12 | TAGMH (SEQ ID NO: 80) | WTNTHSGEPKYAEDPKG (SEQ ID NO: 81) | WGRGNALDY (SEQ ID NO: 82) | KSSQSLLNSGNQKNYLT SEQ ID NO: 88 | WASTRES (SEQ ID NO: 93) | QNTYSYPLT (SEQ ID NO: 109) |
| 253 C4 | SYWIH (SEQ ID NO: 83) | RFYPGTGTAYYNENFEG (SEQ ID NO: 84) | EGYGKGNAMDY (SEQ ID NO: 85) | KSSQSLLNSGNQKNYLT (SEQ ID NO: 88) | WASTRES (SEQ ID NO: 93) | QNDYYFPFT SEQ ID NO: 110 |

Example 3 Construction of an Anti-CLDN18.2 Chimeric Antibody and Transient Transfection Expression of the Same in Eukaryotic Cells The target gene fragment generated after splicing the sequenced monoclonal antibody variable region of the present disclosure and the human IgG1 constant region was cloned into a pcDNA3.4 expression vector to prepare a transfection-grade expression plasmid. Expi293F™ cells (Thermo Fisher Scientific) were cultured in a serum-free medium, seeded in shake flasks (Coming Inc.), and cultured on a shaking table in an environment of 37° C., 8% $CO_2$. The cell density was adjusted, the recombinant expression vector containing the target gene fragment and the Expi-Fectamine™ 293 transfection reagent were mixed according to an appropriate ratio and added into a cell culture shake flask, after transfection 16-18 h, ExpiFectamine™ 293 Transfection Enhancer 1 and ExpiFectamine™ 293 Transfection Enhancer 2 were added, the supernatant was collected and purified after 6 days of cell culture, and finally purified chimeric antibody was subjected to SDS-PAGE purity analysis and A280 concentration determination. Chimeric antibodies were named in such a way that the prefix ch- was added based on the original hybridoma clone.

Example 4 Binding Assay of Anti-CLDN18.2 Chimeric Antibody a. Binding of Anti-CLDN18.2 Chimeric Antibodies to Cells Expressing hCLDN18.2

FACS was used to detect the binding of anti-CLDN18.2 chimeric antibodies to HEK293 cells stably transfected expressing hCLDN18.2 (HEK293-hCLDN18.2) and gastric cancer tumor tissue-derived cells naturally expressing hCLDN18.2 (PDX-hCLDN18.2).

HEK293-hCLDN18.2 or PDX-hCLDN18.2 cells were harvested and resuspended in PBS to adjust cell concentration, and the gradiently diluted antibody was added, with irrelevant human IgG being a negative control and chimeric antibody ch-175D10 from patent CN103509110B being a positive control (reference antibody). Following incubation in a 4° C. shaking table for 50 min-1 h, the mixture was centrifugally washed twice with phosphate buffer solution, added with fluorescently labeled anti-human IgG secondary antibody, 100 μL per well; after incubation in a 4° C. shaking table for 40 min-1 h, the mixture was centrifugally washed twice with phosphate buffer solution, and then the prepared sample was detected on a flow cytometer; the mean fluorescence intensity (hereinafter referred to as MFI) for each concentration was calculated by the software, and then the half binding concentration (hereinafter referred to as $EC_{50}$) and the mean maximum fluorescence intensity (Top MFI) were calculated by GraphPad software, and the results were shown in Table 3.

TABLE 3

Binding of anti-CLDN18.2 chimeric antibodies to hCLDN18.2

| | HEK293-hCLDN18.2 | | PDX-hCLDN18.2 | |
|---|---|---|---|---|
| Clone Number | $EC_{50}$ (nM) | Mean maximum fluorescence intensity (Top MFI) | $EC_{50}$ (nM) | Mean maximum fluorescence intensity (Top MFI) |
| ch-175D10 | 0.881 | 5451 | 63.85 | 7160 |
| ch-59F9 | 2.411 | 9038 | 12.38 | 18084 |
| ch-48H1 | 2.922 | 9485 | 5.588 | 13614 |
| ch-43F5 | 1.510 | 5586 | 5.354 | 7616 |
| ch-40G | 2.309 | 7467 | 7.687 | 10118 |
| ch-76D11 | 2.464 | 8718 | 12.31 | 16836 |
| ch-32G8 | 2.657 | 8645 | 5.392 | 14764 |
| ch-37G8 | 5.048 | 10376 | 6.999 | 14399 |
| ch-39C8 | 2.700 | 7820 | 20.14 | 17548 |
| ch-42D2 | 2.416 | 10385 | 7.418 | 15709 |
| ch-126A11 | 2.121 | 9972 | 14.99 | 17121 |
| ch-239E9 | 2.308 | 9269 | 4.554 | 14552 |
| ch-229C9 | 2.457 | 9869 | 10.67 | 15716 |
| ch-252F11 | 2.202 | 8383 | 15.82 | 16505 |
| ch-299B2 | 1.524 | 10126 | 5.809 | 16342 |
| ch-241F7 | 3.024 | 12203 | 4.871 | 15220 |
| ch-251H11 | 2.721 | 10790 | 96.23 | 19876 |
| ch-287F12 | 2.650 | 10947 | 16.78 | 17591 |
| ch-253C4 | 2.275 | 10345 | 9.735 | 15546 |

Table 3 and FIGS. 6-17 showed the affinity results for the chimeric antibody of the present disclosure and the reference antibody ch-175D10 to HEK293-hCLDN18.2 cells and PDX-hCLDN18.2 cells, respectively. Experimental results showed that: the binding of the chimeric antibody of the present disclosure to HEK293-hCLDN18.2 cells exhibited a mean maximum fluorescence intensity of 5586-12203, whereas the binding of the reference antibody ch-175D10 to HEK293-hCLDN18.2 under the same reaction conditions exhibited a mean maximum fluorescence intensity of only 5451. The binding of the chimeric antibody to PDX-hCLDN18.2 exhibited a mean maximum fluorescence intensity of 7616-19876, a half binding concentration ($EC_{50}$) of 4.554-96.23 nM, whereas the binding of the reference antibody ch-175D10 to PDX-hCLDN18.2 under the same reaction conditions exhibited a mean maximum fluorescence intensity of only 7160 and a half binding concentration ($EC_{50}$) of only 63.85 nM. Thus, the binding of most chimeric antibodies of the present disclosure to hCLDN18.2 antigen was more strongly than that of ch-175D10.

B. Binding Selectivity of Anti-CLDN18.2 Chimeric Antibodies

FACS was used to detect the binding of chimeric antibodies of the present disclosure to HEK293 cells stably transfected expressing murine CLDN18.2 (HEK293-mCLDN18.2) and HEK293 cells stably transfected expressing human CLDN18.1 (HEK293-hCLDN18.1).

HEK293-mCLDN18.2 and HEK293-hCLDN18.1 cells were harvested separately and resuspended in PBS to adjust cell concentration, and the gradiently diluted chimeric antibody was added, wherein irrelevant human IgG was used as a negative control and ch-175D10 was still a positive control (reference antibody). Following incubation in a 4° C. shaking table for 50 min, the mixture was centrifugally washed twice with phosphate buffer solution, added with fluorescently labeled anti-human IgG secondary antibody, 100 μL per well; after incubation in a 4° C. shaking table for 40 min, the mixture was centrifugally washed twice with phosphate buffer solution, and then the prepared sample was detected on a flow cytometer; the half binding concentration ($EC_{50}$) and the mean maximum fluorescence intensity (Top MFI) were calculated by GraphPad software, and the results were shown in Table 4.

TABLE 4

Binding of anti-CLDN18.2 chimeric antibodies to mCLDN18.2 and hCLDN18.1, respectively

| | HEK293-mCLDN18.2 | | |
|---|---|---|---|
| Clone Number | $EC_{50}$ (nM) | Mean maximum fluorescence intensity (Top MFI) | HEK293-hCLDN18.1 Binding or not (+/−) |
| ch-175D10 | 1.014 | 4187 | − |
| ch-59F9 | 1.222 | 11162 | − |
| ch-48H1 | 1.763 | 14768 | − |
| ch-43F5 | 1.132 | 6093 | − |
| ch-40G7 | 1.115 | 10037 | − |
| ch-76D11 | 0.702 | 6337 | − |
| ch-32G8 | 0.840 | 6870 | − |
| ch-37G8 | 1.712 | 8926 | − |
| ch-39C8 | 1.627 | 10599 | − |
| ch-42D2 | 0.764 | 7400 | − |
| ch-126A11 | 0.573 | 7636 | − |
| ch-239E9 | 1.241 | 12726 | − |
| ch-229C9 | 1.188 | 12740 | − |
| ch-252F11 | 0.948 | 8975 | − |
| ch-299B2 | 0.758 | 13595 | − |
| ch-241F7 | 1.160 | 10495 | − |
| ch-251H11 | 1.009 | 8588 | − |
| ch-287F12 | 1.138 | 10191 | − |
| ch-253C4 | 0.790 | 8326 | − |

Table 4 showed the affinity results for the chimeric antibody of the present disclosure and the reference antibody ch-175D10 to HEK293-mCLDN18.2 cells and HEK293-hCLDN18.1 cells, respectively. Experimental results showed that: the chimeric antibody of the present disclosure was the same as the reference antibody ch-175D10, both of which bound to the mCLDN18.2 antigen, wherein the binding of the chimeric antibody to HEK293-mCLDN18.2 exhibited a mean maximum fluorescence intensity of 6093-14768 and a half binding concentration ($EC_{50}$) of 0.573-1.763 nM, the binding of the reference antibody ch-175D10 to HEK293-mCLDN18.2 under the same reaction conditions exhibited a mean maximum fluorescence intensity of 4187 and a half binding concentration ($EC_{50}$) of 1.014 nM, indicating that the chimeric antibody exhibited the binding $EC_{50}$ comparable to that of the reference antibody, and the maximum binding higher than that of the reference antibody. Moreover, the chimeric antibody was the same as the reference antibody ch-175D10, neither binding to the hCLDN18.1 antigen.

Example 5 In Vitro Functional Assay of Anti-CLDN18.2 Chimeric Antibodies a. Antibody-Dependent Cell-Mediated Cytotoxicity (ADCC)

CHO-K1/hCLDN18.2 cells were used as target cells, NK cells transfected with 158V/V type FcγRIIIa gene (NK92/FcRγ3a.158V/V) were used as effector cells, and the release of lactate dehydrogenase (LDH) in cell was detected by the cytotoxicity assay kit (Roche) and used as an indicator of cell killing effect.

CHO-K1/hCLDN18.2 cells were harvested by centrifugation, the supernatant was discarded, and the cells were resuspended in ADCC buffer to adjust the cell density and transferred to a 96-well assay plate. Chimeric antibodies, control sample working solutions, or ADCC buffer at different concentration gradients were transferred to a 96-well plate, incubated for about 30 min in a cell incubator (37° C./5% $CO_2$), effector cells, ADCC buffer, or cell lysates were transferred to a 96-well assay plate, and incubated for an additional about 6 h in a cell incubator (37° C./5% $CO_2$). After the incubation, the 96-well assay plate was removed and centrifuged at a low rotating speed, the supernatant was pipetted carefully and transferred into a new 96-well assay plate, LDH detection working solution was added, the plate was incubated at room temperature for about 10-30 min, the OD value was detected on a microplate reader, wherein a detection wavelength was 492 nm, and a reference wavelength was 650 nm.

The percentage of cell lysis caused by the ADCC effect was calculated using the following formula:

% cell lysis=100%× (sample release-target cell/effector cell mixed release)/(maximum release-target cell release), wherein the maximum release was the absorbance value produced in the wells of target cells treated with Triton X-100, the target cell/effector cell mixed release was the absorbance value produced in the wells of target cells and effector cell mixture, and the target cell release was the absorbance value produced in the wells containing only target cells, the sample release was the absorbance values produced in the wells of chimeric antibody, target cells, and effector cells mixture, and $EC_{50}$ and maximal lysis were calculated by GraphPad software, and the results were shown in Table 5.

TABLE 5

ADCC activity of anti-CLDN18.2 chimeric antibodies

| Clone Number | Maximum lysis (%) | $EC_{50}$ (μg/ml) |
|---|---|---|
| ch-175D10 | 31.81 | 0.021 |
| ch-59F9 | 29.37 | 0.023 |
| ch-48H1 | 44.73 | 0.011 |
| ch-43F5 | 48.46 | 0.064 |
| ch-40G7 | 32.72 | 0.018 |
| ch-76D11 | 45.60 | 0.021 |
| ch-32G8 | 46.83 | 0.019 |
| ch-37G8 | 31.71 | 0.022 |
| ch-39C8 | 34.45 | 0.022 |
| ch-42D2 | 39.12 | 0.020 |
| ch-126A11 | 36.65 | 0.010 |
| ch-239E9 | 36.68 | 0.021 |
| ch-229C9 | 29.06 | 0.023 |
| ch-252F11 | 31.09 | 0.022 |
| ch-299B2 | 33.52 | 0.047 |
| ch-241F7 | 36.57 | 0.027 |
| ch-251H11 | 38.79 | 0.024 |
| ch-287F12 | 35.46 | 0.017 |
| ch-253C4 | 35.72 | 0.036 |

Table 5 and FIGS. 18-23 showed ADCC results for the chimeric antibody of the present disclosure and the reference antibody ch-175D10 on CHO-K1/hCLDN18.2 cells. Experimental results showed that: the maximal ADCC effect of the chimeric antibody of the present disclosure on CHO-K1/hCLDN18.2 cells was 29.06%-48.46%, and the ADCC effect of the reference antibody ch-175D10 was 31.81% under the same reaction conditions. The concentration of the chimeric antibody of the present disclosure that produces 50% ADCC effect ($EC_{50}$) was 0.010-0.064 μg/mL, and the concentration of ch-175D10 that produces 50% ADCC effect ($EC_{50}$) under the same reaction conditions was 0.021 μg/mL. The above results demonstrated that the chimeric antibodies of the present disclosure were comparable to the reference antibody ch-175D10 in ADCC activity.

B. Complement-Dependent Cytotoxicity (CDC)

Cell viability was measured by CellTiter-Glo® chemiluminescent cell viability assay kit (Promega) using CHO-K1/ hCLDN18.2 as target cells and pooled normal human serum (PNHS) as complement source.

CHO-K1/hCLDN18.2 cells were harvested, resuspended in CDC buffer to adjust cell density, seeded into a 384-well cell plate, 20 μL per well, to prepare a 4-fold concentration of sample solution, which (CDC buffer as control) was transferred to the corresponding wells of the 384-well cell plate, 10 μL per well, the plate was incubated at room temperature for about 30 min, and the pooled normal human serum (PNHS) was diluted to the 4-fold working concentration using CDC buffer. The diluted PNHS was transferred to the corresponding wells of the incubated 384-well plate, 10 μL per well, the plate was incubated in a cell incubator (37° C./5% $CO_2$) for about 4 h, the 384-well plate was removed and assayed with CellTiter-Glo® chemiluminescent cell viability assay kit (Promega), and the results were read using PHERAstar Plus software.

The cell lysis rate caused by the chimeric antibody in the CDC assay was calculated using the following formula:

% cell lysis=100%×(1−(test wells-serum control wells)/(cell+serum wells-serum control wells))

The experimental controls are: the serum control wells: only serum (i.e., 30 μL buffer+10 μL diluted serum). Cells+ serum wells: serum was added to wells of CHO-K1/hCLDN18.2 cell suspension (i.e., 20 μL cell suspension+10 μL buffer+10 μL diluted serum). Test wells: serum and chimeric antibody were added to wells of CHO-K1/hCLDN18.2 cell suspension (i.e., 20 μL cell suspension+10 μL antibody+10 μL diluted serum). The $EC_{50}$ and maximum lysis were calculated using GraphPad software, and the results were shown in Table 6.

TABLE 6

| CDC activity of anti-CLDN18.2 chimeric antibodies | | |
|---|---|---|
| Clone Number | Maximum lysis (%) | $EC_{50}$ (μg/ml) |
| ch-175D10 | 87.41 | 1.193 |
| ch-59F9 | 94.71 | 0.091 |
| ch-48H1 | 94.27 | 0.170 |
| ch-43F5 | 89.79 | 0.206 |
| ch-40G7 | 89.08 | 0.380 |
| ch-76D11 | 95.36 | 0.108 |
| ch-32G8 | 93.85 | 0.108 |
| ch-37G8 | 92.86 | 0.160 |
| ch-39C8 | 94.75 | 0.177 |
| ch-42D2 | 94.47 | 0.130 |
| ch-126A11 | 95.02 | 0.065 |
| ch-239E9 | 94.80 | 0.139 |
| ch-229C9 | 96.11 | 0.165 |
| ch-252F11 | 95.44 | 0.179 |
| ch-299B2 | 95.53 | 0.124 |
| ch-241F7 | 95.05 | 0.099 |
| ch-251H11 | 97.11 | 0.359 |
| ch-287F12 | 96.32 | 0.141 |
| ch-253C4 | 95.23 | 0.038 |

Table 6 and FIGS. 24-29 showed CDC results for the chimeric antibody of the present disclosure and the reference antibody ch-175D10 on CHO-K1/hCLDN18.2 cells. Experimental results showed that: the maximal CDC effect of the chimeric antibody of the present disclosure on CHO-K1/hCLDN18.2 cells was 89.08%-97.11%, and the maximal CDC effect of the reference antibody ch-175D10 was 87.41% under the same reaction conditions. The concentration of the chimeric antibody of the present disclosure that produces 50% CDC effect ($EC_{50}$) was 0.038-0.380 pg/mL, and the concentration of ch-175D10 that produces 50% CDC effect ($EC_{50}$) under the same reaction conditions was higher than 1 μg/mL. It can be seen that the CDC activity of most antibodies was stronger than that of the reference antibody.

Example 6 Preparation of Variants of Anti-CLDN18.2 Chimeric Antibodies

Through post-translational modification (PTM) analysis of the monoclonal antibody disclosed by the present disclosure, it was found that 1 deamidation site was present in both variable regions of 299B2 and 253C4; single site-directed mutagenesis was performed on the 31st, or 32nd, or 33rd amino acid in the variable region of the light chain of 299B2 to prepare three mutants of 299B2: 299B2-N31Q, 299B2-S32A, and 299B2-G33A, respectively.

And single site-directed mutagenesis was performed on the 31st, or 32nd, or 33rd amino acid in the variable region of the light chain of 253C4 to prepare three mutants of 253C4: 253C4-N31Q, 253C4-S32A, and 253C4-G33A, respectively.

The amino acid sequences of the heavy chain variable region of 299B2-N31Q, 299B2-S32A, and 299B2-G33A were the same as that of 299B2, the amino acid sequences of the heavy chain variable region of 253C4-N31Q, 253C4-S32A, and 253C4-G33A were the same as that of 253C4. The variable region CDR sequences and heavy and light chain variable region sequences of the 6 variants described above were shown in Tables 7 and 8, respectively.

TABLE 7

| CDR sequences of antibodies 299B2 and 253C4 and variants thereof | | | | | | |
|---|---|---|---|---|---|---|
| Clone Number | HCDR1 | HCDR2 | HCDR3 | LCDR1 | LCDR2 | LCDR3 |
| 299B2 | NYWIH (SEQ ID NO: 71) | RIYPGTGNTYYNEKFTG (SEQ ID NO: 72) | EGYGKGNSMDY (SEQ ID NO: 73) | KSSQSLLNSGNQKNYLT (SEQ ID NO: 88) | WASTRES (SEQ ID NO: 93) | QNAYYYPYT (SEQ ID NO: 107) |
| 299B2-N31Q | NYWIH (SEQ ID NO: 71) | RIYPGTGNTYYNEKFTG (SEQ ID NO: 72) | EGYGKGNSMDY (SEQ ID NO: 73) | KSSQSLLQSGNQKNYLT (SEQ ID NO: 111) | WASTRES (SEQ ID NO: 93) | QNAYYYPYT (SEQ ID NO: 107) |
| 299B2-S32A | NYWIH (SEQ ID NO: 71) | RIYPGTGNTYYNEKFTG (SEQ ID NO: 72) | EGYGKGNSMDY (SEQ ID NO: 73) | KSSQSLLNAGNQKNYLT (SEQ ID NO: 112) | WASTRES (SEQ ID NO: 93) | QNAYYYPYT (SEQ ID NO: 107) |

TABLE 7-continued

CDR sequences of antibodies 299B2 and 253C4 and variants thereof

| Clone Number | HCDR1 | HCDR2 | HCDR3 | LCDR1 | LCDR2 | LCDR3 |
|---|---|---|---|---|---|---|
| 299B2-G33A | NYWIH (SEQ ID NO: 71) | RIYPGTGNTYYNEKFTG (SEQ ID NO: 72) | EGYGKGNSMDY (SEQ ID NO: 73) | KSSQSLLNSANQKNYLT (SEQ ID NO: 113) | WASTRES (SEQ ID NO: 93) | QNAYYYPYT (SEQ ID NO: 107) |
| 253C4 | SYWIH (SEQ ID NO: 83) | RFYPGTGTAYYNENFEG (SEQ ID NO: 84) | EGYGKGNAMDY (SEQ ID NO: 85) | KSSQSLLNSGNQKNYLT (SBQ ID NO: 88) | WASTRES (SEQ ID NO: 93) | QNDYYFPFT (SEQ ID NO: 110) |
| 253C4-N31Q | SYWIH (SEQ ID NO: 83) | RFYPGTGTAYYNENFEG (SEQ ID NO: 84) | EGYGKGNAMDY (SEQ ID NO: 85) | KSSQSLLQSGNQKNYLT (SEQ ID NO: 111) | WASTRES (SEQ ID NO: 93) | QNDYYFPFT (SEQ ID NO: 110) |
| 253C4-S32A | SYWIH (SEQ ID NO: 83) | RFYPGTGTAYYNENFEG (SEQ ID NO: 84) | EGYGKGNAMDY (SEQ ID NO: 85) | KSSQSLLNAGNQKNYLT (SEQ ID NO: 112) | WASTRES (SEQ ID NO: 93) | QNDYYFPFT (SEQ ID NO: 110) |
| 253C4-G33A | SYWIH (SEQ ID NO: 83) | RFYPGTGTAYYNENFEG (SEQ ID NO: 84) | EGYGKGNAMDY (SEQ ID NO: 85) | KSSQSLLNSANQKNYLT (SEQ ID NO: 113) | WASTRES (SEQ ID NO: 93) | QNDYYFPFT (SEQ ID NO: 110) |

TABLE 8

Variable region sequences of antibodies 299B2 and 253C4 and variants thereof

| Clone Number | Heavy chain variable region | Light chain variable region |
|---|---|---|
| 299B2 | SEQ ID NO: 27 | SEQ ID NO: 28 |
| 299B2-N31Q | SEQ ID NO: 27 | SEQ ID NO: 114 |
| 299B2-S32A | SEQ ID NO: 27 | SEQ ID NO: 115 |
| 299B2-G33A | SEQ ID NO: 27 | SEQ ID NO: 116 |
| 253C4 | SEQ ID NO: 35 | SEQ ID NO: 36 |
| 253C4-N31Q | SEQ ID NO: 35 | SEQ ID NO: 117 |
| 253C4-S32A | SEQ ID NO: 35 | SEQ ID NO: 118 |
| 253C4-G33A | SEQ ID NO: 35 | SEQ ID NO: 119 |

As described in Example 3, a chimeric antibody was constructed by subcloning the target gene fragment produced by splicing the 6 variant variable regions described above with the human IgG1 constant region into an expression vector, and the chimeric antibody of the variant was named in such a way that the prefix ch- was added based on the "hybridoma clone-mutation site", for example, a chimeric antibody of 299B2-N31Q was designated as ch-299B2-N31Q. Following transient expression in mammalian cell lines, affinity assays were performed using HEK293-hCLDN18.2 cells and monoclonal cell supernatants were screened by PACS. Affinity results for variants of antibodies ch-299B2 and ch-253C4 are shown in Table 9.

TABLE 9

Affinity of variants of antibodies ch-299B2 and ch-253C4

| Clone Number | $EC_{50}$ (ng/ml) | Mean maximum fluorescence intensity (Top MFI) |
|---|---|---|
| ch-175D10 | 155.9 | 2836 |
| ch-299B2-X31Q | —* | —* |
| ch-299B2-S32A | 1307 | 6504 |
| ch-299B2-G33A | 157.0 | 6869 |
| ch-253C4-N31Q | 175.0 | 6565 |
| ch-253C4-S32A | 206.7 | 6894 |
| ch-253C4-G33A | 186.7 | 6837 |

*The maximum concentration has not reached the maximum binding, and the curve cannot be fitted.

Example 7 Preparation of Humanized Antibodies

A. Humanized Design and Expression of Antibody 299B2-S32A

Through sequence similarity comparison, the antibody germline with the highest similarity to 299B2 was selected as an antibody template. In this example, the IMGT database IGHV1-46*01 was selected as an antibody template for the heavy chain of 299B2-S32A, IGKV4-1*01 was selected as an antibody template for the light chain of 299B2-S32A, the CDR regions of the antibody template were replaced with the CDR regions of the light chain and heavy chain of 299B2-S32A.

Homologous modeling of murine antibody variable region sequences was performed. The best modeling template was searched in the PDB antibody database based on the sequence of the murine antibody variable region, and 2GKI with 74% homology was selected as the template. Based on the spatial structure of 2GKI, the amino acid residues in the framework region of the CDR-grafted sequence were back-mutated according to the following criteria: 1. the classical residues in the framework region was selected for back mutation; 2. the residues of the hydrophobic core region in the framework region was selected for back mutation; 3. the residues in the heavy chain/light chain interaction interface was selected for back mutation; 4. similar residues was also selected for low priority back mutations.

299B2-S32A was humanized to obtain 4 humanized antibodies hu299B2-S32A-1, hu299B2-S32A-2, hu299B2-S32A-3, and hu299B2-S32A-4, the sequences of all humanized antibodies of 299B2-S32A mentioned above were shown in Table 10.

The target gene fragment which was generated by splicing the humanized antibody hu299B2-S32A variable region and the human IgG1 constant region was subcloned into a pcDNA3.4 expression vector via standard methods known to those skilled in the art, Expi293F™ cells in a logarithmic growth phase were transiently transfected by an Expi-Fectamine™ 293 transfection reagent, and culture supernatant was collected and subjected to affinity purification, the final purified antibody was subjected to SDS-PAGE purity analysis and A280 concentration determination.

B. Humanized Design and Expression of Antibody 253C4-N31Q

Through sequence similarity comparison, the antibody germline with the highest similarity to 253C4 was selected as an antibody template. In this example, the IMGT database IGKV4-1*01 was selected as an antibody template for the heavy chain of 253C4-N31Q, IGHV1-2*06 was selected as an antibody template for the light chain of 253C4-N31Q, the CDR regions of the antibody template were replaced with the CDR regions of the light chain and heavy chain of 253C4-N31Q.

Homologous modeling of murine antibody variable region sequences was performed. The best modeling template was searched in the PDB antibody database based on the sequence of the murine antibody variable region, and 2GKI with 74% homology was selected as the template. Based on the spatial structure of 2GKI, the amino acid residues in the framework region of the CDR-grafted sequence were back-mutated according to the following criteria: 1. the classical residues in the framework region was selected for back mutation; 2. the residues of the hydrophobic core region in the framework region was selected for back mutation; 3. the residues in the heavy chain/light chain interaction interface was selected for back mutation; 4. similar residues was also selected for low priority back mutations.

253C4-N31Q was humanized to obtain 3 humanized antibodies hu253C4-N31Q-1, hu253C4-N31Q-2, and hu253C4-N31Q-3, the sequences of all 253C4-N31Q humanized antibodies were shown in Table 10.

The target gene fragment which was generated by splicing the humanized antibody hu253C4-N31Q variable region and the human IgG1 constant region was subcloned into a pcDNA3.4 expression vector via standard methods known to those skilled in the art, Expi293F™ cells in a logarithmic growth phase were transiently transfected by an Expi-Fectamine™ 293 transfection reagent, and culture supernatant was collected and subjected to affinity purification, the final purified antibody was subjected to SDS-PAGE purity analysis and A280 concentration determination.

TABLE 10

Variable region sequences of humanized antibodies hu299B2-S32A and hu253C4-N31Q

| Clone Number | Heavy chain variable region | Light chain variable region |
| --- | --- | --- |
| hu299B2-S32A-1 | SEQ ID NO: 120 | SEQ ID NO: 121 |
| hu299B2-S32A-2 | SEQ ID NO: 120 | SEQ ID NO: 123 |
| hu299B2-S32A-3 | SLQ ID NO: 120 | SEQ ID NO: 124 |
| hu299B2-S32A-4 | SEQ ID NO: 122 | SEQ ID NO: 121 |
| hu253C4-N31Q-1 | SEQ ID NO: 125 | SEQ ID NO: 126 |
| hu253C4-N31Q-2 | SEQ ID NO: 125 | SEQ ID NO: 127 |
| hu253C4-N31Q-3 | SEQ ID NO: 128 | SEQ ID NO: 126 |

Example 8 Binding Activity of Humanized Antibodies Hu299B2 and Hu253C4

A. Binding of Humanized Antibodies to Cells Expressing hCLDN18.2

Binding activity assays were performed using HEK293-hCLDN18.2 and PDX-hCLDN18.2 cells, with reference to Example 4A, with irrelevant human IgG being a negative control and chimeric antibody ch-175D10 from patent CN103509110B being a positive control (reference antibody).

Using flow cytometry measurement, the mean fluorescence intensity (hereinafter referred to as MFI) for each concentration was calculated by the software, and then the half binding concentration ($EC_{50}$) and the mean maximum fluorescence intensity (Top MFI) were calculated by GraphPad software, and the results were shown in Table 11.

TABLE 11

Binding of anti-CLDN18.2 humanized antibody to hCLDN18.2

| | HEK293-hCLDN18.2 | | PDX-hCLDN18.2 | |
| --- | --- | --- | --- | --- |
| Clone Number | $EC_{50}$ (nM) | Mean maximum fluorescence intensity (Top MEI) | $EC_{50}$ (nM) | Mean maximum fluorescence intensity (Top MFI) |
| ch-175D10 | 1.434 | 26921 | 24.89 | 5703 |
| hu299B2-S32A-1 | 0.407 | 29529 | 29.68 | 25189 |
| hu299B2-S32A-2 | 0.463 | 36728 | 24.60 | 22877 |
| hu299B2-S32A-3 | 0.399 | 39986 | 26.12 | 24291 |
| hu299B2-S32A-4 | 0.318 | 31234 | 29.26 | 22967 |
| hu253C4-N31Q-1 | 0.216 | 23017 | 12.02 | 16291 |
| hu253C4-N31Q-2 | 0.361 | 29037 | 11.42 | 15585 |
| hu253C4-N31Q-3 | 0.145 | 18772 | 25.57 | 21616 |

Table 11 and FIGS. 30-33 showed the affinity results for the humanized antibody of the present disclosure and the reference antibody ch-175D10 to HEK293-hCLDN18.2 cells and PDX-hCLDN18.2 cells, respectively. Experimental results showed that: the binding of hu299B2-S32A humanized antibody of the present disclosure to HEK293-hCLDN18.2 cells exhibited a mean maximum fluorescence intensity of 29529-39986, whereas the binding of the reference antibody ch-175D10 to HEK293-hCLDN18.2 under the same reaction conditions exhibited a mean maximum fluorescence intensity of only 26921, indicating that the affinity of the humanized antibody hu299B2-S32A to HEK293-hCLDN18.2 was superior to that of the reference antibody ch-175D10. The binding of hu253C4-N31Q to HEK293-hCLDN18.2 exhibited the mean maximum fluorescence intensity comparable to that of the reference antibody ch-175D10, and $EC_{50}$ was superior to that of the reference antibody ch-175D10.

The binding of hu299B2-S32A and hu253C4-N31Q of the present disclosure to PDX-hCLDN18.2 exhibited a mean maximum fluorescence intensity of 15585-25189, a half binding concentration ($EC_{50}$) of 11.42-29.68 nM, whereas the binding of the reference antibody ch-175D10 to PDX-hCLDN18.2 under the same reaction conditions exhibited a mean maximum fluorescence intensity of only 5703, and a half binding concentration ($EC_{50}$) 24.89 nM. It can be seen that the maximum binding of the humanized antibody of the present disclosure to the native hCLDN18.2 antigen was stronger than that of ch-175D10, and $EC_{50}$ was comparable to that of ch-175D10.

B. Binding Selectivity of Humanized Antibodies

The binding of the humanized antibody of the present disclosure to HEK293-mCLDN18.2 cells and HEK293-hCLDN18.1 cells was examined using FACS according to the method described in Example 4B.

HEK293-mCLDN18.2 and HEK293-hCLDN18.1 cells were harvested separately and resuspended in PBS to adjust cell concentration, and gradiently diluted humanized antibody was added, wherein irrelevant human IgG was used as a negative control and ch-175D10 was still a positive control (reference antibody). Following incubation in a 4° C. shaking table for 50 min, the mixture was centrifugally washed twice with phosphate buffer solution, added with fluorescently labeled anti-human IgG secondary antibody, 100 μL per well; after incubation in a 4° C. shaking table for 40 min, the mixture was centrifugally washed twice with phosphate buffer solution, and then the prepared sample was detected on a flow cytometer; the half binding concentration ($EC_{50}$) and the mean maximum fluorescence intensity (Top MFI) were calculated by GraphPad software, and the results were shown in Table 12.

TABLE 12

Binding of anti-CLDN18.2 humanized antibodies to mCLDN18.2 and hCLDN18.1, respectively

| Clone Number | HEK293-mCLDN18.2 | | HEK293-hCLDN18.1 Binding or not (+/−) |
|---|---|---|---|
| | $EC_{50}$ (μg/mL) | Mean maximum fluorescence intensity (Top MFI) | |
| ch-175D10 | 0.136 | 86407 | − |
| hu299B2-S32A-1 | 0.201 | 88800 | − |
| hu299B2-S32A-2 | 0.111 | 90420 | − |
| hu299B2-S32A-3 | 0.342 | 102785 | − |
| hu299B2-S32A-4 | 0.281 | 84871 | − |
| hu253C4-N31Q-1 | 0.190 | 64998 | − |
| hu253C4-N31Q-2 | 0.026 | 36841 | − |
| hu253C4-N31Q-3 | 0.030 | 42107 | − |

Table 12 showed the affinity results for the humanized antibody of the present disclosure and the reference antibody ch-175D10 to HEK293-mCLDN18.2 cells and HEK293-hCLDN18.1 cells, respectively. Experimental results showed that: the humanized antibody of the present disclosure was the same as the reference antibody ch-175D10, both of which bound to the mCLDN18.2 antigen, wherein the binding of the humanized antibody to HEK293-mCLDN18.2 exhibited a mean maximum fluorescence intensity of 36841-102785 and a half binding concentration ($BC_{50}$) of 0.026-0.342 μg/mL, the binding of the reference antibody ch-175D10 to HEK293-mCLDN18.2 under the same reaction conditions exhibited a mean maximum fluorescence intensity of 86407 and a half binding concentration ($EC_{50}$) of 0.136 μg/mL, indicating that the binding of the humanized antibody to mCLDN18.2 comparable to that of the reference antibody. Moreover, the humanized antibody was the same as the reference antibody ch-175D10, neither binding to the hCLDN18.1 antigen.

Example 9 In Vitro Functional Assay of Humanized Antibodies

A. Antibody-Dependent Cell-Mediated Cytotoxicity (ADCC)

According to the method described in Example 5A, CHO-K1/hCLDN18.2 cells were used as target cells, NK cells transfected with 158V/V type FcγRIIIa gene (NK92/FcRγ3a.158V/V) were used as effector cells, and the release of lactate dehydrogenase (LDH) in cell was detected by the cytotoxicity assay kit (Roche) and used as an indicator of cell killing effect.

The percentage of cell lysis caused by the ADCC effect was calculated using the following formula: % cell lysis=100%×(sample release-target cell/effector cell mixed release)/(maximum release-target cell release), wherein the maximum release was the absorbance value produced in the wells of target cells treated with Triton X-100, the target cell/effector cell mixed release was the absorbance value produced in the wells of target cells and effector cell mixture, and the target cell release was the absorbance value produced in the wells containing only target cells, the sample release was the absorbance values produced in the wells of a humanized antibody, target cells, and effector cells mixture, and EC50 and maximal lysis were calculated by GraphPad software, and the results were shown in Table 13.

TABLE 13

ADCC activity of humanized anti-CLDN18.2 antibodies

| Clone Number | Maximum lysis (%) | $EC_{50}$ (μg/ml) |
|---|---|---|
| ch-175D10 | 51.42/49.15 | 0.047/0.039 |
| hu299B2-S32A-1 | 57.89 | 0.022 |
| hu299B2-S32A-2 | 68.08 | 0.028 |
| hu299B2-S32A-3 | 69.09 | 0.022 |
| hu299B2-S32A-4 | 63.23 | 0.024 |
| hu253C4-N31Q-1 | 54.85 | 0.024 |
| hu253C4-N31Q-2 | 58.80 | 0.037 |
| hu253C4-N31Q-3 | 70.26 | 0.038 |

Figure 34:
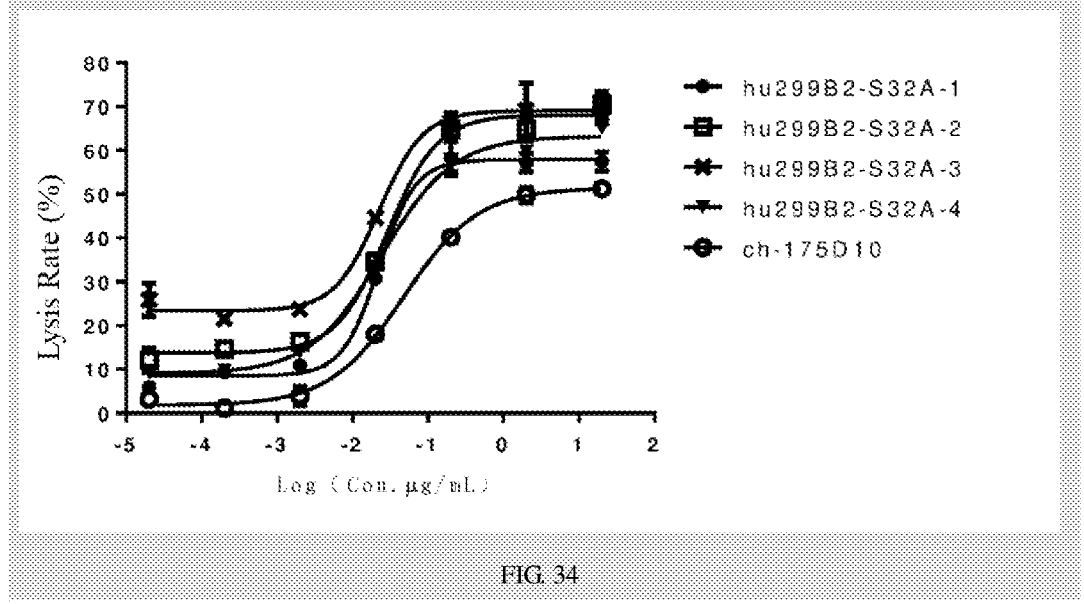
FIG. 34 shows ADCC results of humanized antibody hu299B2-S32A of the present disclosure against CHO-K1 cells stably transfected expressing hCLDN18.2.
Figure 35:
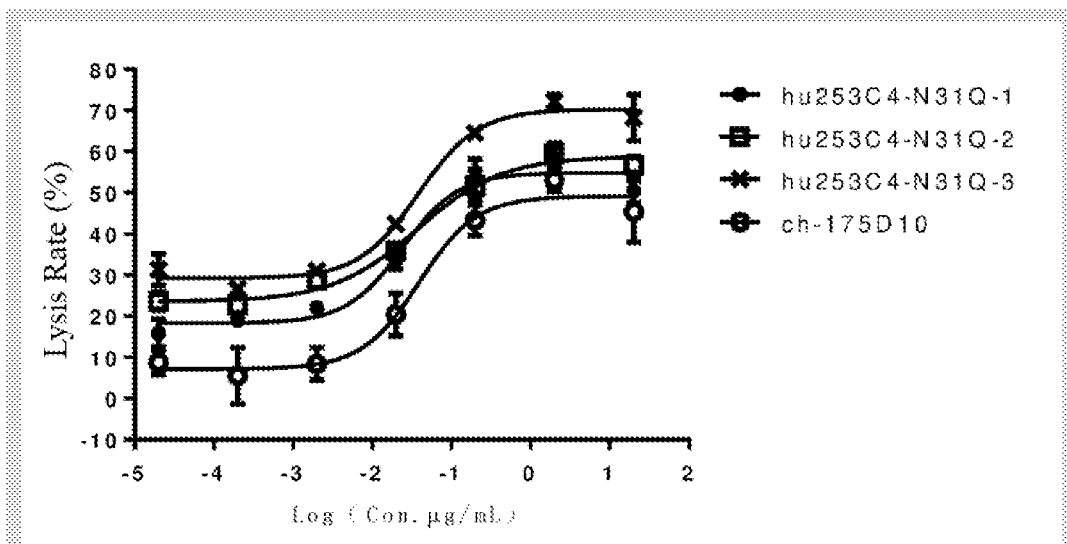
FIG. 35 shows ADCC results of humanized antibody hu253C4-N31Q of the present disclosure against CHO-K1 cells stably transfected expressing hCLDN18.2.

Table 13 and FIGS. 34-35 showed ADCC results for the humanized antibody of the present disclosure and the reference antibody ch-175D10 on CHO-K1/hCLDN18.2 cells. Experimental results showed that the maximal ADCC effect of the humanized antibody of the present disclosure on CHO-K1/hCLDN18.2 cells was 54.85%-70.26%, and the ADCC effect of the reference antibody ch-175D10 was about 50% under the same reaction conditions. The concentration of the humanized antibody of the present disclosure that produces 50% ADCC effect ($EC_{50}$) was 0.022-0.038 μg/mL, and the concentration of ch-175D10 that produces 50% ADCC effect ($EC_{50}$) under the same reaction conditions was 0.040 μg/mL. The above results demonstrated that the humanized antibodies of the present disclosure were comparable to the reference antibody ch-175D10 in ADCC activity.

B. Complement-Dependent Cytotoxicity (CDC)

According to the method described in Example 5B, Cell viability was measured by CellTiter-Glo® chemiluminescent cell viability assay kit (Promega) using CHO-K1/hCLDN18.2 as target cells and pooled normal human serum (PNHS) as complement source, and the results were read using PHERAstar Plus software.

The cell lysis rate caused by the humanized antibody in the CDC assay was calculated using the following formula:

% cell lysis=100%×(1−(test wells-serum control wells)/(cell+serum wells-serum control wells))

The experimental controls are: the serum control wells: only serum (i.e., 30 μL buffer+10 μL diluted serum). Cells+serum wells: serum was added to wells of CHO-K1/hCLDN18.2 cell suspension (i.e., 20 μL cell suspension+10 μL buffer+10 μL diluted serum). Test wells: serum and chimeric antibody were added to wells of CHO-K1/hCLDN18.2 cell suspension (i.e., 20 μL cell suspension+10 μL antibody+10 μL diluted serum).

The $EC_{50}$ and maximum lysis were calculated using GraphPad software, and the results were shown in Table 14.

TABLE 14

CDC activity of humanized anti-CLDN18.2 antibodies

| Clone Number | Maximum lysis (%) | $EC_{50}$ (μg/ml) |
|---|---|---|
| ch-175D10 | 87.76 | 1.549 |
| hu299B2-S32A-1 | 99.15 | 0.125 |
| hu299B2-S32A-2 | 99.74 | 0.129 |

TABLE 14-continued

CDC activity of humanized anti-CLDN18.2 antibodies

| Clone Number | Maximum lysis (%) | EC$_{50}$ (µg/ml) |
|---|---|---|
| hu299B2-S32A-3 | 99.83 | 0.092 |
| hu299B2-S32A-4 | 99.87 | 0.123 |
| hu253C4-N31Q-1 | 96.29 | 0.175 |
| hu253C4-N31Q-2 | 97.51 | 0.149 |
| hu253C4-N31Q-3 | 96.11 | 0.128 |

Figure 36:
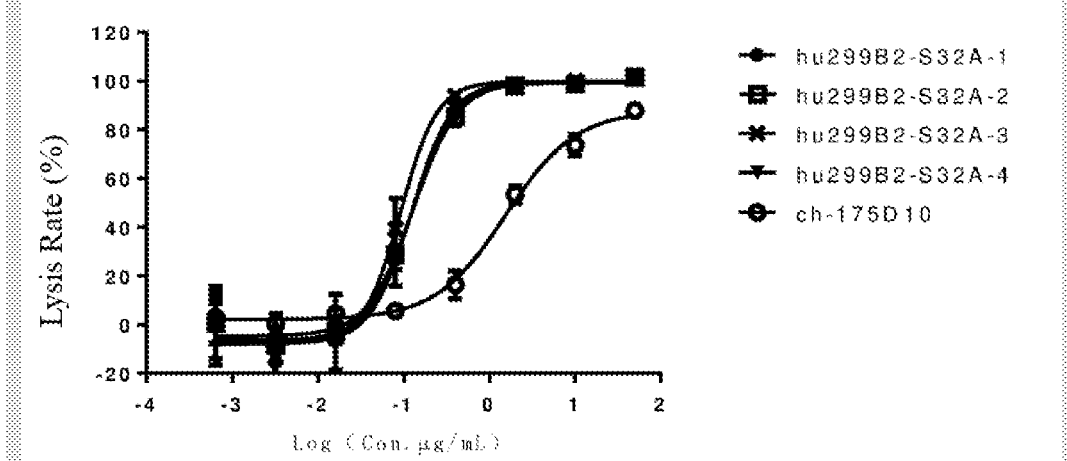
FIG. 36 shows the CDC results of humanized antibody hu299B2-S32A of the present disclosure against CHO-K1 cells stably transfected expressing hCLDN18.2.
Figure 37:
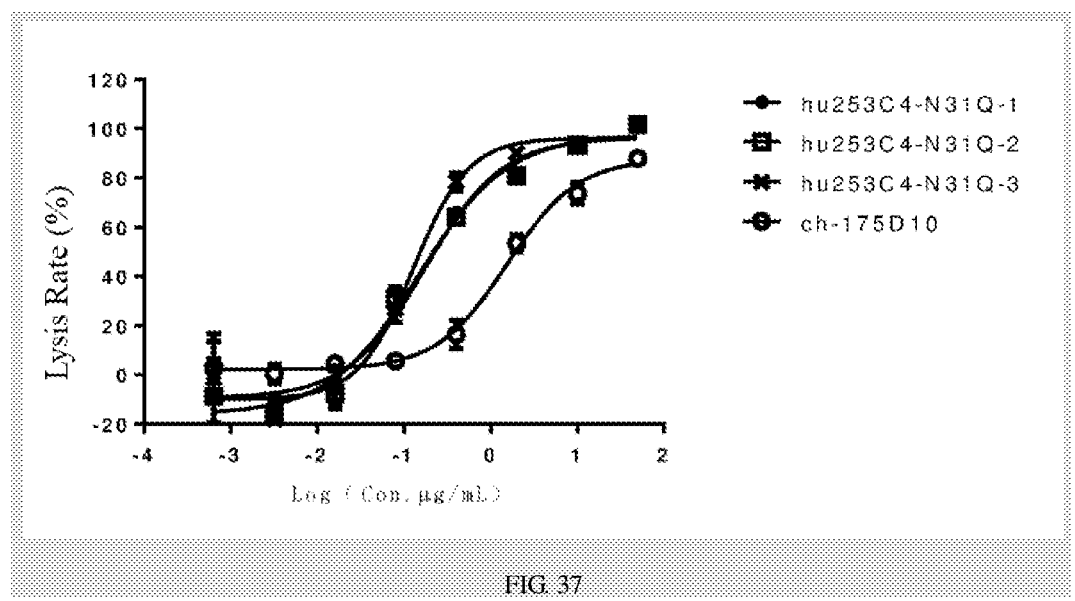
FIG. 37 shows the CDC results of humanized antibody hu253C4-N31Q of the present disclosure against CHO-K1 cells stably transfected expressing hCLDN18.2.

Table 14 and FIGS. 36-37 showed CDC results for the humanized antibody of the present disclosure and the reference antibody ch-175D10 on CHO-K1/hCLDN18.2 cells. Experimental results showed that: the maximal CDC effect of the humanized antibody of the present disclosure on CHO-K1/hCLDN18.2 cells was 96.11%-99.87%, and the maximal CDC effect of the reference antibody ch-175D10 was 87.76% under the same reaction conditions. The concentration of the chimeric antibody of the present disclosure that produces 50% CDC effect (EC$_{50}$) was 0.092-0.175 µg/mL, and the concentration of ch-175D10 that produces 50% CDC effect (EC$_{50}$) under the same reaction conditions was higher than 1 µg/mL. It can be seen that the CDC activity of all the humanized antibodies was stronger than that of the reference antibody.

The embodiments of the present disclosure described above are intended to be merely exemplary, and equivalents of numerous specific compounds, materials, and operations may be recognized or determined by one skilled in the art without undue experimentation. All such equivalents are intended to be within the scope of the present disclosure and are encompassed by the claims.

What is claimed is:

1. An anti-CLDN18.2 antibody or antigen-binding fragment thereof, comprising a heavy chain variable region and a light chain variable region, the heavy chain variable region comprising an HCDR1, an HCDR2, and an HCDR3 and the light chain variable region comprising an LCDR1, an LCDR2, and an LCDR3 selected from the group consisting of:
(1) SEQ ID NOs: 37, 38, 39, 86, 93, 97;
(2) SEQ ID NOs: 40, 41, 42, 87, 94, 98;
(3) SEQ ID NOs: 43, 41, 44, 88, 93, 99;
(4) SEQ ID NOs: 45, 46, 47, 87, 95, 100;
(5) SEQ ID NOs: 37, 48, 39, 88, 93, 97;
(6) SEQ ID NOs: 49, 50, 51, 88, 93, 101;
(7) SEQ ID NOs: 49, 52, 51, 89, 93, 102;
(8) SEQ ID NOs: 53, 54, 55, 88, 93, 100;
(9) SEQ ID NOs: 56, 57, 58, 90, 93, 103;
(10) SEQ ID NOs: 59, 60, 61, 91, 96, 104;
(11) SEQ ID NOs: 62, 63, 64, 88, 93, 98;
(12) SEQ ID NOs: 65, 66, 67, 92, 93, 105;
(13) SEQ ID NOs: 68, 69, 70, 88, 93, 106;
(14) SEQ ID NOs: 71, 72, 73, 88, 93, 107;
(15) SEQ ID NOs: 74, 75, 76, 88, 93, 106;
(16) SEQ ID NOs: 77, 78, 79, 87, 93, 108;
(17) SEQ ID NOs: 80, 81, 82, 88, 93, 109;
(18) SEQ ID NOs: 83, 84, 85, 88, 93, 110;
(19) SEQ ID NOs: 71, 72, 73, 112, 93, 107;
(20) SEQ ID NOs: 71, 72, 73, 113, 93, 107;
(21) SEQ ID NOs: 83, 84, 85, 111, 93, 110;
(22) SEQ ID NOs: 83, 84, 85, 112, 93, 110; and
(23) SEQ ID NOs: 83, 84, 85, 113, 93, 110;
wherein the HCDR1, HCDR2, HCDR3, LCDR1, LCDR2, and LCDR3 are arranged in the order of HCDR1, HCDR2, HCDR3, LCDR1, LCDR2, LCDR3 in each group.

2. The anti-CLDN18.2 antibody or antigen-binding fragment thereof of claim 1, comprising at least 80% to 100% sequence identity to a heavy chain variable region and a light chain variable region of any one of the groups consisting of:
(1) SEQ ID NOs: 1 and 2;
(2) SEQ ID NOs: 3 and 4;
(3) SEQ ID NOs: 5 and 6;
(4) SEQ ID NOs: 7 and 8;
(5) SEQ ID NOs: 9 and 10;
(6) SEQ ID NOs: 11 and 12;
(7) SEQ ID NOs: 13 and 14;
(8) SEQ ID NOs: 15 and 16;
(9) SEQ ID NOs: 17 and 18;
(10) SEQ ID NOs: 19 and 20;
(11) SEQ ID NOs: 21 and 22;
(12) SEQ ID NOs: 23 and 24;
(13) SEQ ID NOs: 25 and 26;
(14) SEQ ID NOs: 27 and 28;
(15) SEQ ID NOs: 29 and 30;
(16) SEQ ID NOs: 31 and 32;
(17) SEQ ID NOs: 33 and 34;
(18) SEQ ID NOs: 35 and 36;
(19) SEQ ID NOs: 27 and 115;
(20) SEQ ID NOs: 27 and 116;
(21) SEQ ID NOs: 35 and 117;
(22) SEQ ID NOs: 35 and 118;
(23) SEQ ID NOs: 35 and 119;
(24) SEQ ID NOs: 120 and 121;
(25) SEQ ID NOs: 120 and 123;
(26) SEQ ID NOs: 120 and 124;
(27) SEQ ID NOs: 122 and 121;
(28) SEQ ID NOs: 125 and 126;
(29) SEQ ID NOs: 125 and 127; and
(30) SEQ ID NOs: 128 and 126.

3. The anti-CLDN18.2 antibody or antigen-binding fragment thereof of claim 1, which is a murine antibody, a chimeric antibody, or a humanized antibody.

4. The anti-CLDN18.2 antibody or antigen-binding fragment thereof of claim 1, further comprising a heavy chain constant region and/or light chain constant region, optionally wherein the heavy chain constant region comprises an FC or a variant Fc.

5. A conjugate formed by coupling the anti-CLDN18.2 antibody or antigen-binding fragment thereof of claim 1 to a capture label or a detection label, the detection label comprising radionuclides, luminescent substances, colored substances, or enzymes.

6. A multispecific antibody, wherein one antigen-binding domain comprises the anti-CLDN18.2 antibody or antigen-binding fragment thereof of claim 1.

7. The multispecific antibody of claim 6, which is a bispecific antibody.

8. An antibody-drug conjugate, comprising the anti-CLDN18.2 antibody or antigen-binding fragment thereof of claim 1, the antibody-drug conjugate being formed by antibody-linker-toxin interconnections.

9. A chimeric antigen receptor, comprising an extracellular recognition unit comprising the anti-CLDN18.2 antibody or antigen-binding fragment thereof of claim 1.

10. A nucleic acid encoding the anti-CLDN18.2 antibody or antigen binding fragment thereof claim 1.

11. A recombinant vector comprising a nucleic acid encoding the anti-CLDN18.2 antibody or antigen-binding fragment thereof of claim 1.

12. A host cell comprising a nucleic acid encoding the anti-CLDN18.2 antibody or antigen-binding fragment thereof of claim 1 being integrated into the genome or comprising a recombinant vector comprising a nucleic acid encoding the anti-CLDN18.2 antibody or antigen-binding fragment thereof of claim 1.

13. A method of preparing the anti-CLDN18.2 antibody or antigen binding fragment thereof of claim 1, comprising: culturing one or more host cells comprising a nucleic acid encoding the anti-CLDN18.2 antibody or antigen-binding fragment thereof according to claim 1, or culturing one or more host cells comprising a recombinant vector comprising a nucleic acid encoding the anti-CLDN18.2 antibody or antigen-binding fragment thereof according to claim 1 under suitable conditions and purifying the expression products from the cells.

14. A pharmaceutical composition comprising an effective amount of the anti-CLDN18.2 antibody or antigen-binding fragment thereof of claim 1, or comprising an effective amount of a multispecific or bispecific antibody wherein one antigen-binding domain of the multispecific or bispecific antibody comprises the anti-CLDN18.2 antibody or antigen-binding fragment thereof of claim 1, or comprising an effective amount of an antibody-drug conjugate comprising the anti-CLDN18.2 antibody or antigen binding fragment thereof of claim 1, or comprising an effective amount of a chimeric antigen receptor comprising an extracellular recognition unit comprising the anti-CLDN18.2 antibody or antigen-binding fragment thereof of claim 1, or comprising an effective amount of a nucleic acid encoding the anti-CLDN18.2 antibody or antigen-binding fragment thereof of claim 1, or comprising an effective amount of a recombinant vector comprising a nucleic acid encoding the anti-CLDN18.2 antibody or antigen-binding fragment thereof according to claim 1, or comprising an effective amount of a host cell comprising a recombinant vector comprising a nucleic acid encoding the anti-CLDN18.2 antibody or antigen-binding fragment thereof according to claim 1, or comprising an effective amount of a host cell comprising a nucleic acid encoding the anti-CLDN18.2 antibody or antigen-binding fragment thereof according to claim 1 being integrated into the genome the pharmaceutical composition further comprises a pharmaceutically acceptable carrier or one or more additional therapeutic agents.

15. A method of inducing cell death of CLDN18.2-expressing cells, comprising contacting the cells with the pharmaceutical composition of claim 14.

16. A method of treating a disease associated with expression of CLDN18.2 in a subject, comprising administering to a subject in need thereof the pharmaceutical composition of claim 14, optionally wherein the method further comprises administering to the subject in need an additional therapeutic agent.

17. The method of claim 16, wherein the disease is a tumor; and wherein the additional therapeutic agent comprises one or more selected from the group consisting of: chemotherapeutic agents, cytotoxic agents, radiotherapeutic agents, cancer vaccines, anti-neoplastic agents, targeted anti-cancer agents, anti-angiogenic agents, biological response modifiers, cytokines, hormones, anti-metastatic agents, immunotherapeutic agents, oncolytic viruses, and protease inhibitors.

18. The method of claim 16, wherein the disease is gastric cancer, esophageal cancer, intestinal cancer, pancreatic cancer, nephroblastoma, lung cancer, ovarian cancer, colon cancer, rectal cancer, liver cancer, head and neck cancer, chronic myelogenous leukemia, or gallbladder cancer.

* * * * *

```
                        SEQUENCE LISTING

<160> NUMBER OF SEQ ID NOS: 128

<210> SEQ ID NO 1
<211> LENGTH: 119
<212> TYPE: PRT
<213> ORGANISM: Artificial Sequence
<220> FEATURE:
<223> OTHER INFORMATION: Synthetic construct

<400> SEQUENCE: 1

Gln Val Gln Leu Gln Gln Ser Gly Ala Glu Leu Met Lys Pro Gly Ala
1               5                   10                  15

Ser Val Lys Leu Pro Cys Lys Ala Ser Gly Tyr Thr Leu Thr Gly Tyr
            20                  25                  30

Trp Ile Glu Trp Leu Lys Gln Arg Pro Arg His Gly Leu Glu Trp Ile
        35                  40                  45

Gly Glu Ile Leu Leu Gly Ser Gly Ser Ile Lys Tyr Asn Val Lys Phe
    50                  55                  60

Lys Asp Lys Ala Thr Phe Thr Ala Asp Thr Ser Ser Asn Thr Ala Tyr
65                  70                  75                  80

Met Gln Leu Asn Ser Leu Thr Thr Glu Asp Ser Ala Ile Tyr Tyr Cys
                85                  90                  95

Ala Arg Lys Gly Leu Arg Gly Asn Ser Phe Asp Tyr Trp Gly Gln Gly
            100                 105                 110

Thr Thr Leu Thr Val Ser Ser
        115

<210> SEQ ID NO 2
<211> LENGTH: 113
<212> TYPE: PRT
<213> ORGANISM: Artificial Sequence
<220> FEATURE:
<223> OTHER INFORMATION: Synthetic construct

<400> SEQUENCE: 2

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Arg Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Tyr Tyr Pro Phe Thr Phe Gly Ser Gly Thr Lys Leu Glu Ile
            100                 105                 110

Lys

<210> SEQ ID NO 3
<211> LENGTH: 118
<212> TYPE: PRT
<213> ORGANISM: Artificial Sequence
<220> FEATURE:
<223> OTHER INFORMATION: Synthetic construct

<400> SEQUENCE: 3

Gln Val Gln Leu Gln Gln Pro Gly Ala Glu Leu Val Lys Pro Gly Thr
  1               5                  10                  15

Ser Val Lys Leu Ser Cys Lys Ala Ser Gly Tyr Ile Phe Thr Asn Tyr
                 20                  25                  30

Trp Thr His Trp Met Lys Gln Arg Pro Gly Gln Gly Leu Glu Trp Ile
             35                  40                  45

Gly Met Ile His Pro Asn Ser Gly Ser Ser Asn Tyr Asn Glu Lys Phe
         50                  55                  60

Lys Ser Lys Ala Thr Leu Thr Val Asp Arg Ser Ser Ser Thr Val Tyr
 65                  70                  75                  80

Met Gln Leu Arg Arg Leu Thr Ser Glu Asp Ser Ala Val Tyr Tyr Cys
                 85                  90                  95

Thr Arg Ile His Tyr Gly Asn Ser Met Asp Tyr Trp Gly Gln Gly Thr
            100                 105                 110

Ser Val Thr Val Ser Ser
        115

<210> SEQ ID NO 4
<211> LENGTH: 113
<212> TYPE: PRT
<213> ORGANISM: Artificial Sequence
<220> FEATURE:
<223> OTHER INFORMATION: Synthetic construct

<400> SEQUENCE: 4

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Phe Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Trp Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Ala Tyr Ser Tyr Pro Phe Thr Phe Gly Ser Gly Thr Lys Leu Glu Ile
            100                 105                 110

Lys
```

```
<210> SEQ ID NO 5
<211> LENGTH: 118
<212> TYPE: PRT
<213> ORGANISM: Artificial Sequence
<220> FEATURE:
<223> OTHER INFORMATION: Synthetic construct

<400> SEQUENCE: 5

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Ser Tyr
                20                  25                  30

Trp Thr His Trp Val Lys Gln Arg Pro Gly Gln Gly Leu Glu Trp Ile
            35                  40                  45

Gly Met Ile His Pro Asn Ser Gly Ser Ser Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Arg Arg Leu Thr Ser Glu Asp Ser Ala Val Tyr Tyr Cys
                85                  90                  95

Thr Arg Ile His Tyr Gly Asn Ala Met Asp Tyr Trp Gly Gln Gly Thr
            100                 105                 110

Ser Val Thr Val Ser Ser
            115

<210> SEQ ID NO 6
<211> LENGTH: 113
<212> TYPE: PRT
<213> ORGANISM: Artificial Sequence
<220> FEATURE:
<223> OTHER INFORMATION: Synthetic construct

<400> SEQUENCE: 6

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Asp Tyr Ser Phe Pro Phe Thr Phe Gly Ser Gly Thr Lys Leu Glu Ile
            100                 105                 110

Lys

<210> SEQ ID NO 7
<211> LENGTH: 118
<212> TYPE: PRT
<213> ORGANISM: Artificial Sequence
<220> FEATURE:
<223> OTHER INFORMATION: Synthetic construct

<400> SEQUENCE: 7

Gln Val Gln Leu Gln Gln Pro Gly Thr Glu Leu Val Lys Pro Gly Ala
1               5                   10                  15
```

Ser Val Lys Leu Ser Cys Lys Ala Ser Gly Tyr Thr Phe Thr Asn Tyr
        20                  25                  30

Trp Met His Trp Val Lys Gln Arg Pro Gly His Gly Leu Glu Trp Ile
            35                  40                  45

Gly Met Ile His Pro Asn Ser Tyr Ser Thr Asn Tyr Asn Glu Lys Phe
    50                  55                  60

Arg Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Ile Tyr Tyr Gly Asn Ala Met Asp Tyr Trp Gly Gln Gly Thr
            100                 105                 110

Ser Val Thr Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: Synthetic construct

<400> SEQUENCE: 8

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Phe Asn Ser
            20                  25                  30

Gly Asn Gln Lys Asn Tyr Leu Thr Trp Tyr His Gln Lys Pro Gly Gln
        35                  40                  45

Pro Pro Lys Leu Leu Ile Tyr Trp Ala Phe Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Arg Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 9
<211> LENGTH: 119
<212> TYPE: PRT
<213> ORGANISM: Artificial Sequence
<220> FEATURE:
<223> OTHER INFORMATION: Synthetic construct

<400> SEQUENCE: 9

Gln Val Gln Leu Gln Gln Ser Gly Ala Glu Leu Met Lys Pro Gly Ala
1               5                   10                  15

Ser Val Lys Leu Ser Cys Lys Ala Ser Gly Tyr Thr Phe Thr Gly Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Ser Ile Lys Tyr Asn Glu Lys Phe
    50                  55                  60

Lys Asp Lys Ala Thr Phe Thr Ala Asp Thr Ser Ser Asn Thr Ala Tyr
65                  70                  75                  80

```
Met Gln Leu Ser Ser Leu Thr Thr Glu Asp Ser Ala Ile Tyr Tyr Cys
                85                  90                  95

Ala Arg Lys Gly Leu Arg Gly Asn Ser Phe Asp Tyr Trp Gly Gln Gly
           100                 105                 110

Thr Thr Leu Thr Val Ser Ser
        115

<210> SEQ ID NO 10
<211> LENGTH: 113
<212> TYPE: PRT
<213> ORGANISM: Artificial Sequence
<220> FEATURE:
<223> OTHER INFORMATION: Synthetic construct

<400> SEQUENCE: 10

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Arg Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Phe Thr Phe Gly Ser Gly Thr Lys Leu Glu Ile
            100                 105                 110

Lys

<210> SEQ ID NO 11
<211> LENGTH: 118
<212> TYPE: PRT
<213> ORGANISM: Artificial Sequence
<220> FEATURE:
<223> OTHER INFORMATION: Synthetic construct

<400> SEQUENCE: 11

Glu Val His Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

His Met Asn Trp Val Lys Gln Ser His Gly Lys Ser Leu Glu Trp Ile
        35                  40                  45

Gly Val Ile Asn Pro Tyr Asn Gly Gly Ile Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Thr Ile Tyr Tyr Gly Asn Ser Phe Ala Tyr Trp Gly Gln Gly Thr
            100                 105                 110

Leu Val Thr Val Ser Ala
        115

<210> SEQ ID NO 12
```

```
<211> LENGTH: 113
<212> TYPE: PRT
<213> ORGANISM: Artificial Sequence
<220> FEATURE:
<223> OTHER INFORMATION: Synthetic construct

<400> SEQUENCE: 12
```

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Phe Thr Phe Gly Gly Gly Thr Lys Leu Glu Ile
            100                 105                 110

Arg

```
<210> SEQ ID NO 13
<211> LENGTH: 118
<212> TYPE: PRT
<213> ORGANISM: Artificial Sequence
<220> FEATURE:
<223> OTHER INFORMATION: Synthetic construct

<400> SEQUENCE: 13
```

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Ser Asp Tyr
            20                  25                  30

His Met Asn Trp Val Lys Gln Ser His Gly Lys Ser Leu Glu Trp Val
        35                  40                  45

Gly Leu Ile Asn Pro Tyr Asn Gly Gly Ile Arg Phe Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Thr Ile Tyr Tyr Gly Asn Ser Phe Ala Tyr Trp Gly Gln Gly Thr
            100                 105                 110

Leu Val Thr Val Ser Ala
        115

```
<210> SEQ ID NO 14
<211> LENGTH: 113
<212> TYPE: PRT
<213> ORGANISM: Artificial Sequence
<220> FEATURE:
<223> OTHER INFORMATION: Synthetic construct

<400> SEQUENCE: 14
```

Asp Ile Val Met Thr Gln Ser Pro Ser Ser Leu Thr Val Thr Ala Gly
1               5                   10                  15

Glu Lys Val Thr Leu Thr Cys Lys Ser Gly Gln Ser Leu Leu Asn Ser

```
                20                  25                  30
Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Gly Val Gln Ala Glu Asp Leu Ala Val Tyr Tyr Cys Gln Asn
                85                  90                  95

Asp Tyr Phe Tyr Pro Tyr Thr Phe Gly Gly Gly Thr Lys Leu Glu Ile
            100                 105                 110

Lys

<210> SEQ ID NO 15
<211> LENGTH: 118
<212> TYPE: PRT
<213> ORGANISM: Artificial Sequence
<220> FEATURE:
<223> OTHER INFORMATION: Synthetic construct

<400> SEQUENCE: 15

Gln Val Gln Leu Gln Gln Ser Gly Ala Gly Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Ile Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Phe
65                  70                  75                  80

Met Gln Leu Ser Ser Leu Thr Ser Glu Asp Ser Ala Val Tyr Phe Cys
                85                  90                  95

Thr Arg Ile Tyr Tyr Gly Asn Ala Phe Ala Tyr Trp Gly Gln Gly Thr
            100                 105                 110

Leu Val Thr Val Ser Ala
        115

<210> SEQ ID NO 16
<211> LENGTH: 113
<212> TYPE: PRT
<213> ORGANISM: Artificial Sequence
<220> FEATURE:
<223> OTHER INFORMATION: Synthetic construct

<400> SEQUENCE: 16

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
```

Asp Tyr Ser Tyr Pro Phe Thr Phe Gly Ser Gly Thr Lys Leu Glu Ile
            85                  90                  95

Lys
            100                 105                 110

<210> SEQ ID NO 17
<211> LENGTH: 118
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Gln Met Asn Trp Val Lys Gln Ser His Gly Lys Ser Leu Glu Trp Ile
        35                  40                  45

Gly Phe Ile Asn Pro Tyr Asn Gly Gly Ile Arg Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Thr Ile Tyr Phe Gly Asn Ser Phe Ala Asn Trp Gly Gln Gly Thr
            100                 105                 110

Leu Val Thr Val Ser Ala
        115

<210> SEQ ID NO 18
<211> LENGTH: 113
<212> TYPE: PRT
<213> ORGANISM: Artificial Sequence
<220> FEATURE:
<223> OTHER INFORMATION: Synthetic construct

<400> SEQUENCE: 18

Asp Ile Val Met Thr Gln Ser Pro Ser Ser Leu Thr Val Thr Ala Gly
1               5                   10                  15

Glu Lys Val Thr Met Ser Cys Lys Pro Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Tyr Pro Tyr Thr Phe Gly Gly Gly Thr Asn Leu Glu Ile
            100                 105                 110

Lys

<210> SEQ ID NO 19
<211> LENGTH: 117
<212> TYPE: PRT
<213> ORGANISM: Artificial Sequence

```
<220> FEATURE:
<223> OTHER INFORMATION: Synthetic construct

<400> SEQUENCE: 19

Gln Val Gln Leu Lys Glu Ser Gly Pro Gly Leu Val Ala Pro Ser Gln
1               5                   10                  15

Ser Leu Ser Ile Thr Cys Thr Val Ser Glu Phe Ser Leu Thr Thr Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ser Ile Ser Lys Asp Thr Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Pro Gly Leu Arg Asn Ala Met Asp Tyr Trp Gly Gln Gly Thr Ser
            100                 105                 110

Val Thr Val Ser Ser
        115

<210> SEQ ID NO 20
<211> LENGTH: 113
<212> TYPE: PRT
<213> ORGANISM: Artificial Sequence
<220> FEATURE:
<223> OTHER INFORMATION: Synthetic construct

<400> SEQUENCE: 20

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Leu Ile Tyr Pro Leu Thr Phe Gly Ala Gly Thr Lys Leu Glu Leu
            100                 105                 110

Lys

<210> SEQ ID NO 21
<211> LENGTH: 118
<212> TYPE: PRT
<213> ORGANISM: Artificial Sequence
<220> FEATURE:
<223> OTHER INFORMATION: Synthetic construct

<400> SEQUENCE: 21

Gln Val Gln Leu Gln Gln Ser Gly Pro Glu Leu Val Arg Pro Gly Val
1               5                   10                  15

Ser Val Lys Ile Ser Cys Lys Gly Ser Ser Tyr Thr Phe Thr Asp Tyr
            20                  25                  30

Thr Met His Trp Val Lys Gln Ser His Ala Lys Ser Leu Glu Trp Ile
```

```
                35                  40                  45
Gly Phe Ile Gly Val Tyr Tyr Gly Asn Thr Asn Tyr Asn Gln Lys Phe
 50                  55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Val Tyr Tyr Cys
                 85                  90                  95

Ala Arg Ile Gly Arg Gly Asn Ala Met Asp Tyr Trp Gly Gln Gly Thr
                100                 105                 110

Ser Val Thr Val Ser Ser
        115

<210> SEQ ID NO 22
<211> LENGTH: 113
<212> TYPE: PRT
<213> ORGANISM: Artificial Sequence
<220> FEATURE:
<223> OTHER INFORMATION: Synthetic construct

<400> SEQUENCE: 22

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Asn Cys Gln Asn
                 85                  90                  95

Ala Tyr Ser Tyr Pro Phe Thr Phe Gly Ser Gly Thr Lys Leu Glu Ile
                100                 105                 110

Lys

<210> SEQ ID NO 23
<211> LENGTH: 118
<212> TYPE: PRT
<213> ORGANISM: Artificial Sequence
<220> FEATURE:
<223> OTHER INFORMATION: Synthetic construct

<400> SEQUENCE: 23

Asp Val Gln Leu Gln Glu Ser Gly Pro Asp Leu Val Lys Pro Ser Gln
 1               5                  10                  15

Ser Leu Ser Leu Ile Cys Thr Val Thr Gly Tyr Ser Ile Thr Ser Gly
                 20                  25                  30

Tyr Ser Trp His Trp Ile Arg Gln Phe Pro Gly Asn Lys Leu Glu Trp
                 35                  40                  45

Met Gly Tyr Ile His Tyr Ser Gly Gly Thr Asn Tyr Asn Pro Ser Leu
 50                  55                  60

Lys Ser Arg Ile Ser Phe Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Leu Glu Arg Gly Asn Ser Phe Ala Tyr Trp Gly Gln Gly Thr
```

Leu Val Thr Val Ser Ala
        115

<210> SEQ ID NO 24
<211> LENGTH: 113
<212> TYPE: PRT
<213> ORGANISM: Artificial Sequence
<220> FEATURE:
<223> OTHER INFORMATION: Synthetic construct

<400> SEQUENCE: 24

Asp Ile Val Met Thr Gln Ser Pro Ser Ser Leu Thr Val Thr Ala Gly
1               5                   10                  15

Glu Lys Val Thr Met Ser Cys Lys Ser Thr Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Phe Tyr Pro Phe Thr Phe Gly Ser Gly Thr Lys Leu Glu Ile
            100                 105                 110

Lys

<210> SEQ ID NO 25
<211> LENGTH: 118
<212> TYPE: PRT
<213> ORGANISM: Artificial Sequence
<220> FEATURE:
<223> OTHER INFORMATION: Synthetic construct

<400> SEQUENCE: 25

Glu Ile Gln Leu Val Glu Ser Gly Gly Gly Leu Val Arg Pro Gly Gly
1               5                   10                  15

Ser Leu Lys Leu Ser Cys Ala Ala Ser Gly Phe Ser Phe Lys Asn Tyr
            20                  25                  30

Val Met Ser Trp Val Arg Gln Ser Pro Glu Arg Arg Leu Glu Trp Val
        35                  40                  45

Ala Glu Ile Arg Thr Gly Gly Asp Tyr Thr Tyr Tyr Val Asp Thr Val
    50                  55                  60

Thr Gly Arg Phe Thr Ile Ser Arg Asp Asn Ala Lys Asn Thr Leu Tyr
65                  70                  75                  80

Leu Glu Met Thr Ser Leu Arg Ser Glu Asp Thr Ala Thr Tyr Tyr Cys
                85                  90                  95

Ala Arg Val Gly Tyr Gly Asn Ser Leu Asp Tyr Trp Gly Gln Gly Thr
            100                 105                 110

Thr Leu Thr Val Ser Ser
        115

<210> SEQ ID NO 26
<211> LENGTH: 113
<212> TYPE: PRT
<213> ORGANISM: Artificial Sequence
<220> FEATURE:
<223> OTHER INFORMATION: Synthetic construct

<400> SEQUENCE: 26

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Ser Cys Gln Asn
                85                  90                  95

Asn Tyr Phe Tyr Pro Leu Thr Phe Gly Ala Gly Thr Glu Leu Glu Leu
            100                 105                 110

Lys

<210> SEQ ID NO 27
<211> LENGTH: 120
<212> TYPE: PRT
<213> ORGANISM: Artificial Sequence
<220> FEATURE:
<223> OTHER INFORMATION: Synthetic construct

<400> SEQUENCE: 27

Gln Val Gln Leu Lys Gln Ser Gly Pro Glu Leu Val Arg Pro Gly Ala
1               5                   10                  15

Ser Val Lys Leu Ser Cys Lys Thr Ser Gly Tyr Ile Phe Thr Asn Tyr
            20                  25                  30

Trp Ile His Trp Val Lys Gln Arg Ser Gly Gln Gly Leu Glu Trp Val
        35                  40                  45

Val Arg Ile Tyr Pro Gly Thr Gly Asn Thr Tyr Tyr Asn Glu Lys Phe
    50                  55                  60

Thr Gly Lys Ala Thr Leu Thr Ala Asp Lys Ser Ser Ser Thr Ala Tyr
65                  70                  75                  80

Met Gln Leu Ser Ser Leu Lys Tyr Glu Asp Ser Ala Val Tyr Phe Cys
                85                  90                  95

Ser Arg Glu Gly Tyr Gly Lys Gly Asn Ser Met Asp Tyr Trp Gly Gln
            100                 105                 110

Gly Thr Ser Val Thr Val Ser Ser
        115                 120

<210> SEQ ID NO 28
<211> LENGTH: 113
<212> TYPE: PRT
<213> ORGANISM: Artificial Sequence
<220> FEATURE:
<223> OTHER INFORMATION: Synthetic construct

<400> SEQUENCE: 28

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Gly Asn Gln Lys Asn Tyr Leu Trp Tyr Gln Gln Lys Pro Gly Gln
        35                  40                  45

```
Pro Pro Lys Leu Leu Phe Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr His Cys Gln Asn
                85                  90                  95
Ala Tyr Tyr Tyr Pro Tyr Thr Phe Gly Gly Gly Thr Lys Leu Glu Met
            100                 105                 110
Lys

<210> SEQ ID NO 29
<211> LENGTH: 118
<212> TYPE: PRT
<213> ORGANISM: Artificial Sequence
<220> FEATURE:
<223> OTHER INFORMATION: Synthetic construct

<400> SEQUENCE: 29

Glu Val Gln Leu Gln Gln Ser Gly Pro Glu Leu Glu Lys Pro Gly Ala
1               5                   10                  15
Ser Val Lys Ile Ser Cys Lys Ala Ser Gly Tyr Ser Phe Thr Ala Tyr
                20                  25                  30
Asn Met Asn Trp Val Arg Gln Arg Asn Gly Lys Ser Leu Glu Trp Ile
            35                  40                  45
Gly Asn Ile Asp Pro Tyr Tyr Gly Gly Thr Asn Tyr Asn Gln Lys Phe
        50                  55                  60
Lys Gly Lys Ala Thr Leu Thr Val Asp Lys Ser Ser Ser Thr Ala Tyr
65                  70                  75                  80
Met Gln Leu Lys Ser Leu Thr Ser Glu Asp Ser Ala Val Tyr Phe Cys
                85                  90                  95
Ala Thr Val Tyr Tyr Gly Asn Ser Leu Ile Tyr Trp Gly Gln Gly Thr
            100                 105                 110
Leu Val Thr Val Ser Ala
        115

<210> SEQ ID NO 30
<211> LENGTH: 113
<212> TYPE: PRT
<213> ORGANISM: Artificial Sequence
<220> FEATURE:
<223> OTHER INFORMATION: Synthetic construct

<400> SEQUENCE: 30

Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
                20                  25                  30
Gly Asn Gln Lys Asn Tyr Leu Thr Trp Tyr Gln Gln Lys Pro Gly Gln
            35                  40                  45
Pro Pro Lys Leu Leu Ile Tyr Trp Ala Ser Thr Arg Glu Ser Gly Val
        50                  55                  60
Pro Asp Arg Phe Thr Gly Thr Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asn Tyr Phe Tyr Pro Leu Thr Phe Gly Ala Gly Thr Gln Leu Glu Leu
            100                 105                 110
```

Lys

```
<210> SEQ ID NO 31
<211> LENGTH: 120
<212> TYPE: PRT
<213> ORGANISM: Artificial Sequence
<220> FEATURE:
<223> OTHER INFORMATION: Synthetic construct

<400> SEQUENCE: 31
```

Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Thr Phe Thr Thr Phe
            20                  25                  30

Trp Ile His Trp Ile Lys Gln Arg Ser Gly Gln Gly Leu Glu Trp Ile
        35                  40                  45

Ala Lys Ile Tyr Pro Gly Thr Gly Tyr Thr Tyr Tyr Asn Glu Lys Phe
    50                  55                  60

Lys Gly Lys Ala Thr Leu Thr Ala Asp Lys Ser Ser Ala Ala Tyr
65                  70                  75                  80

Met Gln Leu Ser Ser Leu Lys Ser Glu Asp Ser Ala Val Tyr Phe Cys
                85                  90                  95

Ala Arg Glu Gly Tyr Gly Lys Gly Asn Ala Val Asp Phe Trp Gly Gln
            100                 105                 110

Gly Ser Ser Val Thr Val Ser Ser
        115                 120

```
<210> SEQ ID NO 32
<211> LENGTH: 113
<212> TYPE: PRT
<213> ORGANISM: Artificial Sequence
<220> FEATURE:
<223> OTHER INFORMATION: Synthetic construct

<400> SEQUENCE: 32
```

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asp Ser Val Gln Ala Glu Asp Leu Ala Val Tyr Tyr Cys Gln Asn
                85                  90                  95

Asp Tyr Thr Tyr Pro Ser Thr Phe Gly Gly Gly Thr Asn Leu Glu Ile
            100                 105                 110

Lys

```
<210> SEQ ID NO 33
<211> LENGTH: 118
<212> TYPE: PRT
<213> ORGANISM: Artificial Sequence
<220> FEATURE:
<223> OTHER INFORMATION: Synthetic construct

<400> SEQUENCE: 33
```

-continued

Gln Ile Gln Leu Val Gln Ser Gly Pro Glu Leu Lys Arg Pro Gly Glu
1               5                   10                  15

Thr Val Arg Ile Ser Cys Lys Ala Ser Gly Phe Thr Thr Thr Ala
            20                  25                  30

Gly Met His Trp Val Gln Lys Met Ala Gly Lys Gly Leu Lys Trp Leu
            35                  40                  45

Gly Trp Thr Asn Thr His Ser Gly Glu Pro Lys Tyr Ala Glu Asp Phe
        50                  55                  60

Lys Gly Arg Phe Ala Phe Ser Leu Asp Thr Ser Gly Ser Asp Ala Tyr
65                  70                  75                  80

Leu Gln Ile Gly Asn Leu Lys Tyr Glu Asp Ala Ala Thr Tyr Phe Cys
                85                  90                  95

Ala Lys Trp Gly Arg Gly Asn Ala Leu Asp Tyr Trp Gly Gln Gly Thr
            100                 105                 110

Ser Val Thr Val Ser Ser
            115

<210> SEQ ID NO 34
<211> LENGTH: 113
<212> TYPE: PRT
<213> ORGANISM: Artificial Sequence
<220> FEATURE:
<223> OTHER INFORMATION: Synthetic construct

<400> SEQUENCE: 34

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Asn Thr Val Gln Ala Glu Asp Leu Ala Val Tyr Tyr Cys Gln Asn
                85                  90                  95

Thr Tyr Ser Tyr Pro Leu Thr Phe Gly Gly Gly Thr Lys Leu Glu Leu
            100                 105                 110

Arg

<210> SEQ ID NO 35
<211> LENGTH: 120
<212> TYPE: PRT
<213> ORGANISM: Artificial Sequence
<220> FEATURE:
<223> OTHER INFORMATION: Synthetic construct

<400> SEQUENCE: 35

Gln Val Gln Leu Lys Gln Ser Gly Ala Glu Leu Val Arg Pro Gly Ala
1               5                   10                  15

Ser Val Ser Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
            35                  40                  45

Gly Arg Phe Tyr Pro Gly Thr Gly Thr Ala Tyr Tyr Asn Glu Asn Phe
        50                  55                  60

```
Glu Gly Lys Ala Thr Leu Thr Ala Asp Arg Ser Ser Thr Ala Tyr
65                  70                  75                  80

Met Gln Leu Ser Ser Leu Lys Asp Asp Ser Ala Val Tyr Phe Cys
                85                  90                  95

Thr Arg Glu Gly Tyr Gly Lys Gly Asn Ala Met Asp Tyr Trp Gly Gln
            100                 105                 110

Gly Thr Ser Val Thr Val Ser Ser
            115                 120

<210> SEQ ID NO 36
<211> LENGTH: 113
<212> TYPE: PRT
<213> ORGANISM: Artificial Sequence
<220> FEATURE:
<223> OTHER INFORMATION: Synthetic construct

<400> SEQUENCE: 36

Asp Ile Val Met Thr Gln Ser Pro Ser Ser Leu Thr Val Thr Thr Gly
1               5                   10                  15

Glu Lys Val Thr Leu Ser Cys Lys Ser Ser Gln Ser Leu Leu Asn Ser
                20                  25                  30

Gly Asn Gln Lys Asn Tyr Leu Thr Trp Tyr Gln Gln Lys Ser Gly Gln
            35                  40                  45

Pro Pro Glu Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Val Ser Ser Val Gln Ala Glu Asp Leu Ala Val Tyr Tyr Cys Gln Asn
                85                  90                  95

Asp Tyr Tyr Phe Pro Phe Thr Phe Gly Gly Gly Thr Lys Leu Glu Ile
            100                 105                 110

Lys

<210> SEQ ID NO 37
<211> LENGTH: 5
<212> TYPE: PRT
<213> ORGANISM: Artificial Sequence
<220> FEATURE:
<223> OTHER INFORMATION: Synthetic construct

<400> SEQUENCE: 37

Gly Tyr Trp Ile Glu
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic construct

<400> SEQUENCE: 38

Glu Ile Leu Leu Gly Ser Gly Ser Ile Lys Tyr Asn Val Lys Phe Lys
1               5                   10                  15

Asp

<210> SEQ ID NO 39
<211> LENGTH: 10
<212> TYPE: PRT
<213> ORGANISM: Artificial Sequence
<220> FEATURE:
```

```
<223> OTHER INFORMATION: Synthetic construct

<400> SEQUENCE: 39

Lys Gly Leu Arg Gly Asn Ser Phe Asp Tyr
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Synthetic construct

<400> SEQUENCE: 40

Asn Tyr Trp Thr His
1               5

<210> SEQ ID NO 41
<211> LENGTH: 17
<212> TYPE: PRT
<213> ORGANISM: Artificial Sequence
<220> FEATURE:
<223> OTHER INFORMATION: Synthetic construct

<400> SEQUENCE: 41

Met Ile His Pro Asn Ser Gly Ser Ser Asn Tyr Asn Glu Lys Phe Lys
1               5                   10                  15

Ser

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Ile His Tyr Gly Asn Ser Met Asp Tyr
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic construct

<400> SEQUENCE: 43

Ser Tyr Trp Thr His
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic construct

<400> SEQUENCE: 44

Ile His Tyr Gly Asn Ala Met Asp Tyr
1               5

<210> SEQ ID NO 45
<211> LENGTH: 5
<212> TYPE: PRT
<213> ORGANISM: Artificial Sequence
```

```
<220> FEATURE:
<223> OTHER INFORMATION: Synthetic construct

<400> SEQUENCE: 45

Asn Tyr Trp Met His
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic construct

<400> SEQUENCE: 46

Met Ile His Pro Asn Ser Tyr Ser Thr Asn Tyr Asn Glu Lys Phe Arg
1               5                   10                  15

Ser

<210> SEQ ID NO 47
<211> LENGTH: 9
<212> TYPE: PRT
<213> ORGANISM: Artificial Sequence
<220> FEATURE:
<223> OTHER INFORMATION: Synthetic construct

<400> SEQUENCE: 47

Ile Tyr Tyr Gly Asn Ala Met Asp Tyr
1               5

<210> SEQ ID NO 48
<211> LENGTH: 17
<212> TYPE: PRT
<213> ORGANISM: Artificial Sequence
<220> FEATURE:
<223> OTHER INFORMATION: Synthetic construct

<400> SEQUENCE: 48

Glu Ile Leu Pro Gly Ser Gly Ser Ile Lys Tyr Asn Glu Lys Phe Lys
1               5                   10                  15

Asp

<210> SEQ ID NO 49
<211> LENGTH: 5
<212> TYPE: PRT
<213> ORGANISM: Artificial Sequence
<220> FEATURE:
<223> OTHER INFORMATION: Synthetic construct

<400> SEQUENCE: 49

Asp Tyr His Met Asn
1               5

<210> SEQ ID NO 50
<211> LENGTH: 17
<212> TYPE: PRT
<213> ORGANISM: Artificial Sequence
<220> FEATURE:
<223> OTHER INFORMATION: Synthetic construct

<400> SEQUENCE: 50

Val Ile Asn Pro Tyr Asn Gly Gly Ile Arg Tyr Asn Gln Lys Phe Lys
1               5                   10                  15

Gly
```

```
<210> SEQ ID NO 51
<211> LENGTH: 9
<212> TYPE: PRT
<213> ORGANISM: Artificial Sequence
<220> FEATURE:
<223> OTHER INFORMATION: Synthetic construct

<400> SEQUENCE: 51

Ile Tyr Tyr Gly Asn Ser Phe Ala Tyr
1               5

<210> SEQ ID NO 52
<211> LENGTH: 17
<212> TYPE: PRT
<213> ORGANISM: Artificial Sequence
<220> FEATURE:
<223> OTHER INFORMATION: Synthetic construct

<400> SEQUENCE: 52

Leu Ile Asn Pro Tyr Asn Gly Gly Ile Arg Phe Asn Gln Lys Phe Lys
1               5                   10                  15

Gly

<210> SEQ ID NO 53
<211> LENGTH: 5
<212> TYPE: PRT
<213> ORGANISM: Artificial Sequence
<220> FEATURE:
<223> OTHER INFORMATION: Synthetic construct

<400> SEQUENCE: 53

Ser Tyr Trp Met Ile
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic construct

<400> SEQUENCE: 54

Gln Ile Tyr Pro Gly Asp Gly Asp Thr Asn Tyr Asn Gly Lys Phe Lys
1               5                   10                  15

Gly

<210> SEQ ID NO 55
<211> LENGTH: 9
<212> TYPE: PRT
<213> ORGANISM: Artificial Sequence
<220> FEATURE:
<223> OTHER INFORMATION: Synthetic construct

<400> SEQUENCE: 55

Ile Tyr Tyr Gly Asn Ala Phe Ala Tyr
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic construct

<400> SEQUENCE: 56
```

```
Asp Tyr Gln Met Asn
1               5

<210> SEQ ID NO 57
<211> LENGTH: 17
<212> TYPE: PRT
<213> ORGANISM: Artificial Sequence
<220> FEATURE:
<223> OTHER INFORMATION: Synthetic construct

<400> SEQUENCE: 57

Phe Ile Asn Pro Tyr Asn Gly Gly Ile Arg Tyr Asn Gln Lys Phe Lys
1               5                   10                  15

Gly

<210> SEQ ID NO 58
<211> LENGTH: 9
<212> TYPE: PRT
<213> ORGANISM: Artificial Sequence
<220> FEATURE:
<223> OTHER INFORMATION: Synthetic construct

<400> SEQUENCE: 58

Ile Tyr Phe Gly Asn Ser Phe Ala Asn
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic construct

<400> SEQUENCE: 59

Thr Tyr Gly Val Ser
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic construct

<400> SEQUENCE: 60

Val Ile Trp Gly Asp Gly Ser Thr Asn Tyr His Ser Ala Leu Ile Ser
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: Synthetic construct

<400> SEQUENCE: 61

Pro Gly Leu Arg Asn Ala Met Asp Tyr
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic construct

<400> SEQUENCE: 62
```

Asp Tyr Thr Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic construct

<400> SEQUENCE: 63

Phe Ile Gly Val Tyr Tyr Gly Asn Thr Asn Tyr Asn Gln Lys Phe Lys
1               5                   10                  15

Gly

<210> SEQ ID NO 64
<211> LENGTH: 9
<212> TYPE: PRT
<213> ORGANISM: Artificial Sequence
<220> FEATURE:
<223> OTHER INFORMATION: Synthetic construct

<400> SEQUENCE: 64

Ile Gly Arg Gly Asn Ala Met Asp Tyr
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic construct

<400> SEQUENCE: 65

Ser Gly Tyr Ser Trp His
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic construct

<400> SEQUENCE: 66

Tyr Ile His Tyr Ser Gly Gly Thr Asn Tyr Asn Pro Ser Leu Lys Ser
1               5                   10                  15

<210> SEQ ID NO 67
<211> LENGTH: 9
<212> TYPE: PRT
<213> ORGANISM: Artificial Sequence
<220> FEATURE:
<223> OTHER INFORMATION: Synthetic construct

<400> SEQUENCE: 67

Leu Glu Arg Gly Asn Ser Phe Ala Tyr
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic construct

```
<400> SEQUENCE: 68

Asn Tyr Val Met Ser
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic construct

<400> SEQUENCE: 69

Glu Ile Arg Thr Gly Gly Asp Tyr Thr Tyr Tyr Val Asp Thr Val Thr
1               5                   10                  15

Gly

<210> SEQ ID NO 70
<211> LENGTH: 9
<212> TYPE: PRT
<213> ORGANISM: Artificial Sequence
<220> FEATURE:
<223> OTHER INFORMATION: Synthetic construct

<400> SEQUENCE: 70

Val Gly Tyr Gly Asn Ser Leu Asp Tyr
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic construct

<400> SEQUENCE: 71

Asn Tyr Trp Ile His
1               5

<210> SEQ ID NO 72
<211> LENGTH: 17
<212> TYPE: PRT
<213> ORGANISM: Artificial Sequence
<220> FEATURE:
<223> OTHER INFORMATION: Synthetic construct

<400> SEQUENCE: 72

Arg Ile Tyr Pro Gly Thr Gly Asn Thr Tyr Tyr Asn Glu Lys Phe Thr
1               5                   10                  15

Gly

<210> SEQ ID NO 73
<211> LENGTH: 11
<212> TYPE: PRT
<213> ORGANISM: Artificial Sequence
<220> FEATURE:
<223> OTHER INFORMATION: Synthetic construct

<400> SEQUENCE: 73

Glu Gly Tyr Gly Lys Gly Asn Ser Met Asp Tyr
1               5                   10

<210> SEQ ID NO 74
<211> LENGTH: 5
<212> TYPE: PRT
<213> ORGANISM: Artificial Sequence
```

```
<220> FEATURE:
<223> OTHER INFORMATION: Synthetic construct

<400> SEQUENCE: 74

Ala Tyr Asn Met Asn
1               5

<210> SEQ ID NO 75
<211> LENGTH: 17
<212> TYPE: PRT
<213> ORGANISM: Artificial Sequence
<220> FEATURE:
<223> OTHER INFORMATION: Synthetic construct

<400> SEQUENCE: 75

Asn Ile Asp Pro Tyr Tyr Gly Gly Thr Asn Tyr Asn Gln Lys Phe Lys
1               5                   10                  15

Gly

<210> SEQ ID NO 76
<211> LENGTH: 9
<212> TYPE: PRT
<213> ORGANISM: Artificial Sequence
<220> FEATURE:
<223> OTHER INFORMATION: Synthetic construct

<400> SEQUENCE: 76

Val Tyr Tyr Gly Asn Ser Leu Ile Tyr
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic construct

<400> SEQUENCE: 77

Thr Phe Trp Ile His
1               5

<210> SEQ ID NO 78
<211> LENGTH: 17
<212> TYPE: PRT
<213> ORGANISM: Artificial Sequence
<220> FEATURE:
<223> OTHER INFORMATION: Synthetic construct

<400> SEQUENCE: 78

Lys Ile Tyr Pro Gly Thr Gly Tyr Thr Tyr Tyr Asn Glu Lys Phe Lys
1               5                   10                  15

Gly

<210> SEQ ID NO 79
<211> LENGTH: 11
<212> TYPE: PRT
<213> ORGANISM: Artificial Sequence
<220> FEATURE:
<223> OTHER INFORMATION: Synthetic construct

<400> SEQUENCE: 79

Glu Gly Tyr Gly Lys Gly Asn Ala Val Asp Phe
1               5                   10

<210> SEQ ID NO 80
```

```
<211> LENGTH: 5
<212> TYPE: PRT
<213> ORGANISM: Artificial Sequence
<220> FEATURE:
<223> OTHER INFORMATION: Synthetic construct

<400> SEQUENCE: 80

Thr Ala Gly Met His
1               5

<210> SEQ ID NO 81
<211> LENGTH: 17
<212> TYPE: PRT
<213> ORGANISM: Artificial Sequence
<220> FEATURE:
<223> OTHER INFORMATION: Synthetic construct

<400> SEQUENCE: 81

Trp Thr Asn Thr His Ser Gly Glu Pro Lys Tyr Ala Glu Asp Phe Lys
1               5                   10                  15

Gly

<210> SEQ ID NO 82
<211> LENGTH: 9
<212> TYPE: PRT
<213> ORGANISM: Artificial Sequence
<220> FEATURE:
<223> OTHER INFORMATION: Synthetic construct

<400> SEQUENCE: 82

Trp Gly Arg Gly Asn Ala Leu Asp Tyr
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic construct

<400> SEQUENCE: 83

Ser Tyr Trp Ile His
1               5

<210> SEQ ID NO 84
<211> LENGTH: 17
<212> TYPE: PRT
<213> ORGANISM: Artificial Sequence
<220> FEATURE:
<223> OTHER INFORMATION: Synthetic construct

<400> SEQUENCE: 84

Arg Phe Tyr Pro Gly Thr Gly Thr Ala Tyr Tyr Asn Glu Asn Phe Glu
1               5                   10                  15

Gly

<210> SEQ ID NO 85
<211> LENGTH: 11
<212> TYPE: PRT
<213> ORGANISM: Artificial Sequence
<220> FEATURE:
<223> OTHER INFORMATION: Synthetic construct

<400> SEQUENCE: 85

Glu Gly Tyr Gly Lys Gly Asn Ala Met Asp Tyr
1               5                   10
```

<210> SEQ ID NO 86
<211> LENGTH: 17
<212> TYPE: PRT
<213> ORGANISM: Artificial Sequence
<220> FEATURE:
<223> OTHER INFORMATION: Synthetic construct

<400> SEQUENCE: 86

Lys Ser Ser Gln Ser Leu Leu Asn Ser Gly Asn Gln Lys Ser Tyr Leu
1               5                   10                  15

Thr

<210> SEQ ID NO 87
<211> LENGTH: 17
<212> TYPE: PRT
<213> ORGANISM: Artificial Sequence
<220> FEATURE:
<223> OTHER INFORMATION: Synthetic construct

<400> SEQUENCE: 87

Lys Ser Ser Gln Ser Leu Phe Asn Ser Gly Asn Gln Lys Asn Tyr Leu
1               5                   10                  15

Thr

<210> SEQ ID NO 88
<211> LENGTH: 17
<212> TYPE: PRT
<213> ORGANISM: Artificial Sequence
<220> FEATURE:
<223> OTHER INFORMATION: Synthetic construct

<400> SEQUENCE: 88

Lys Ser Ser Gln Ser Leu Leu Asn Ser Gly Asn Gln Lys Asn Tyr Leu
1               5                   10                  15

Thr

<210> SEQ ID NO 89
<211> LENGTH: 17
<212> TYPE: PRT
<213> ORGANISM: Artificial Sequence
<220> FEATURE:
<223> OTHER INFORMATION: Synthetic construct

<400> SEQUENCE: 89

Lys Ser Gly Gln Ser Leu Leu Asn Ser Gly Asn Gln Lys Asn Tyr Leu
1               5                   10                  15

Thr

<210> SEQ ID NO 90
<211> LENGTH: 17
<212> TYPE: PRT
<213> ORGANISM: Artificial Sequence
<220> FEATURE:
<223> OTHER INFORMATION: Synthetic construct

<400> SEQUENCE: 90

Lys Pro Ser Gln Ser Leu Leu Asn Ser Gly Asn Gln Lys Asn Tyr Leu
1               5                   10                  15

Thr

<210> SEQ ID NO 91
<211> LENGTH: 17

```
<212> TYPE: PRT
<213> ORGANISM: Artificial Sequence
<220> FEATURE:
<223> OTHER INFORMATION: Synthetic construct

<400> SEQUENCE: 91

Lys Ser Ser Gln Ser Leu Leu Asn Ser Gly Asn Gln Lys Asn Tyr Leu
1               5                   10                  15
Ala

<210> SEQ ID NO 92
<211> LENGTH: 17
<212> TYPE: PRT
<213> ORGANISM: Artificial Sequence
<220> FEATURE:
<223> OTHER INFORMATION: Synthetic construct

<400> SEQUENCE: 92

Lys Ser Thr Gln Ser Leu Leu Asn Ser Gly Asn Gln Lys Asn Tyr Leu
1               5                   10                  15
Thr

<210> SEQ ID NO 93
<211> LENGTH: 7
<212> TYPE: PRT
<213> ORGANISM: Artificial Sequence
<220> FEATURE:
<223> OTHER INFORMATION: Synthetic construct

<400> SEQUENCE: 93

Trp Ala Ser Thr Arg Glu Ser
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic construct

<400> SEQUENCE: 94

Trp Ala Ser Thr Trp Glu Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic construct

<400> SEQUENCE: 95

Trp Ala Phe Thr Arg Glu Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic construct

<400> SEQUENCE: 96

Gly Ala Ser Thr Arg Glu Ser
1               5
```

```
<210> SEQ ID NO 97
<211> LENGTH: 9
<212> TYPE: PRT
<213> ORGANISM: Artificial Sequence
<220> FEATURE:
<223> OTHER INFORMATION: Synthetic construct

<400> SEQUENCE: 97

Gln Asn Asp Tyr Tyr Tyr Pro Phe Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic construct

<400> SEQUENCE: 98

Gln Asn Ala Tyr Ser Tyr Pro Phe Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic construct

<400> SEQUENCE: 99

Gln Asn Asp Tyr Ser Phe Pro Phe Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic construct

<400> SEQUENCE: 100

Gln Asn Asp Tyr Ser Tyr Pro Phe Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic construct

<400> SEQUENCE: 101

Gln Asn Asn Tyr Ile Tyr Pro Phe Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic construct

<400> SEQUENCE: 102

Gln Asn Asp Tyr Phe Tyr Pro Tyr Thr
1               5
```

```
<210> SEQ ID NO 103
<211> LENGTH: 9
<212> TYPE: PRT
<213> ORGANISM: Artificial Sequence
<220> FEATURE:
<223> OTHER INFORMATION: Synthetic construct

<400> SEQUENCE: 103

Gln Asn Asp Tyr Ile Tyr Pro Tyr Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic construct

<400> SEQUENCE: 104

Gln Asn Asp Leu Ile Tyr Pro Leu Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic construct

<400> SEQUENCE: 105

Gln Asn Asp Tyr Phe Tyr Pro Phe Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic construct

<400> SEQUENCE: 106

Gln Asn Asn Tyr Phe Tyr Pro Leu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic construct

<400> SEQUENCE: 107

Gln Asn Ala Tyr Tyr Tyr Pro Tyr Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic construct

<400> SEQUENCE: 108

Gln Asn Asp Tyr Thr Tyr Pro Ser Thr
1               5

<210> SEQ ID NO 109
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 109

Gln Asn Thr Tyr Ser Tyr Pro Leu Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic construct

<400> SEQUENCE: 110

Gln Asn Asp Tyr Tyr Phe Pro Phe Thr
1               5

<210> SEQ ID NO 111
<211> LENGTH: 17
<212> TYPE: PRT
<213> ORGANISM: Artificial Sequence
<220> FEATURE:
<223> OTHER INFORMATION: Synthetic construct

<400> SEQUENCE: 111

Lys Ser Ser Gln Ser Leu Leu Gln Ser Gly Asn Gln Lys Asn Tyr Leu
1               5                   10                  15

Thr

<210> SEQ ID NO 112
<211> LENGTH: 17
<212> TYPE: PRT
<213> ORGANISM: Artificial Sequence
<220> FEATURE:
<223> OTHER INFORMATION: Synthetic construct

<400> SEQUENCE: 112

Lys Ser Ser Gln Ser Leu Leu Asn Ala Gly Asn Gln Lys Asn Tyr Leu
1               5                   10                  15

Thr

<210> SEQ ID NO 113
<211> LENGTH: 17
<212> TYPE: PRT
<213> ORGANISM: Artificial Sequence
<220> FEATURE:
<223> OTHER INFORMATION: Synthetic construct

<400> SEQUENCE: 113

Lys Ser Ser Gln Ser Leu Leu Asn Ser Ala Asn Gln Lys Asn Tyr Leu
1               5                   10                  15

Thr

<210> SEQ ID NO 114
<211> LENGTH: 113
<212> TYPE: PRT
<213> ORGANISM: Artificial Sequence
<220> FEATURE:
<223> OTHER INFORMATION: Synthetic construct

<400> SEQUENCE: 114
```

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Gln Ser
            20                  25                  30

Gly Asn Gln Lys Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr His Cys Gln Asn
                85                  90                  95

Ala Tyr Tyr Tyr Pro Tyr Thr Phe Gly Gly Gly Thr Lys Leu Glu Met
            100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: Synthetic construct

<400> SEQUENCE: 115

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr His Cys Gln Asn
                85                  90                  95

Ala Tyr Tyr Tyr Pro Tyr Thr Phe Gly Gly Gly Thr Lys Leu Glu Met
            100                 105                 110

Lys

<210> SEQ ID NO 116
<211> LENGTH: 113
<212> TYPE: PRT
<213> ORGANISM: Artificial Sequence
<220> FEATURE:
<223> OTHER INFORMATION: Synthetic construct

<400> SEQUENCE: 116

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Ala Asn Gln Lys Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Thr Gly Ser Gly Ser Gly Thr Asp Phe Thr Leu Thr

```
                65                  70                  75                  80
Ile Ser Ser Val Gln Ala Glu Asp Leu Ala Val Tyr His Cys Gln Asn
                    85                  90                  95

Ala Tyr Tyr Tyr Pro Tyr Thr Phe Gly Gly Gly Thr Lys Leu Glu Met
                100                 105                 110

Lys

<210> SEQ ID NO 117
<211> LENGTH: 113
<212> TYPE: PRT
<213> ORGANISM: Artificial Sequence
<220> FEATURE:
<223> OTHER INFORMATION: Synthetic construct

<400> SEQUENCE: 117

Asp Ile Val Met Thr Gln Ser Pro Ser Ser Leu Thr Val Thr Thr Gly
1               5                   10                  15

Glu Lys Val Thr Leu Ser Cys Lys Ser Ser Gln Ser Leu Leu Gln Ser
                20                  25                  30

Gly Asn Gln Lys Asn Tyr Leu Thr Trp Tyr Gln Gln Lys Ser Gly Gln
            35                  40                  45

Pro Pro Glu Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Val Ser Ser Val Gln Ala Glu Asp Leu Ala Val Tyr Tyr Cys Gln Asn
                    85                  90                  95

Asp Tyr Tyr Phe Pro Phe Thr Phe Gly Gly Gly Thr Lys Leu Glu Ile
                100                 105                 110

Lys

<210> SEQ ID NO 118
<211> LENGTH: 113
<212> TYPE: PRT
<213> ORGANISM: Artificial Sequence
<220> FEATURE:
<223> OTHER INFORMATION: Synthetic construct

<400> SEQUENCE: 118

Asp Ile Val Met Thr Gln Ser Pro Ser Ser Leu Thr Val Thr Thr Gly
1               5                   10                  15

Glu Lys Val Thr Leu Ser Cys Lys Ser Ser Gln Ser Leu Leu Asn Ala
                20                  25                  30

Gly Asn Gln Lys Asn Tyr Leu Thr Trp Tyr Gln Gln Lys Ser Gly Gln
            35                  40                  45

Pro Pro Glu Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Val Ser Ser Val Gln Ala Glu Asp Leu Ala Val Tyr Tyr Cys Gln Asn
                    85                  90                  95

Asp Tyr Tyr Phe Pro Phe Thr Phe Gly Gly Gly Thr Lys Leu Glu Ile
                100                 105                 110

Lys

<210> SEQ ID NO 119
<211> LENGTH: 113
```

```
<212> TYPE: PRT
<213> ORGANISM: Artificial Sequence
<220> FEATURE:
<223> OTHER INFORMATION: Synthetic construct

<400> SEQUENCE: 119

Asp Ile Val Met Thr Gln Ser Pro Ser Ser Leu Thr Val Thr Thr Gly
1               5                   10                  15

Glu Lys Val Thr Leu Ser Cys Lys Ser Ser Gln Ser Leu Leu Asn Ser
            20                  25                  30

Ala Asn Gln Lys Asn Tyr Leu Thr Trp Tyr Gln Gln Lys Ser Gly Gln
        35                  40                  45

Pro Pro Glu Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Val Ser Ser Val Gln Ala Glu Asp Leu Ala Val Tyr Tyr Cys Gln Asn
                85                  90                  95

Asp Tyr Tyr Phe Pro Phe Thr Phe Gly Gly Gly Thr Lys Leu Glu Ile
            100                 105                 110

Lys

<210> SEQ ID NO 120
<211> LENGTH: 120
<212> TYPE: PRT
<213> ORGANISM: Artificial Sequence
<220> FEATURE:
<223> OTHER INFORMATION: Synthetic construct

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Trp Ile His Trp Val Arg Gln Ala Pro Gly Gln Gly Leu Glu Trp Met
        35                  40                  45

Gly Arg Ile Tyr Pro Gly Thr Gly Asn Thr Tyr Tyr Asn Glu Lys Phe
    50                  55                  60

Thr Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Gly Lys Gly Asn Ser Met Asp Tyr Trp Gly Gln
            100                 105                 110

Gly Thr Thr Val Thr Val Ser Ser
        115                 120

<210> SEQ ID NO 121
<211> LENGTH: 113
<212> TYPE: PRT
<213> ORGANISM: Artificial Sequence
<220> FEATURE:
<223> OTHER INFORMATION: Synthetic construct

<400> SEQUENCE: 121

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30
```

```
Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Ala Tyr Tyr Tyr Pro Tyr Thr Phe Gly Gly Gly Thr Lys Leu Glu Ile
                100                 105                 110

Lys
```

<210> SEQ ID NO 122
<211> LENGTH: 120
<212> TYPE: PRT
<213> ORGANISM: Artificial Sequence
<220> FEATURE:
<223> OTHER INFORMATION: Synthetic construct

<400> SEQUENCE: 122

```
Gln Val Gln Leu Val Gln Ser Gly Ala Glu Val Lys Lys Pro Gly Ala
 1               5                   10                  15

Ser Val Lys Val Ser Cys Lys Thr Ser Gly Tyr Ile Phe Thr Asn Tyr
                20                  25                  30

Trp Ile His Trp Val Arg Gln Ala Pro Gly Gln Gly Leu Glu Trp Met
            35                  40                  45

Gly Arg Ile Tyr Pro Gly Thr Gly Asn Thr Tyr Tyr Asn Glu Lys Phe
 50                  55                  60

Thr Gly Arg Val Thr Leu Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ser Arg Glu Gly Tyr Gly Lys Gly Asn Ser Met Asp Tyr Trp Gly Gln
                100                 105                 110

Gly Thr Thr Val Thr Val Ser Ser
            115                 120
```

<210> SEQ ID NO 123
<211> LENGTH: 113
<212> TYPE: PRT
<213> ORGANISM: Artificial Sequence
<220> FEATURE:
<223> OTHER INFORMATION: Synthetic construct

<400> SEQUENCE: 123

```
Asp Ile Val Met Thr Gln Ser Pro Asp Ser Leu Ala Val Ser Leu Gly
 1               5                   10                  15

Glu Arg Ala Thr Met Asn Cys Lys Ser Ser Gln Ser Leu Leu Asn Ala
                20                  25                  30

Gly Asn Gln Lys Asn Tyr Leu Thr Trp Tyr Gln Gln Lys Pro Gly Gln
            35                  40                  45

Pro Pro Lys Leu Leu Phe Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr His Cys Gln Asn
                85                  90                  95
```

Ala Tyr Tyr Tyr Pro Tyr Thr Phe Gly Gly Gly Thr Lys Leu Glu Ile
            100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Synthetic construct

<400> SEQUENCE: 124

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr His Cys Gln Asn
                85                  90                  95

Ala Tyr Tyr Tyr Pro Tyr Thr Phe Gly Gly Gly Thr Lys Leu Glu Ile
            100                 105                 110

Lys

<210> SEQ ID NO 125
<211> LENGTH: 120
<212> TYPE: PRT
<213> ORGANISM: Artificial Sequence
<220> FEATURE:
<223> OTHER INFORMATION: Synthetic construct

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Ile His Trp Val Arg Gln Ala Pro Gly Gln Gly Leu Glu Trp Met
        35                  40                  45

Gly Arg Phe Tyr Pro Gly Thr Gly Thr Ala Tyr Tyr Asn Glu Asn Phe
    50                  55                  60

Glu Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Glu Gly Tyr Gly Lys Gly Asn Ser Met Asp Tyr Trp Gly Gln
            100                 105                 110

Gly Thr Thr Val Thr Val Ser Ser
        115                 120

<210> SEQ ID NO 126
<211> LENGTH: 113
<212> TYPE: PRT
<213> ORGANISM: Artificial Sequence
<220> FEATURE:

<223> OTHER INFORMATION: Synthetic construct

<400> SEQUENCE: 126

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Tyr Phe Pro Phe Thr Phe Gly Gly Gly Thr Lys Leu Glu Ile
            100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Synthetic construct

<400> SEQUENCE: 127

Asp Ile Val Met Thr Gln Ser Pro Asp Ser Leu Ala Val Ser Leu Gly
1               5                   10                  15

Glu Arg Val Thr Leu Asn Cys Lys Ser Ser Gln Ser Leu Leu Gln Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Val Ser Ser Val Gln Ala Glu Asp Val Ala Val Tyr Tyr Cys Gln Asn
                85                  90                  95

Asp Tyr Tyr Phe Pro Phe Thr Phe Gly Gly Gly Thr Lys Leu Glu Ile
            100                 105                 110

Lys

<210> SEQ ID NO 128
<211> LENGTH: 120
<212> TYPE: PRT
<213> ORGANISM: Artificial Sequence
<220> FEATURE:
<223> OTHER INFORMATION: Synthetic construct

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ile Phe Thr Ser Tyr
            20                  25                  30

Trp Ile His Trp Val Arg Gln Ala Pro Gly Gln Gly Leu Glu Trp Met
        35                  40                  45

-continued

```
Gly Arg Phe Tyr Pro Gly Thr Gly Thr Ala Tyr Tyr Asn Glu Asn Phe
    50                  55                  60

Glu Gly Arg Val Thr Leu Thr Ala Asp Thr Ser Ile Ser Thr Ala Tyr
65              70                  75                  80

Met Glu Leu Ser Arg Leu Arg Ser Asp Thr Ala Val Tyr Tyr Cys
            85                  90                  95

Thr Arg Glu Gly Tyr Gly Lys Gly Asn Ser Met Asp Tyr Trp Gly Gln
            100                 105                 110

Gly Thr Thr Val Thr Val Ser Ser
        115                 120
```